US010252048B2

(12) United States Patent
Loudin et al.

(10) Patent No.: US 10,252,048 B2
(45) Date of Patent: Apr. 9, 2019

(54) NASAL STIMULATION FOR RHINITIS, NASAL CONGESTION, AND OCULAR ALLERGIES

(71) Applicant: Oculeve, Inc., South San Francisco, CA (US)

(72) Inventors: James Donald Loudin, Houston, TX (US); Daniel N. Hamilton, Napa, CA (US); Manfred Franke, Valencia, CA (US); Douglas Michael Ackermann, San Francisco, CA (US)

(73) Assignee: Oculeve, Inc., South San Francisco, CA (US)

( * ) Notice: Subject to any disclaimer, the term of this patent is extended or adjusted under 35 U.S.C. 154(b) by 0 days.

(21) Appl. No.: 15/438,577

(22) Filed: Feb. 21, 2017

(65) Prior Publication Data

US 2017/0239459 A1 Aug. 24, 2017

Related U.S. Application Data

(60) Provisional application No. 62/297,734, filed on Feb. 19, 2016.

(51) Int. Cl.
*A61N 1/00* (2006.01)
*A61N 1/05* (2006.01)
(Continued)

(52) U.S. Cl.
CPC ....... *A61N 1/0546* (2013.01); *A61N 1/36014* (2013.01); *A61N 1/0456* (2013.01); *A61N 1/36034* (2017.08)

(58) Field of Classification Search
CPC .............. A61N 1/0546; A61N 1/36014; A61N 1/0456; A61N 1/36034
See application file for complete search history.

(56) References Cited

U.S. PATENT DOCUMENTS 3,620,219 A 11/1971 Barker
3,709,228 A 1/1973 Barker et al.
(Continued)

FOREIGN PATENT DOCUMENTS

CN 101939043 A 1/2011
CN 103467652 A 12/2013
(Continued)

OTHER PUBLICATIONS

Acar, M. et al. (2013). "Ocular surface assessment in patients with obstructive sleep apnea-hypopnea syndrome," Sleep Breath 17(2):583-588.
(Continued)

*Primary Examiner* — George Manuel
(74) *Attorney, Agent, or Firm* — Mintz Levin Cohn Ferris Glovsky and Popeo, P.C.

(57) ABSTRACT

Described here are devices, systems, and methods for treating one or more conditions, such as allergic rhinitis, non-allergic rhinitis, nasal congestion, ocular allergy, and/or symptoms associated with these conditions, by providing stimulation to nasal or sinus tissue. In some variations, the handheld devices may have a stimulator body and a stimulator probe having one or more nasal insertion prongs, and the nasal insertion prongs may be configured to deliver an electrical stimulus to the tissue.

18 Claims, 20 Drawing Sheets

(51) Int. Cl.
*A61N 1/36* (2006.01)
*A61N 1/04* (2006.01)

(56) References Cited

U.S. PATENT DOCUMENTS

| | | |
|---|---|---|
| 3,885,550 A | 5/1975 | MacLeod |
| D257,495 S | 11/1980 | Bros et al. |
| 4,495,676 A | 1/1985 | Hartmetz |
| 4,520,825 A | 6/1985 | Thompson et al. |
| 4,539,988 A | 9/1985 | Shirley et al. |
| 4,590,942 A | 5/1986 | Brenman et al. |
| 4,628,933 A | 12/1986 | Michelson |
| 4,681,121 A | 7/1987 | Kobal |
| 4,684,362 A | 8/1987 | Holt |
| 4,706,680 A | 11/1987 | Keusch et al. |
| 4,735,207 A | 4/1988 | Nambu et al. |
| 4,777,954 A | 10/1988 | Keusch et al. |
| 4,780,932 A | 11/1988 | Bowman et al. |
| 4,868,154 A | 9/1989 | Gilbard et al. |
| 4,926,880 A | 5/1990 | Claude et al. |
| 4,957,480 A | 9/1990 | Morenings |
| 4,988,358 A | 1/1991 | Eppley et al. |
| 5,025,807 A | 6/1991 | Zabara |
| 5,072,724 A | 12/1991 | Marcus |
| 5,078,733 A | 1/1992 | Eveleigh et al. |
| 5,090,422 A | 2/1992 | Dahl et al. |
| 5,099,829 A | 3/1992 | Wu |
| 5,147,284 A | 9/1992 | Fedorov et al. |
| 5,324,316 A | 6/1994 | Schulman et al. |
| 5,342,410 A | 8/1994 | Braverman |
| 5,345,948 A | 9/1994 | O'Donnell, Jr. |
| 5,360,438 A | 11/1994 | Fisher |
| 5,498,681 A | 3/1996 | Askari et al. |
| 5,514,131 A | 5/1996 | Edwards et al. |
| 5,533,470 A | 7/1996 | Rose |
| 5,545,617 A | 8/1996 | Dartt et al. |
| 5,571,101 A | 11/1996 | Ellman et al. |
| 5,607,461 A | 3/1997 | Lathrop |
| 5,640,978 A | 6/1997 | Wong |
| 5,683,436 A | 11/1997 | Mendes et al. |
| 5,697,957 A | 12/1997 | Noren et al. |
| 5,707,400 A | 1/1998 | Terry et al. |
| 5,713,833 A | 2/1998 | Milligan |
| 5,720,773 A | 2/1998 | Lopez-Claros |
| 5,733,282 A | 3/1998 | Ellman et al. |
| 5,735,817 A | 4/1998 | Shantha |
| 5,792,100 A | 8/1998 | Shantha |
| 5,794,614 A | 8/1998 | Gruenke et al. |
| 5,800,685 A | 9/1998 | Perrault |
| 5,843,140 A | 12/1998 | Strojnik |
| 5,900,407 A | 5/1999 | Yerxa et al. |
| 5,904,658 A | 5/1999 | Niederauer et al. |
| 5,948,006 A | 9/1999 | Mann |
| 6,001,088 A | 12/1999 | Roberts et al. |
| 6,020,445 A | 2/2000 | Vanderlaan et al. |
| 6,035,236 A | 3/2000 | Jarding et al. |
| 6,050,999 A | 4/2000 | Paraschac et al. |
| 6,051,017 A | 4/2000 | Loeb et al. |
| 6,083,251 A | 7/2000 | Shindo |
| 6,102,847 A | 8/2000 | Stielau |
| 6,152,916 A | 11/2000 | Bige |
| 6,205,359 B1 | 3/2001 | Boveja |
| 6,208,902 B1 | 3/2001 | Boveja |
| 6,240,316 B1 | 5/2001 | Richmond et al. |
| 6,246,911 B1 | 6/2001 | Seligman |
| 6,270,796 B1 | 8/2001 | Weinstein |
| 6,272,382 B1 | 8/2001 | Faltys et al. |
| 6,275,737 B1 | 8/2001 | Mann |
| 6,277,855 B1 | 8/2001 | Yerxa |
| 6,284,765 B1 | 9/2001 | Caffrey |
| 6,324,429 B1 | 11/2001 | Shire et al. |
| 6,327,504 B1 | 12/2001 | Dolgin et al. |
| 6,366,814 B1 | 4/2002 | Boveja et al. |
| 6,405,079 B1 | 6/2002 | Ansarinia et al. |
| 6,438,398 B1 | 8/2002 | Pflugfelder et al. |
| 6,458,157 B1 | 10/2002 | Suaning |
| 6,505,077 B1 | 1/2003 | Kast et al. |
| 6,526,318 B1 | 2/2003 | Ansarinia et al. |
| 6,535,766 B1 | 3/2003 | Thompson et al. |
| 6,537,265 B2 | 3/2003 | Thanavala et al. |
| 6,539,253 B2 | 3/2003 | Thompson et al. |
| 6,562,036 B1 | 5/2003 | Ellman et al. |
| 6,564,102 B1 | 5/2003 | Boveja |
| 6,578,579 B2 | 6/2003 | Burnside et al. |
| 6,604,528 B1 | 8/2003 | Duncan |
| 6,641,799 B2 | 11/2003 | Goldberg |
| 6,658,301 B2 | 12/2003 | Loeb et al. |
| 6,662,052 B1 | 12/2003 | Sarwal et al. |
| 6,684,879 B1 | 2/2004 | Coffee et al. |
| 6,701,189 B2 | 3/2004 | Fang et al. |
| 6,748,951 B1 | 6/2004 | Schmidt |
| 6,792,314 B2 | 9/2004 | Byers et al. |
| 6,829,508 B2 | 12/2004 | Schulman et al. |
| 6,853,858 B2 | 2/2005 | Shalev |
| 6,871,099 B1 | 3/2005 | Whitehurst et al. |
| 6,879,859 B1 | 4/2005 | Boveja |
| 6,885,888 B2 | 4/2005 | Rezai |
| 6,895,279 B2 | 5/2005 | Loeb et al. |
| 7,024,241 B1 | 4/2006 | Bornzin et al. |
| 7,054,692 B1 | 5/2006 | Whitehurst et al. |
| 7,067,307 B2 | 6/2006 | Hochleitner et al. |
| 7,069,084 B2 | 6/2006 | Yee |
| 7,117,033 B2 | 10/2006 | Shalev et al. |
| 7,142,909 B2 | 11/2006 | Greenberg et al. |
| 7,146,209 B2 | 12/2006 | Gross et al. |
| 7,169,163 B2 | 1/2007 | Becker |
| 7,190,998 B2 | 3/2007 | Shalev et al. |
| 7,225,032 B2 | 5/2007 | Schmeling et al. |
| 7,228,184 B2 | 6/2007 | Heath |
| 7,247,692 B2 | 7/2007 | Laredo |
| 7,317,947 B2 | 1/2008 | Wahlstrand et al. |
| 7,330,762 B2 | 2/2008 | Boveja et al. |
| 7,346,398 B2 | 3/2008 | Gross et al. |
| 7,369,897 B2 | 5/2008 | Boveja et al. |
| 7,442,191 B2 | 10/2008 | Hovda et al. |
| 7,460,911 B2 | 12/2008 | Cosendai et al. |
| 7,477,947 B2 | 1/2009 | Pines et al. |
| 7,502,652 B2 | 3/2009 | Gaunt et al. |
| 7,547,447 B2 | 6/2009 | Yiu et al. |
| 7,565,204 B2 | 7/2009 | Matei et al. |
| 7,599,737 B2 | 10/2009 | Yomtov et al. |
| 7,636,597 B2 | 12/2009 | Gross et al. |
| 7,650,186 B2 | 1/2010 | Hastings et al. |
| D613,408 S | 4/2010 | Gausmann et al. |
| D614,303 S | 4/2010 | Gausmann et al. |
| D614,774 S | 4/2010 | Gausmann et al. |
| 7,725,176 B2 | 5/2010 | Schuler et al. |
| 7,725,195 B2 | 5/2010 | Lima et al. |
| D617,443 S | 6/2010 | Grenon et al. |
| 7,758,190 B2 | 7/2010 | Korb et al. |
| 7,778,703 B2 | 8/2010 | Gross et al. |
| 7,778,711 B2 | 8/2010 | Ben-David et al. |
| 7,792,591 B2 | 9/2010 | Rooney et al. |
| 7,805,200 B2 | 9/2010 | Kast et al. |
| 7,805,202 B2 | 9/2010 | Kuzma et al. |
| 7,805,203 B2 | 9/2010 | Ben-David et al. |
| 7,809,442 B2 | 10/2010 | Bolea et al. |
| 7,835,794 B2 | 11/2010 | Greenberg et al. |
| 7,846,124 B2 | 12/2010 | Becker |
| 7,860,570 B2 | 12/2010 | Whitehurst et al. |
| 7,873,421 B2 | 1/2011 | Karell |
| 7,879,079 B2 | 2/2011 | Tu et al. |
| D638,128 S | 5/2011 | Prokop et al. |
| 7,981,095 B2 | 7/2011 | Grenon et al. |
| 7,993,381 B2 | 8/2011 | Mac et al. |
| 7,998,202 B2 | 8/2011 | Lesh |
| 8,002,783 B2 | 8/2011 | Vercellotti et al. |
| 8,019,419 B1 | 9/2011 | Panescu et al. |
| 8,019,441 B2 | 9/2011 | Wallace et al. |
| 8,080,047 B2 | 12/2011 | Yu |
| 8,145,322 B1 | 3/2012 | Yao et al. |
| 8,155,746 B2 | 4/2012 | Maltan et al. |
| 8,165,680 B2 | 4/2012 | Greenberg et al. |
| 8,204,591 B2 | 6/2012 | Ben-David et al. |

(56) References Cited

U.S. PATENT DOCUMENTS

| | | |
|---|---|---|
| 8,231,218 B2 | 7/2012 | Hong et al. |
| 8,251,983 B2 | 8/2012 | Larson et al. |
| 8,295,529 B2 | 10/2012 | Petersen et al. |
| 8,318,070 B2 | 11/2012 | Shiah et al. |
| D681,839 S | 5/2013 | Nathanson |
| 8,489,189 B2 | 7/2013 | Tronnes |
| 8,494,641 B2 | 7/2013 | Boling et al. |
| 8,626,298 B2 | 1/2014 | Simon |
| 8,676,324 B2 | 3/2014 | Simon et al. |
| 8,728,136 B2 | 5/2014 | Feldman |
| 8,918,181 B2 | 12/2014 | Ackermann et al. |
| 8,936,594 B2 | 1/2015 | Wolf et al. |
| 8,986,301 B2 | 3/2015 | Wolf et al. |
| 8,996,137 B2 | 3/2015 | Ackermann et al. |
| 9,079,042 B2 | 7/2015 | Tiedtke et al. |
| 9,095,723 B2 | 8/2015 | Ackermann et al. |
| 9,265,956 B2 | 2/2016 | Ackermann et al. |
| 9,440,065 B2 | 9/2016 | Ackermann et al. |
| 9,687,652 B2 | 6/2017 | Franke et al. |
| 9,717,627 B2 | 8/2017 | Kuzma et al. |
| 9,737,702 B2 | 8/2017 | Ackermann et al. |
| 9,737,712 B2 | 8/2017 | Franke et al. |
| 9,764,150 B2 | 9/2017 | Loudin et al. |
| 9,770,583 B2 | 9/2017 | Gupta et al. |
| 9,821,159 B2 | 11/2017 | Ackermann et al. |
| 2001/0018918 A1 | 9/2001 | Burnside et al. |
| 2001/0020177 A1 | 9/2001 | Gruzdowich et al. |
| 2002/0013594 A1 | 1/2002 | Dinger et al. |
| 2002/0035358 A1 | 3/2002 | Wang |
| 2002/0049290 A1 | 4/2002 | Vanderbilt et al. |
| 2002/0188331 A1 | 12/2002 | Fang et al. |
| 2003/0045909 A1 | 3/2003 | Gross et al. |
| 2003/0114899 A1 | 6/2003 | Woods et al. |
| 2003/0120323 A1 | 6/2003 | Meadows et al. |
| 2003/0130809 A1 | 7/2003 | Cohen et al. |
| 2003/0176898 A1 | 9/2003 | Gross et al. |
| 2003/0192784 A1 | 10/2003 | Zhou et al. |
| 2003/0233134 A1 | 12/2003 | Greenberg et al. |
| 2003/0233135 A1 | 12/2003 | Yee |
| 2004/0050392 A1 | 3/2004 | Tu et al. |
| 2004/0059466 A1 | 3/2004 | Block et al. |
| 2004/0098036 A1 | 5/2004 | Bergersen |
| 2004/0098067 A1 | 5/2004 | Ohta et al. |
| 2004/0127942 A1 | 7/2004 | Yomtov et al. |
| 2004/0138646 A1 | 7/2004 | Walla |
| 2004/0147973 A1 | 7/2004 | Hauser et al. |
| 2004/0151930 A1 | 8/2004 | Rouns et al. |
| 2004/0220644 A1 | 11/2004 | Shalev et al. |
| 2005/0004621 A1 | 1/2005 | Boveja et al. |
| 2005/0010250 A1 | 1/2005 | Schuler et al. |
| 2005/0010266 A1 | 1/2005 | Bogdanowicz |
| 2005/0101967 A1 | 5/2005 | Weber et al. |
| 2005/0101994 A1 | 5/2005 | Yamazaki et al. |
| 2005/0105046 A1 | 5/2005 | Tung |
| 2005/0137276 A1 | 6/2005 | Yahiaoui et al. |
| 2005/0159790 A1 | 7/2005 | Shalev et al. |
| 2005/0197675 A1 | 9/2005 | David et al. |
| 2005/0251061 A1 | 11/2005 | Schuler et al. |
| 2005/0267542 A1 | 12/2005 | David et al. |
| 2005/0268472 A1 | 12/2005 | Bourilkov et al. |
| 2006/0004423 A1 | 1/2006 | Boveja et al. |
| 2006/0018872 A1 | 1/2006 | Tew et al. |
| 2006/0074450 A1 | 4/2006 | Boveja et al. |
| 2006/0089673 A1 | 4/2006 | Schultheiss et al. |
| 2006/0095077 A1 | 5/2006 | Tronnes et al. |
| 2006/0095108 A1 | 5/2006 | Chowdhury et al. |
| 2006/0100668 A1 | 5/2006 | Ben-David et al. |
| 2006/0107958 A1 | 5/2006 | Sleeper |
| 2006/0142822 A1 | 6/2006 | Tulgar |
| 2006/0161225 A1 | 7/2006 | Sormann et al. |
| 2006/0195169 A1 | 8/2006 | Gross et al. |
| 2006/0206155 A1 | 9/2006 | Ben-David et al. |
| 2006/0216317 A1 | 9/2006 | Reinhard et al. |
| 2006/0239482 A1 | 10/2006 | Hatoum et al. |
| 2006/0259098 A1 | 11/2006 | Erickson |
| 2006/0271024 A1 | 11/2006 | Gertner et al. |
| 2006/0271108 A1 | 11/2006 | Libbus et al. |
| 2007/0038267 A1 | 2/2007 | Shodo et al. |
| 2007/0060815 A1 | 3/2007 | Martin et al. |
| 2007/0060954 A1 | 3/2007 | Cameron et al. |
| 2007/0083245 A1 | 4/2007 | Lamensdorf et al. |
| 2007/0123938 A1 | 5/2007 | Haller et al. |
| 2007/0135868 A1 | 6/2007 | Shi et al. |
| 2007/0150034 A1 | 6/2007 | Rooney et al. |
| 2007/0219600 A1 | 9/2007 | Gertner et al. |
| 2007/0237797 A1 | 10/2007 | Peyman |
| 2007/0237825 A1 | 10/2007 | Levy et al. |
| 2007/0248930 A1 | 10/2007 | Brawn |
| 2007/0250119 A1 | 10/2007 | Tyler et al. |
| 2007/0250135 A1 | 10/2007 | Bartz-Schmidt et al. |
| 2007/0276314 A1 | 11/2007 | Becker |
| 2007/0276451 A1 | 11/2007 | Rigaux |
| 2007/0295327 A1 | 12/2007 | Bottomley |
| 2007/0299462 A1 | 12/2007 | Becker |
| 2008/0009897 A1 | 1/2008 | Duran Von Arx |
| 2008/0021515 A1 | 1/2008 | Horsager et al. |
| 2008/0082057 A1 | 4/2008 | Korb et al. |
| 2008/0082131 A1 | 4/2008 | Llanos |
| 2008/0109054 A1 | 5/2008 | Hastings et al. |
| 2008/0132933 A1 | 6/2008 | Gerber |
| 2008/0140141 A1 | 6/2008 | Ben-David et al. |
| 2008/0183242 A1 | 7/2008 | Tano et al. |
| 2008/0183243 A1 | 7/2008 | Shodo et al. |
| 2008/0208335 A1 | 8/2008 | Blum et al. |
| 2008/0221642 A1 | 9/2008 | Humayun et al. |
| 2008/0269648 A1 | 10/2008 | Bock |
| 2008/0294066 A1 | 11/2008 | Hetling et al. |
| 2009/0005835 A1 | 1/2009 | Greenberg et al. |
| 2009/0012573 A1 | 1/2009 | Karell et al. |
| 2009/0018582 A1 | 1/2009 | Ishikawa et al. |
| 2009/0024187 A1 | 1/2009 | Erickson et al. |
| 2009/0024189 A1 | 1/2009 | Lee et al. |
| 2009/0043185 A1 | 2/2009 | McAdams et al. |
| 2009/0056709 A1 | 3/2009 | Worsoff |
| 2009/0099600 A1 | 4/2009 | Moore et al. |
| 2009/0099623 A1 | 4/2009 | Bentwich et al. |
| 2009/0099626 A1 | 4/2009 | de Juan, Jr. et al. |
| 2009/0101139 A1 | 4/2009 | Karell |
| 2009/0124965 A1 | 5/2009 | Greenberg et al. |
| 2009/0138061 A1 | 5/2009 | Stephens et al. |
| 2009/0156581 A1 | 6/2009 | Dillon et al. |
| 2009/0157142 A1 | 6/2009 | Cauller et al. |
| 2009/0157145 A1 | 6/2009 | Cauller |
| 2009/0157147 A1 | 6/2009 | Cauller et al. |
| 2009/0192571 A1 | 7/2009 | Stett et al. |
| 2009/0204142 A1 | 8/2009 | Becker |
| 2009/0241840 A1 | 10/2009 | Mills |
| 2009/0264966 A1 | 10/2009 | Blum et al. |
| 2009/0281594 A1 | 11/2009 | King et al. |
| 2009/0281596 A1 | 11/2009 | King et al. |
| 2009/0299418 A1 | 12/2009 | Shalev et al. |
| 2009/0306738 A1 | 12/2009 | Weiss et al. |
| 2010/0030150 A1 | 2/2010 | Paques et al. |
| 2010/0076423 A1 | 3/2010 | Muller |
| 2010/0087896 A1 | 4/2010 | McCreery |
| 2010/0094280 A1 | 4/2010 | Muller |
| 2010/0139002 A1 | 6/2010 | Walker et al. |
| 2010/0152708 A1 | 6/2010 | Li et al. |
| 2010/0161004 A1 | 6/2010 | Najafi et al. |
| 2010/0168513 A1 | 7/2010 | Pless et al. |
| 2010/0179468 A1 | 7/2010 | Becker |
| 2010/0211132 A1 | 8/2010 | Nimmagadda et al. |
| 2010/0241195 A1 | 9/2010 | Meadows et al. |
| 2010/0274164 A1 | 10/2010 | Juto |
| 2010/0274224 A1 | 10/2010 | Jain et al. |
| 2010/0274313 A1 | 10/2010 | Boling et al. |
| 2010/0280509 A1 | 11/2010 | Muller et al. |
| 2010/0288275 A1 | 11/2010 | Djupesland et al. |
| 2010/0318159 A1 | 12/2010 | Aghassian et al. |
| 2011/0021975 A1 | 1/2011 | Covello |
| 2011/0028807 A1 | 2/2011 | Abreu |
| 2011/0028883 A1 | 2/2011 | Juan, Jr. et al. |
| 2011/0077551 A1 | 3/2011 | Videbaek |
| 2011/0093043 A1 | 4/2011 | Torgerson et al. |

(56) References Cited

U.S. PATENT DOCUMENTS

| | | |
|---|---|---|
| 2011/0151393 A1 | 6/2011 | Frey, II et al. |
| 2011/0152969 A1 | 6/2011 | Zehnder et al. |
| 2011/0202121 A1 | 8/2011 | Wen |
| 2011/0218590 A1 | 9/2011 | Degiorgio et al. |
| 2011/0234971 A1 | 9/2011 | Yeh |
| 2011/0275734 A1 | 11/2011 | Scales et al. |
| 2011/0276107 A1 | 11/2011 | Simon et al. |
| 2011/0282251 A1 | 11/2011 | Baker et al. |
| 2011/0295336 A1 | 12/2011 | Sharma et al. |
| 2011/0313330 A1 | 12/2011 | Loushin et al. |
| 2011/0313480 A1 | 12/2011 | De Vos |
| 2011/0313481 A1* | 12/2011 | De Vos .............. A61H 39/002 607/3 |
| 2012/0053648 A1 | 3/2012 | Neher et al. |
| 2012/0112903 A1 | 5/2012 | Kaib et al. |
| 2012/0130398 A1 | 5/2012 | Ackermann et al. |
| 2012/0197338 A1 | 8/2012 | Su et al. |
| 2012/0232615 A1 | 9/2012 | Barolat et al. |
| 2012/0232618 A1 | 9/2012 | Feldman |
| 2012/0234332 A1 | 9/2012 | Shantha |
| 2012/0253249 A1 | 10/2012 | Wilson et al. |
| 2012/0298105 A1 | 11/2012 | Osorio et al. |
| 2012/0315329 A1 | 12/2012 | Ahn et al. |
| 2012/0316557 A1 | 12/2012 | Sartor et al. |
| 2012/0323214 A1 | 12/2012 | Shantha |
| 2012/0323227 A1 | 12/2012 | Wolf et al. |
| 2012/0323232 A1 | 12/2012 | Wolf et al. |
| 2012/0330376 A1 | 12/2012 | Flynn et al. |
| 2013/0006095 A1 | 1/2013 | Jenkins et al. |
| 2013/0006326 A1 | 1/2013 | Ackermann et al. |
| 2013/0053733 A1 | 2/2013 | Korb et al. |
| 2013/0053737 A1 | 2/2013 | Scerbo |
| 2013/0065765 A1 | 3/2013 | Selifonov et al. |
| 2013/0158451 A1 | 6/2013 | Juto et al. |
| 2013/0158626 A1 | 6/2013 | DeGiorgio et al. |
| 2013/0172790 A1 | 7/2013 | Badawi |
| 2013/0178937 A1 | 7/2013 | Vassallo et al. |
| 2013/0253387 A1 | 9/2013 | Bonutti et al. |
| 2013/0261706 A1 | 10/2013 | Mirro et al. |
| 2013/0270491 A1 | 10/2013 | Park et al. |
| 2013/0274824 A1* | 10/2013 | Otto ................ A61N 1/0546 607/45 |
| 2013/0274831 A1 | 10/2013 | Otto et al. |
| 2013/0304154 A1 | 11/2013 | Goodman et al. |
| 2013/0310887 A1 | 11/2013 | Curtis |
| 2014/0012182 A1 | 1/2014 | Shantha et al. |
| 2014/0056815 A1 | 2/2014 | Peyman |
| 2014/0081353 A1 | 3/2014 | Cook et al. |
| 2014/0088463 A1 | 3/2014 | Wolf et al. |
| 2014/0163580 A1 | 6/2014 | Tischendorf et al. |
| 2014/0214120 A1* | 7/2014 | Simon ............ A61N 1/36075 607/46 |
| 2014/0257205 A1 | 9/2014 | Schaller |
| 2014/0257433 A1 | 9/2014 | Ackermann et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0316485 A1 | 10/2014 | Ackermann et al. |
| 2014/0362339 A1 | 12/2014 | Imafuku |
| 2014/0371565 A1 | 12/2014 | Glasser |
| 2014/0371812 A1 | 12/2014 | Ackermann et al. |
| 2015/0088156 A1 | 3/2015 | Ackermann et al. |
| 2015/0238754 A1 | 8/2015 | Loudin et al. |
| 2015/0335900 A1 | 11/2015 | Ackermann et al. |
| 2015/0362755 A1 | 12/2015 | Lee et al. |
| 2016/0022992 A1 | 1/2016 | Franke et al. |
| 2016/0114163 A1 | 4/2016 | Franke et al. |
| 2016/0121118 A1 | 5/2016 | Franke et al. |
| 2016/0158548 A1 | 6/2016 | Ackermann et al. |
| 2016/0270656 A1 | 9/2016 | Samec et al. |
| 2016/0367795 A1 | 12/2016 | Ackermann et al. |
| 2016/0367806 A1 | 12/2016 | Kahook |
| 2017/0049619 A1 | 2/2017 | Kahook |
| 2017/0157401 A1 | 6/2017 | Loudin et al. |
| 2017/0252563 A1 | 9/2017 | Franke et al. |
| 2017/0312521 A1 | 11/2017 | Franke et al. |
| 2017/0340884 A1 | 11/2017 | Franke et al. |
| 2017/0354536 A1 | 12/2017 | Kuzma et al. |
| 2017/0368332 A1 | 12/2017 | Ackermann et al. |
| 2017/0368359 A1 | 12/2017 | Loudin et al. |
| 2018/0064940 A1 | 3/2018 | Ackermann et al. |
| 2018/0064941 A1 | 3/2018 | Ackermann et al. |
| 2018/0064942 A1 | 3/2018 | Franke et al. |

FOREIGN PATENT DOCUMENTS

| | | |
|---|---|---|
| EM | 2102681-0001 | 10/2012 |
| EM | 2199000-0001 | 3/2013 |
| EP | 0 109 935 A1 | 5/1984 |
| EP | 1 497 483 | 1/2005 |
| EP | 1 651 307 | 5/2006 |
| EP | 1 919 553 | 5/2008 |
| EP | 1 958 661 A1 | 8/2008 |
| EP | 2 205 193 | 7/2010 |
| EP | 2 205 314 | 7/2010 |
| GB | 2 129 690 B | 3/1987 |
| GB | 2 456 002 A | 7/2009 |
| JP | S60500241 A | 2/1985 |
| JP | 2002-325851 A | 11/2002 |
| JP | 2002-539859 A | 11/2002 |
| JP | 2005-052461 A | 3/2005 |
| JP | 2005-144178 A | 6/2005 |
| JP | 2006-515900 A | 6/2006 |
| JP | 2006-311917 A | 11/2006 |
| JP | 2007-044323 A | 2/2007 |
| JP | 2007-528751 A | 10/2007 |
| JP | 2008-183248 A | 8/2008 |
| JP | 2008-541850 A | 11/2008 |
| JP | 2009-523503 A | 6/2009 |
| JP | 2010-505563 A | 2/2010 |
| JP | 2010-051562 A | 3/2010 |
| JP | 2010-537777 A | 12/2010 |
| JP | 2011-030734 A | 2/2011 |
| JP | 2011-524780 A | 9/2011 |
| WO | WO-00/56393 A1 | 9/2000 |
| WO | WO-00/62672 A1 | 10/2000 |
| WO | WO-2003/087433 A1 | 10/2003 |
| WO | WO-2004/026106 A2 | 4/2004 |
| WO | WO-2004/026106 A3 | 4/2004 |
| WO | WO-2004/043217 A2 | 5/2004 |
| WO | WO-2004/043217 A3 | 5/2004 |
| WO | WO-2004/091453 A1 | 10/2004 |
| WO | WO-2004/112893 A2 | 12/2004 |
| WO | WO-2004/112893 A3 | 12/2004 |
| WO | WO-2005/007234 A2 | 1/2005 |
| WO | WO-2005/007234 A3 | 1/2005 |
| WO | WO-2005/030025 A2 | 4/2005 |
| WO | WO-2005/030025 A3 | 4/2005 |
| WO | WO-2005/060984 A1 | 7/2005 |
| WO | WO-2006/127366 A1 | 11/2006 |
| WO | WO-2007/079543 A1 | 7/2007 |
| WO | WO-2008/156501 A2 | 12/2008 |
| WO | WO-2008/156501 A3 | 12/2008 |
| WO | WO-2009/035571 A2 | 3/2009 |
| WO | WO-2009/035571 A3 | 3/2009 |
| WO | WO-2009/048580 A1 | 4/2009 |
| WO | WO-2009/070709 A1 | 6/2009 |
| WO | WO-2009/154457 A2 | 12/2009 |
| WO | WO-2010/003011 A1 | 1/2010 |
| WO | WO-2010/027743 A1 | 3/2010 |
| WO | WO-2010/099818 A1 | 9/2010 |
| WO | WO-2011/011373 A1 | 1/2011 |
| WO | WO-2012/068247 A1 | 5/2012 |
| WO | WO-2012/139063 A2 | 10/2012 |
| WO | WO-2012/139063 A3 | 10/2012 |
| WO | WO-2012/155188 A1 | 11/2012 |
| WO | WO-2013/055940 A2 | 4/2013 |
| WO | WO-2013/055940 A3 | 4/2013 |
| WO | WO-2013/157320 A1 | 10/2013 |
| WO | WO-2013/165697 A1 | 11/2013 |
| WO | WO-2013/166353 A1 | 11/2013 |
| WO | WO-2014/138709 A1 | 9/2014 |
| WO | WO-2014/165124 A1 | 10/2014 |
| WO | WO-2014/172693 A2 | 10/2014 |

(56) References Cited

FOREIGN PATENT DOCUMENTS

| WO | WO-2014/172693 A3 | 10/2014 |
|----|-------------------|---------|
| WO | WO-2015/130707 A2 | 9/2015  |
| WO | WO-2015/130707 A3 | 9/2015  |
| WO | WO-2016/015025 A1 | 1/2016  |
| WO | WO-2016/065211 A1 | 4/2016  |
| WO | WO-2016/065213 A1 | 4/2016  |
| WO | WO-2016/065215 A1 | 4/2016  |

OTHER PUBLICATIONS

Amparo (2013). "Topical Interleukin 1 Receptor Antagonist for Treatment of Dry Eye Disease," JAMA Ophth. 131(6):E1-E9.
Anonymous (2007). "The epidemiology of dry eye disease: report of the Epidemiology Subcommittee of the International Dry Eye WorkShop (2007)," Ocul. Surf. 5(2):93-107.
Bajpai et al. (2012). "Preparation, Characterization and Water Uptake Behavior of Polysaccharide Based Nanoparticles," Prog. Nanotech. Nanomat. 1(1):9-17.
Baraniuk et al. (2007). "Nasonasal Reflexes, the Nasal Cycle, and Sneeze," Curr. Allergy and Asthma Reports 7:105-111.
Baroody FM, Foster KA, Markaryan A, et al. Nasal ocular reflexes and eye symptoms in patients with allergic rhinitis. Ann Allergy Asthma Immunol 2008;100:194-199.
Baroody FM, Shenaq D, DeTineo M, et al. Fluticasone furoate nasal spray reduces the nasal-ocular reflex: a mechanism for the efficacy of topical steroids in controlling allergic eye symptoms. J Allergy Clin Immunol 2009;123:1342-1348.
Boberg-Ans J. (1955). "Experience in clinical examination of corneal sensitivity: corneal sensitivity and the naso-lacrimal reflex after retrobulbar anaesthesia," Br. J. Ophthalmol. 39(12):705-726.
Calonge (2001). "The Treatment of Dry Eye," Survey Ophth. 45(2):S227-S239.
Cipriano et al. (2014). "Superabsorbent Hydrogels That Are Robust and Highly Stretchable," Am. Chem Soc. 47(13):4445-4452.
Corrected Notice of Allowance dated Feb. 23, 2015, for U.S. Appl. No. 14/256,915, filed Apr. 18, 2014, 2 pages.
Corrected Notice of Allowance dated Jun. 9, 2017, for U.S. Appl. No. 14/920,860, filed Oct. 22, 2015, 2 pages.
Dart et al. (2002). "Effects of 25% Propylene Glycol Hydrogel (Solugel) on Second Intention Wound Healing in Horses," Vet. Surg. 31(4):309-313.
Drummond PD. Lacrimation and cutaneous vasodilatation in the face induced by painful stimulation of the nasal ala and upper lip. J Auton Nerv Syst 1995;51:109-16.
Elsby et al. (1967). "Lacrimal Secretion in the Cat," Br. J. Pharm. Chemother. 29(1):1-7.
Extended European Search Report dated Nov. 18, 2016, for EP Application No. 14 785 631.4, filed on Apr. 18, 2014, 7 pages.
Final Office Action received for U.S. Appl. No. 14/256,916, dated Apr. 8, 2015, 16 pages.
Final Office Action received for U.S. Appl. No. 14/313,937 dated Apr. 29, 2015, 13 pages.
Final Office Action received for U.S. Appl. No. 14/630,471, dated Sep. 26, 2016, 22 pages.
Final Office Action received for U.S. Appl. No. 14/256,916, dated Aug. 19, 2016, 19 pages.
Final Office Action dated Sep. 23, 2016, for U.S. Appl. No. 14/809,109, filed Jul. 24, 2015, 10 pages.
Final Office Action dated Feb. 1, 2017, for U.S. Appl. No. 14/920,852, filed Oct. 22, 2015, 20 pages.
Fujisawa et al. (2002). "The Effect of Nasal Mucosal Stimulation on Schirmer Tests in Sjogren's Syndrome and Dry Eye Patients," Lac. Gland Tear Film Dry Eye Syndrome 3 506:1221-1226.
Gupta et al. (1997). "Nasolacrimal Stimulation of Aqueous Tear Production," Cornea 16(6):645-648.
Heigle TJ, Pflugfelder SC. Aqueous tear production in patients with neurotrophic keratitis. Cornea 1996;15:135-8.

Holzer P. Capsaicin: cellular targets, mechanisms of action, and selectivity for thin sensory neurons. Pharmacol Rev 1991;43:143-201.
Ikemura et al. (2008). "UV-VIS Spectra and Photoinitiation Behaviors of Acylphosphine Oxide and Bisacylphosphine Oxide Derivatives in unfilled, Light-Cured Dental Resins," Dental Mat. J. 27(6):765-774.
International Preliminary Report on Patentability received for PCT Patent Application No. PCT/US2014/034733, dated Oct. 29, 2015.
International Search Report and Written Opinion received for PCT Application No. PCT/US2015/042130, dated Oct. 28, 2015.
International Search Report and Written Opinion received for PCT Patent Application No. PCT/US2014/034733, dated Dec. 5, 2014.
International Search Report and Written Opinion received for PCT Patent Application No. PCT/US2015/017379, dated Jul. 24, 2015.
International Search Report and Written Opinion received for PCT Patent Application No. PCT/US2015/057023, dated Mar. 4, 2016.
International Search Report dated Feb. 10, 2016, for PCT Patent Application No. PCT/US2015/57021, filed on Oct. 22, 2015, 4 pages.
Krupin T, Cross DA, Becker B. Decreased basal tear production associated with general anesthesia. Arch Ophthalmol 1977;95:107-108.
Lora et al. (2009). "Lacrimal Nerve Stimulation by a Neurostimulator for Tear Production," Invest. Ophth. Vis. Science 50(13):172.
Loth S, Bende M. Effect of nasal anaesthesia on lacrimal function after nasal allergen challenge. Clin Exp Allergy 1994;24:375-376.
Meng, I.D. et al. (2013). "The role of corneal afferent neurons in regulating tears under normal and dry eye conditions," Exp. Eye Res. 117:79-87.
Mallepally et al. (2013). "Superabsorbent Alginate Aerogels," J. Supercritical Fluids 79:1-5.
Non-Final Office Action received for U.S. Appl. No. 14/256,915, dated Aug. 13, 2014, 11 pages.
Non-Final Office Action received for U.S. Appl. No. 14/256,916, dated Sep. 12, 2014, 24 pages.
Non-Final Office Action received for U.S. Appl. No. 14/313,937, dated Nov. 19, 2014, 12 pages.
Non-Final Office Action dated Jun. 14, 2016, for U.S. Appl. No. 14/630,471, filed Feb. 24, 2015, 24 pages.
Non-Final Office Action received for U.S. Appl. No. 14/809,109, dated Apr. 8, 2016, 8 pages.
Non-Final Office Action Received for U.S. Appl. No. 14/920,860, dated Aug. 17, 2016, 11 pages.
Non-Final Office Action received for U.S. Appl. No. 14/256,916, dated Nov. 19, 2015, 20 pages.
Non-Final Office Action Received for U.S. Appl. No. 14/313,937, dated Oct. 6, 2015, 7 pages.
Non-Final Office Action Received for U.S. Appl. No. 14/920,852, dated Aug. 1, 2016, 20 pages.
Non-Final Office Action dated Sep. 30, 2016, for U.S. Appl. No. 15/256,392, filed Sep. 2, 2016, 14 pages.
Non-Final Office Action dated Feb. 14, 2017, for U.S. Appl. No. 14/630,471, filed Feb. 24, 2015, 23 pages.
Non-Final Office Action dated Apr. 19, 2017, for U.S. Appl. No. 14/256,916, filed Apr. 18, 2014, 19 pages.
Notice of Allowance received for U.S. Appl. No. 14/256,915, dated Nov. 26, 2014, 7 pages.
Notice of Allowance received for U.S. Appl. No. 14/313,937, dated Feb. 19, 2016, 8 pages.
Notice of Allowance received for U.S. Appl. No. 14/313,937, dated May 2, 2016, 7 pages.
Notice of Allowability dated Dec. 19, 2016, for U.S. Appl. No. 14/809,109, filed Jul. 24, 2015, 8 pages.
Notice of Allowance dated Jan. 19, 2017, for U.S. Appl. No. 14/920,860, filed Oct. 22, 2015, 5 pages.
Notice of Allowance dated Mar. 21, 2017, for U.S. Appl. No. 14/809,109, filed Jul. 24, 2015, 8 pages.
Notice of Allowance dated Apr. 17, 2017, for U.S. Appl. No. 15/256,392, filed Sep. 2, 2016, 10 pages.
Notice of Allowance dated Apr. 20, 2017, for U.S. Appl. No. 14/920,860, filed Oct. 22, 2015, 5 pages.

(56) References Cited

OTHER PUBLICATIONS

Notice of Allowance dated May 26, 2017, for U.S. Appl. No. 14/630,471, filed Feb. 24, 2015, 5 pages.
Pasqui et al. (2012). "Polysaccharide-Based Hydrogels: The Key Role of Water in Affecting Mechanical Properties," Polymers 4(3):1517-1534.
Philip G, Baroody FM, Proud D, et al. The human nasal response to capsaicin. J Allergy Clin Immunol 1994;94:1035-1045.
Roessler et al. (2009). "Implantation and Explantation of a Wireless Epiretinal Retina Implant Device: Observations During the EPIRET3 Prospective Clinical Trial," Invest. Ophthal. Visual Science 50(6):3003-3008.
Ruskell (2004). "Distribution of Pterygopalatine Ganglion Efferents to the Lacrimal Gland in Man," Exp. Eye Res. 78(3):329-335.
Sall et al. (2000). "Two Multicenter, Randomized Studies of the Efficacy and Safety of Cyclosporine Ophthalmic Emulsion in Moderate to Severe Dry Eye Disease," Ophth. 107(4):631-639.
Shaari et al. (1995). "Rhinorrhea is decreased in dogs after nasal application of botulinum toxin," Oto. Head Neck Surg. 112(4):566-571.
Stjernschantz et al. (1979). "Electrical Stimulation of the Fifth Cranial Nerve in Rabbits: Effects on Ocular Blood Flow, Extravascular Albumin Content and Intraocular Pressure," Exp. Eye Res. 28(2):229-238.
Stjernschantz et al. (1980). "Vasomotor effects of Facial Nerve Stimulation: Noncholinergic Vasodilation in the eye," Acta Phys. Scand. 109(1):45-50.
Tsubota (1991). "The Importance of the Schirmer Test with Nasal Stimulation," Am. J. Ophth. 111:106-108.
Velikay-Parel et al. (2011). "Perceptual Threshold and Neuronal Excitability as Long-Term Safety Evaluation in Retinal Implants," Invest. Opht. Visual Science E-Abstract 2590, 2 pages.
Written Opinion received for PCT Patent Application No. PCT/US2015/57021, dated Feb. 10, 2016, 5 pages.
Zilstorff-Pedersen (1965). "Quantitative Measurements of the Nasolacrimal Reflex," Arch. Oto. 81:457-462.
Eye Health (2014). "Watery eyes in cold weather," Oregon Eye Specialists, PC, located at http://www.oregoneyes.net/watery-eyes-in-cold-weather/, 3 total pages.
Friedman et al. (2016). "A nonrandomized, open-label study to evaluate the effect of nasal stimulation on tear production in subjects with dry eye disease," Clin. Ophthal. 10:795-804.
Galor, A. et al. (2014). "Environmental factors affect the risk of dry eye syndrome in a United States veteran population," Opth. 121:972-973.
Harvard Health Publishing (2010). "Dry eyes and what you can try," Harvard Medical School, 2 total pages.
Petrov, A. et al. (2016). "SkQ1 Ophthalmic Solution for Dry Eye Treatment: Results of a Phase 2 Safety and Efficacy Clinical Study in the Environment and During Challenge in the Controlled Adverse Environment Model," Adv. Ther. 33:96-115.
van Setten, G. et al. (2016). "Evidence of seasonality and effects of psychrometry in dry eye disease," Acta Opth. 94:499-506.
Vapor Pressure Data for H2O (2012). Handbook of Chemistry and Physics, 73rd edition, 1 total page.

\* cited by examiner

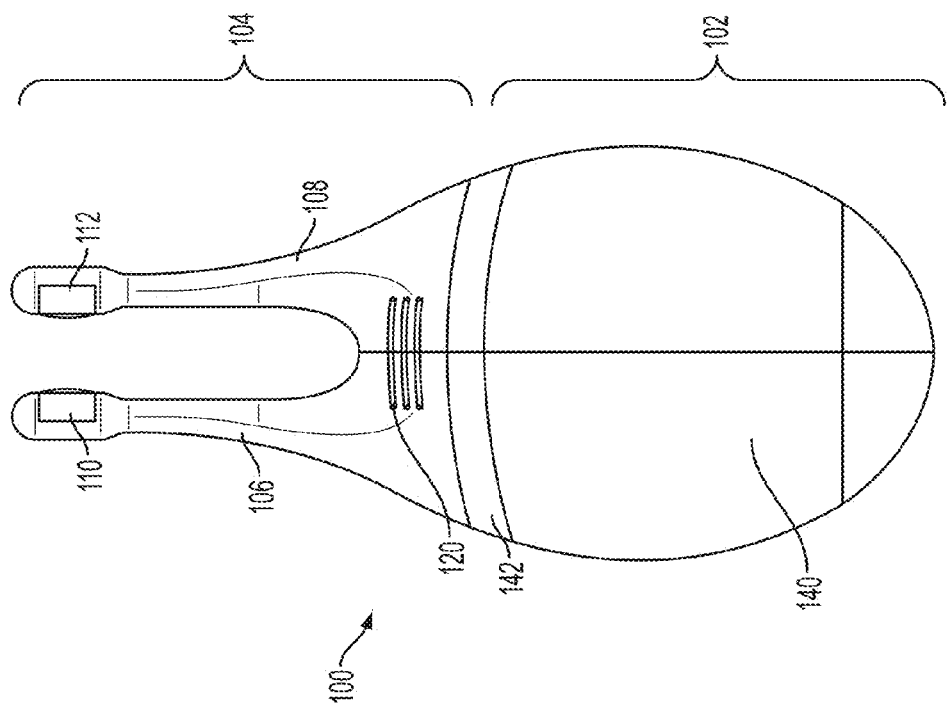
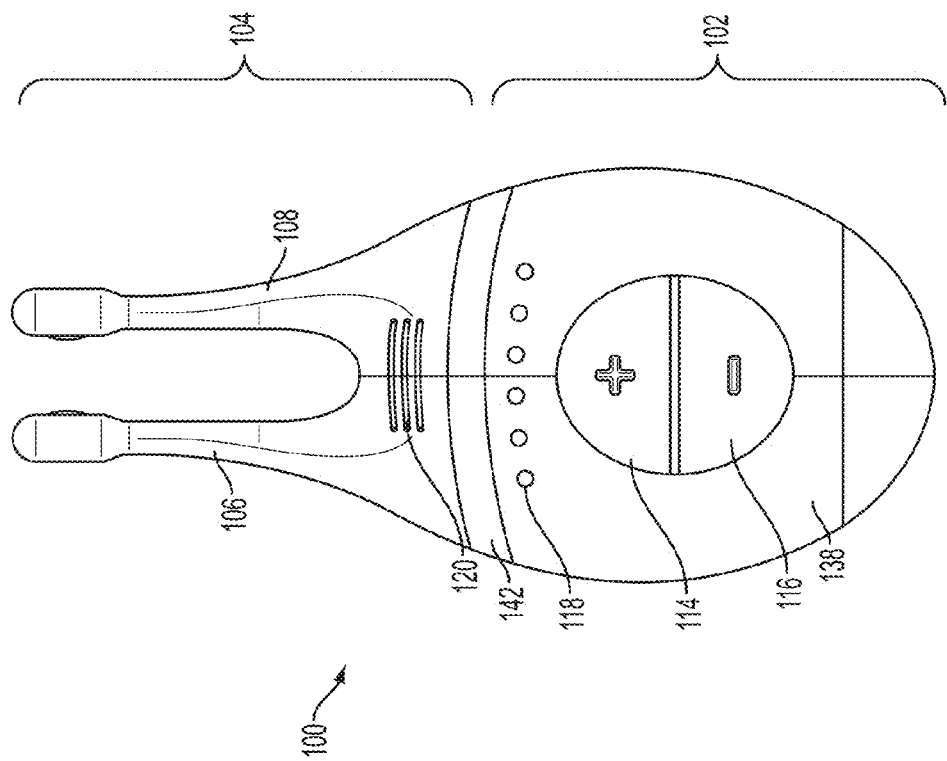

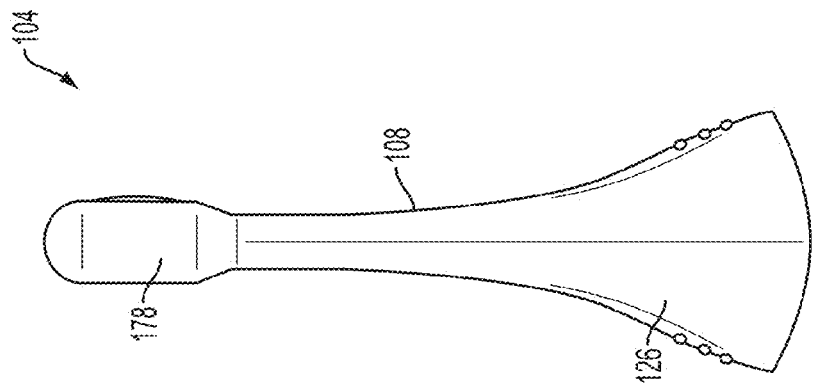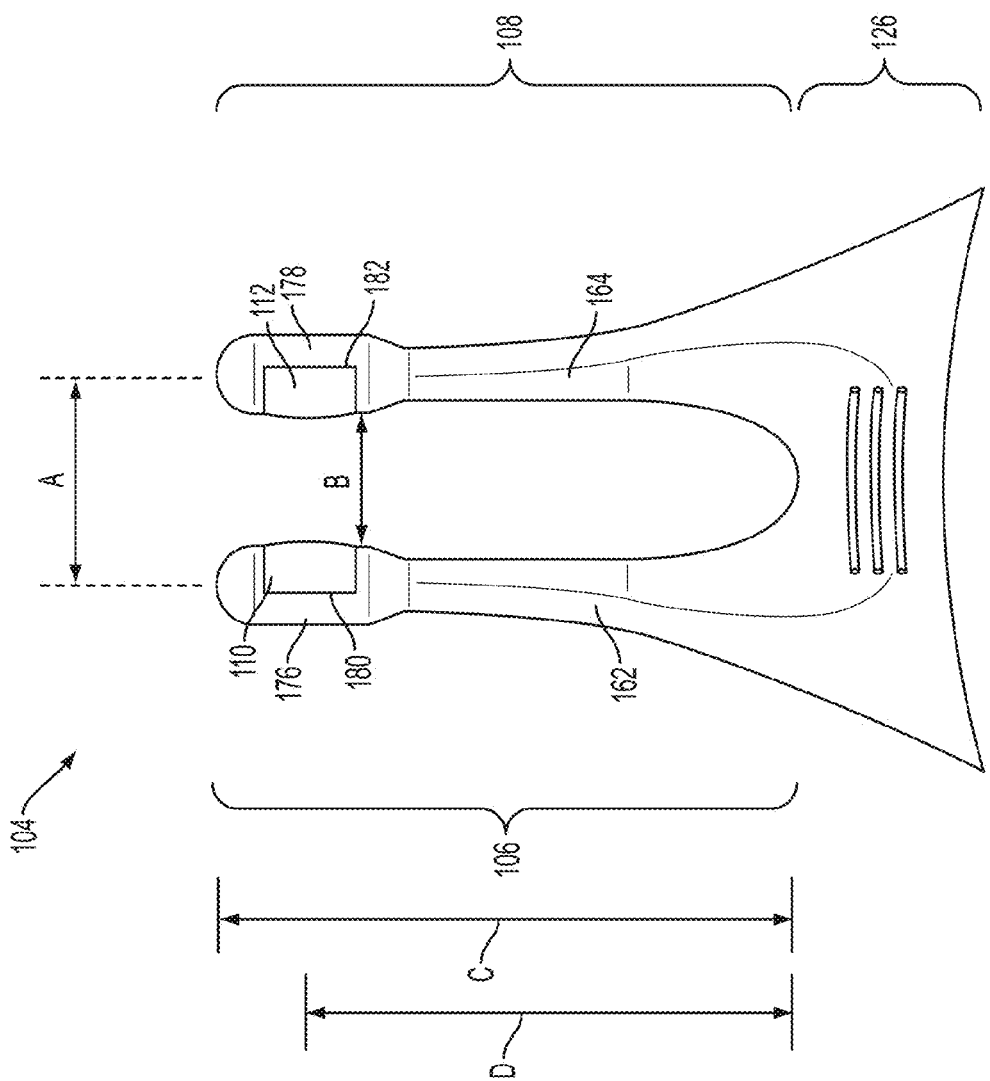
FIG. 5B
FIG. 5A

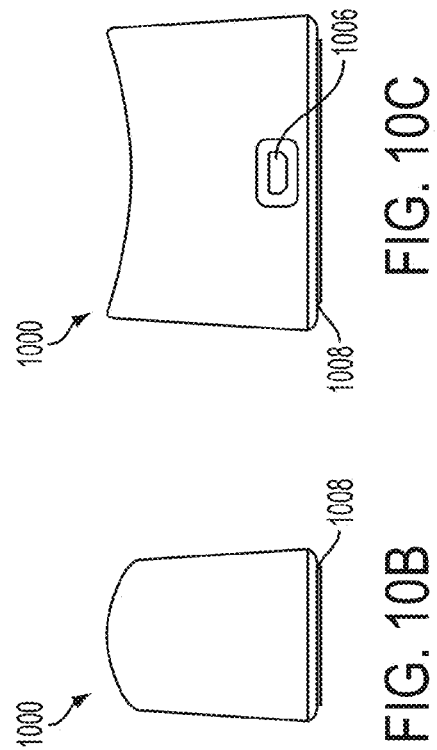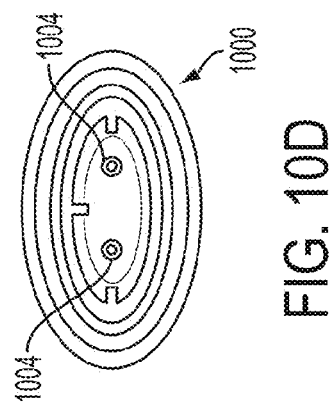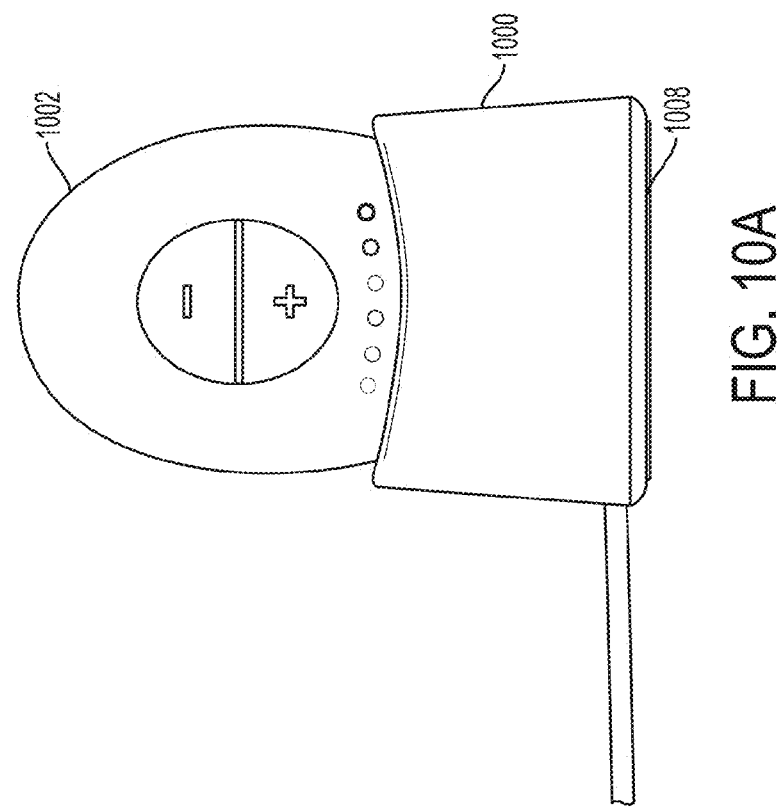
FIG. 10C
FIG. 10D
FIG. 10B
FIG. 10A

NASAL STIMULATION FOR RHINITIS, NASAL CONGESTION, AND OCULAR ALLERGIES

CROSS-REFERENCE TO RELATED APPLICATIONS

This application claims priority to U.S. Provisional Application No. 62/297,734, filed Feb. 19, 2016, and titled "NASAL STIMULATION FOR RHINITIS, NASAL CONGESTION, AND OCULAR ALLERGIES," which is hereby incorporated by reference in its entirety.

FIELD

Described herein are methods for treating allergic rhinitis, non-allergic rhinitis, nasal congestion, ocular allergy, and/or symptoms associated with these conditions by delivering an electrical stimulus.

BACKGROUND

Patients with allergic and non-allergic rhinitis and nasal congestion often suffer from inflammation of the nasal membranes that can cause numerous symptoms and complications. These same patients may frequently also suffer from other types of allergies and immunoglobulin E (IgE)-mediated disorders, including ocular allergies. Typical treatments may include pharmacologic therapy, such as intranasal steroids, oral antihistamines, and anti-IgE for allergic rhinitis. However, it would be desirable to have a non-pharmacologic, non-invasive treatment for these conditions for use alone or in combination with pharmacologic therapy.

Allergic rhinitis in particular is an IgE-mediated inflammatory nasal disorder that involves hyperactive nasal mucosa, obstruction of the nasal passages, and symptoms of rhinorrhea, sneezing, nasal pruritus, and congestion. Allergic rhinitis is also commonly associated with conjunctivitis, itchy palate, and aggravation of comorbid asthma. Traditionally, allergic rhinitis has been classified as perennial, with symptoms occurring year round, or seasonal, with symptoms occurring at particular times of the year. Perennial symptoms are most commonly associated with dust mites, cockroaches, and molds, whereas seasonal symptoms may be induced by pollens.

Allergic rhinitis currently affects 10% to 25% of the population worldwide, and 20 to 40 million people in the United States annually, including 10% to 30% of adults and up to 40% of children. Furthermore, incidence of allergic rhinitis seems to be increasing globally. The management of allergic rhinitis remains challenging because of the side effects of existing medication classes and because of their variable effectiveness. The latter reflects the variable nature of allergic rhinitis in the general population. There is therefore an unmet need for a safe and effective non-pharmacological method for treating allergic rhinitis.

BRIEF SUMMARY

Described herein are methods for treating rhinitis (allergic rhinitis, non-allergic rhinitis), nasal congestion, runny nose, ocular allergy, and/or symptoms associated with these conditions. Some methods for treating rhinitis described herein may comprise delivering an electrical stimulus via an electrode to treat rhinitis in a patient in need thereof. The rhinitis may be allergic rhinitis or non-allergic rhinitis. The electrode may be in contact with nasal tissue of the patient during delivery of the electrical stimulus. In some variations, the electrical stimulus is delivered in response to one or more symptoms of rhinitis. The one or more symptoms of rhinitis may comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation. In other variations of the method, the electrical stimulus is delivered more than once per day on a scheduled basis. In some variations of a method for treating rhinitis, the nasal tissue to which the electrical stimulus is delivered is nasal mucosa. The nasal mucosa may be adjacent to the nasal septum. In some variations of the method, the electrode may be a hydrogel electrode. The electrode may be electrically connected to a control subsystem configured to control the electrical stimulus delivered via the electrode. The electrode may be positioned on a stimulator probe and the control subsystem is positioned in a stimulator body, and the stimulator probe may be releasably connected to the stimulator body. The electrical stimulus may be a biphasic pulse waveform.

Also described here are methods for treating rhinitis, comprising delivering an electrical stimulus to nasal tissue of a subject to improve rhinitis of the subject, where the electrical stimulus is delivered by an electrode of a stimulator comprising a control subsystem to control the electrical stimulus. The rhinitis may be allergic rhinitis or non-allergic rhinitis. In some variations, the electrical stimulus may be delivered in response to one or more symptoms of rhinitis. The one or more symptoms of rhinitis may comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation. In some variations, the electrical stimulus is pulsed. In some variations of the method, the electrical stimulus may be delivered at least once daily during a treatment period. The electrical stimulus may be delivered on a scheduled basis during the treatment period. In some variations, the electrical stimulus may be a biphasic pulse waveform. The biphasic pulse waveform may be symmetrical, may have varying peak to peak amplitude, and/or may have a varying frequency. In some variations of the method, the stimulator may be configured to be hand held. In some variations, delivering the electrical stimulus to nasal tissue may activate the ophthalmic branch of the trigeminal nerve. In some variations, delivering the electrical stimulus may activate the anterior ethmoidal nerve. In some variations, delivering the electrical stimulus may activate the internal branches of the infraorbital nerve. In some variations, delivering the electrical stimulus may activate the superior branches of the greater palatine nerve. In some variations, delivering the electrical stimulus may activate the septal nerve. In some variations, delivering the electrical stimulus may activate the posterior superior lateral nasal branch of the maxillary nerve.

Also described here are methods for treating nasal congestion, comprising delivering an electrical stimulus via an electrode to treat nasal congestion in a patient in need thereof. The electrode may be in contact with nasal tissue of the patient during delivery of the electrical stimulus. In some variations, the electrical stimulus may be delivered in response to one or more symptoms of nasal congestion. The one or more symptoms of nasal congestion may comprise difficulty with nasal breathing, ear fullness, facial pain, and/or facial and intracranial pressure. In other variations, the electrical stimulus is delivered more than once per day on a scheduled basis. The nasal tissue may be nasal mucosa, which in some instances may be adjacent to the nasal septum. The electrode in contact with the tissue may be a hydrogel electrode. The electrode may be electrically connected to a control subsystem configured to control the electrical stimulus delivered via the electrode. The electrode may be positioned on a stimulator probe and the control subsystem is positioned in a stimulator body, and the stimulator probe may be releasably connected to the stimulator body. In some variations, the electrical stimulus may be a biphasic pulse waveform.

Also described here are methods for treating nasal congestion comprising delivering an electrical stimulus to nasal tissue of a subject to improve nasal congestion of the subject, wherein the electrical stimulus is delivered by an electrode of a stimulator comprising a control subsystem to control the electrical stimulus. The electrical stimulus may be delivered in response to one or more symptoms of nasal congestion. The one or more symptoms of nasal congestion may comprise difficulty with nasal breathing, ear fullness, facial pain, and/or facial and intracranial pressure. In other variations, the electrical stimulus may be delivered at least once daily during a treatment period. In some of these variations, the electrical stimulus may be delivered on a scheduled basis during the treatment period. In some variations of the method, the electrical stimulus is pulsed. The electrical stimulus may be a biphasic pulse waveform. The biphasic pulse waveform may be symmetrical, may have varying peak to peak amplitude, and/or may have a varying frequency. In some variations of the method, the stimulator may be configured to be hand held. In some variations, delivering the electrical stimulus to nasal tissue may activate the ophthalmic branch of the trigeminal nerve. In some variations, delivering the electrical stimulus may activate the anterior ethmoidal nerve. In some variations, delivering the electrical stimulus may activate the internal branches of the infraorbital nerve. In some variations, delivering the electrical stimulus may activate the superior branches of the greater palatine nerve. In some variations, delivering the electrical stimulus may activate the septal nerve. In some variations, delivering the electrical stimulus may activate the posterior superior lateral nasal branch of the maxillary nerve.

Also described here are methods for treating ocular allergy comprising delivering an electrical stimulus via an electrode to treat ocular allergy in a patient in need thereof. The electrode may be in contact with nasal tissue of the patient during delivery of the electrical stimulus. In some variations of the method, the electrical stimulus is delivered in response to one or more symptoms of ocular allergy. The one or more symptoms of ocular allergy may comprise one or more of swelling, puffiness, itching, tearing, and discharge. In other variations, the electrical stimulus is delivered more than once per day on a scheduled basis. The nasal tissue may be nasal mucosa, which in some instances may be adjacent to the nasal septum. The electrode in contact with the tissue may be a hydrogel electrode. The electrode may be electrically connected to a control subsystem configured to control the electrical stimulus delivered via the electrode. The electrode may be positioned on a stimulator probe and the control subsystem is positioned in a stimulator body, and the stimulator probe may be releasably connected to the stimulator body. In some variations, the electrical stimulus may be a biphasic pulse waveform.

Also described here are methods for treating ocular allergy comprising delivering an electrical stimulus to nasal tissue of a subject to improve ocular allergy of the subject, where the electrical stimulus is delivered by an electrode of a stimulator comprising a control subsystem to control the electrical stimulus. The electrical stimulus may be delivered in response to one or more symptoms of ocular allergy. The one or more symptoms of ocular allergy may comprise one or more of swelling, puffiness, itching, tearing, and discharge. In other variations, the electrical stimulus may be delivered at least once daily during a treatment period. In some of these variations, the electrical stimulus may be delivered on a scheduled basis during the treatment period. In some variations of the method, the electrical stimulus is pulsed. The electrical stimulus may be a biphasic pulse waveform. The biphasic pulse waveform may be symmetrical, may have varying peak to peak amplitude, and/or may have a varying frequency. In some variations of the method, the stimulator may be configured to be hand held. In some variations, delivering the electrical stimulus to nasal tissue may activate the ophthalmic branch of the trigeminal nerve. In some variations, delivering the electrical stimulus may activate the anterior ethmoidal nerve. In some variations, delivering the electrical stimulus may activate the internal branches of the infraorbital nerve. In some variations, delivering the electrical stimulus may activate the superior branches of the greater palatine nerve. In some variations, delivering the electrical stimulus may activate the septal nerve. In some variations, delivering the electrical stimulus may activate the posterior superior lateral nasal branch of the maxillary nerve.

Also described here are methods of treatment comprising delivering an electrical stimulus via an electrode to treat allergic rhinitis in a patient in need thereof. The electrode may be in contact with nasal tissue of the patient during delivery of the electrical stimulus. In some variations, the electrical stimulus delivery may treat allergic rhinitis as determined by a reduction in a symptom of allergic rhinitis. Such symptoms may include nasal itching, nasal congestion, rhinorrhea, or sneezing. In other variations, the electrical stimulus may treat allergic rhinitis as determined by a reduction in nasal inflammation; as determined by an increase in peak nasal inspiratory flow; as determined by an initial transient increase in nasal secretions, followed by a reduction in nasal secretions; as determined by normalization in temperature of a nasal area; or as determined by a decrease in fractional exhaled nitric oxide. In some variations, the method may further comprise expelling accumulated material in the nasal passageways.

BRIEF DESCRIPTION OF THE DRAWINGS

FIGS. 1A, 1B, 1C, 1D, 1E show perspective, front, back, cut-away back, and cut-away side views, respectively, of an illustrative variation of a handheld stimulator.

FIGS. 5A, 5B, 5C, 5D, and FIGS. 5E-5F depict back, side, cut-away back, cut-away top, and perspective views, respectively, of a stimulator probe suitable for the handheld stimulators described here.

FIGS. 10A-10D depict portions of a stimulator system comprising a stimulator and a base station. FIG. 10A shows a front view of the stimulator body docked in the base station, while FIGS. 10B, 10C, and 10D depict side, back, and top views, respectively, of the base station.

DETAILED DESCRIPTION OF THE INVENTION

Described here are devices, systems, and methods for treating one or more conditions, including rhinitis, nasal congestion, ocular allergy, and/or symptoms associated with these conditions. Generally, the devices and systems may be configured to stimulate nasal or sinus tissue.

Devices

Figure 1A:
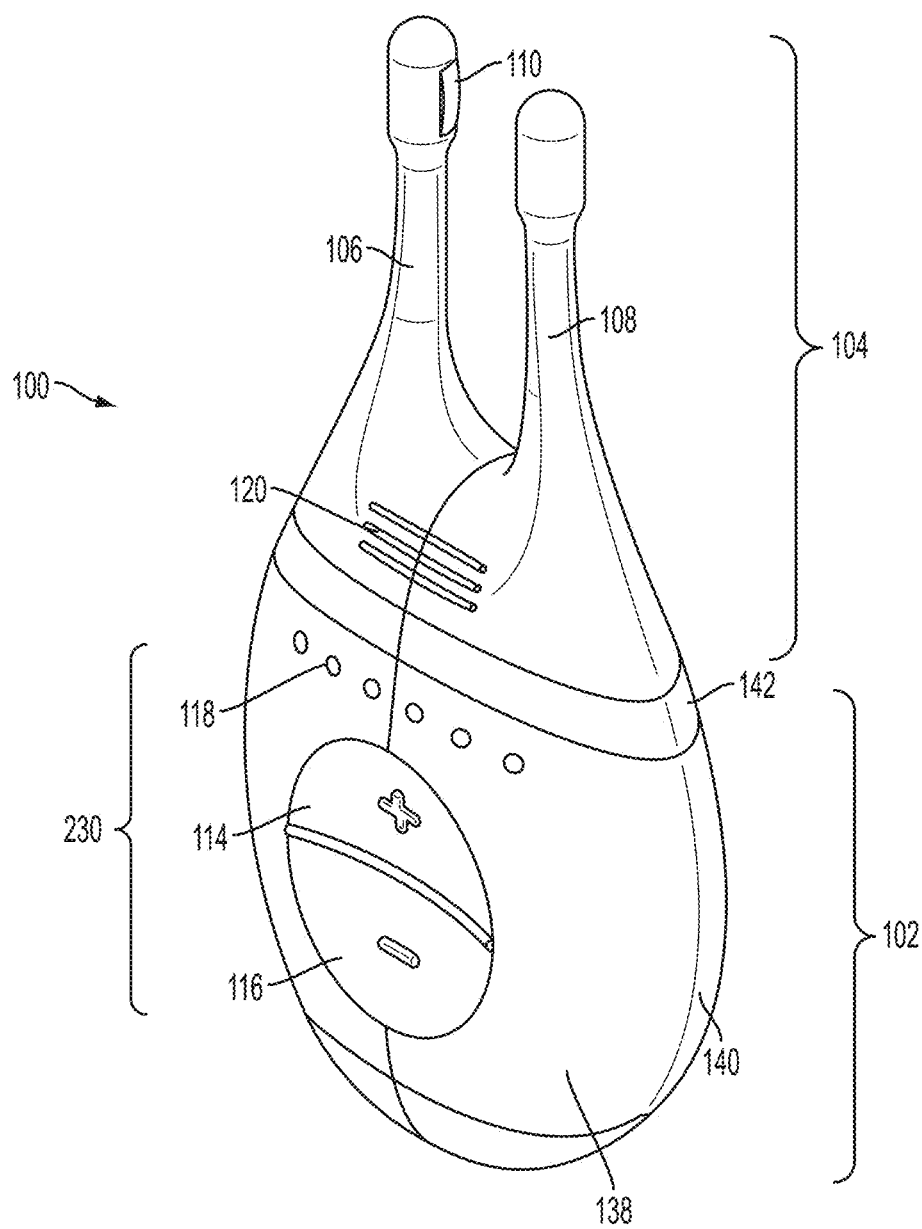
Figure 1E:
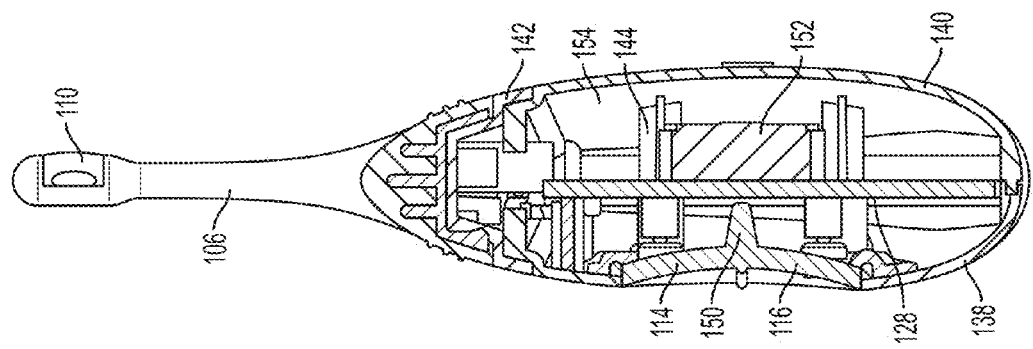

The stimulation described herein may in some variations be delivered by a handheld stimulator configured to deliver an electrical stimulus to nasal tissue. In some variations, the devices may comprise a stimulator body and a stimulator probe, where the stimulator probe comprises one or more nasal insertion prongs. FIGS. 1A, 1B, 1C, 1D, 1E show perspective, front, back, cut-away back, and cut-away side views, respectively, of an illustrative variation of a handheld stimulator 100, respectively. FIG. 2 shows a block diagram schematically representing the stimulator 100. As shown in FIGS. 1A-1E, the stimulator 100 may comprise a stimulator body 102 and a stimulator probe 104. Generally, the stimulator body 102 may be configured to generate a stimulus that may be delivered to the subject. The stimulator body 102 may comprise a front housing 138, back housing 140, and proximal housing 142, which may fit together to define a body cavity 154. The body cavity 154 may contain a control subsystem 136 and a power source 152, which together may generate and control the stimulus.

The stimulus may be delivered to a subject via the stimulator probe 104. In some variations the stimulator body 102 and stimulator probe 104 may be reversibly attachable, as described in more detail herein. In other variations, the stimulator probe may be permanently connected to the stimulator body. Some or all of the stimulator 100 may be disposable. In variations where the stimulator body is permanently attached to the stimulator probe, the entire stimulator may be disposable. In other variations, one or more portions of the stimulator 100 may be reusable. For example, in variations where the stimulator probe 104 is releasably connected to the stimulator body 102, the stimulator body 102 may be reusable, and the stimulator probe 104 may be disposable and periodically replaced, as described in more detail herein.

The stimulator probe 104 may comprise at least one nasal insertion prong, which may be configured to be at least partially inserted into the nasal cavity of a subject or patient. In the handheld stimulator variation shown in FIGS. 1A-1E, the stimulator probe 104 may comprise two nasal insertion prongs 106 and 108. The stimulator probe 104 may further comprise ridges 120, which may allow the patient to more easily grip the probe 104.

In some variations, the stimulus may be electrical. In these instances, each nasal insertion prong may comprise at least one electrode. As shown, the probe 104 may comprise a first electrode 110 on nasal insertion prong 106 and a second electrode 112 on nasal insertion prong 108. As shown in the cut-away view of the stimulator 100 in FIG. 1D, the electrodes 110 and 112 may be connected to leads 130 and 132 located within prongs 106 and 108, respectively. The leads 130 and 132 may in turn be connected to connectors 122 and 124, respectively. Connectors 122 and 124 may extend through lumens 208 and 210 in the proximal housing 142, and may connect directly or indirectly to the control subsystem 136 and power source 152. As such, the electrical stimulus may travel from the control subsystem 136 through the connectors 122 and 124, through the leads 130 and 132, and through the electrodes 110 and 112.

The stimulator body 102 may comprise a user interface 230 comprising one or more operating mechanisms to adjust one or more parameters of the stimulus, as described in more detail herein. The operating mechanisms may provide information to the control subsystem 136, which may comprise a processor 232, memory 234, and/or stimulation subsystem 236. In some variations, the operating mechanisms may comprise first and second buttons 114 and 116. In some variations, pressing the first button 114 may turn on the stimulator and/or change one or more parameters of the stimulus (e.g., increase the intensity of the stimulus, change the stimulation pattern, or the like), while pressing the second button 116 may turn off the stimulator and/or change one or more parameters of the stimulus (e.g., decrease the intensity of the stimulus, change the stimulation pattern, or the like). Additionally or alternatively, the user interface may comprise one or more feedback elements (e.g., based on light, sound, vibration, or the like). As shown, the user feedback elements may comprise light-based indicators 118, which may provide information to the user, as described in more detail herein.

Stimulator Body

Figure 3A:
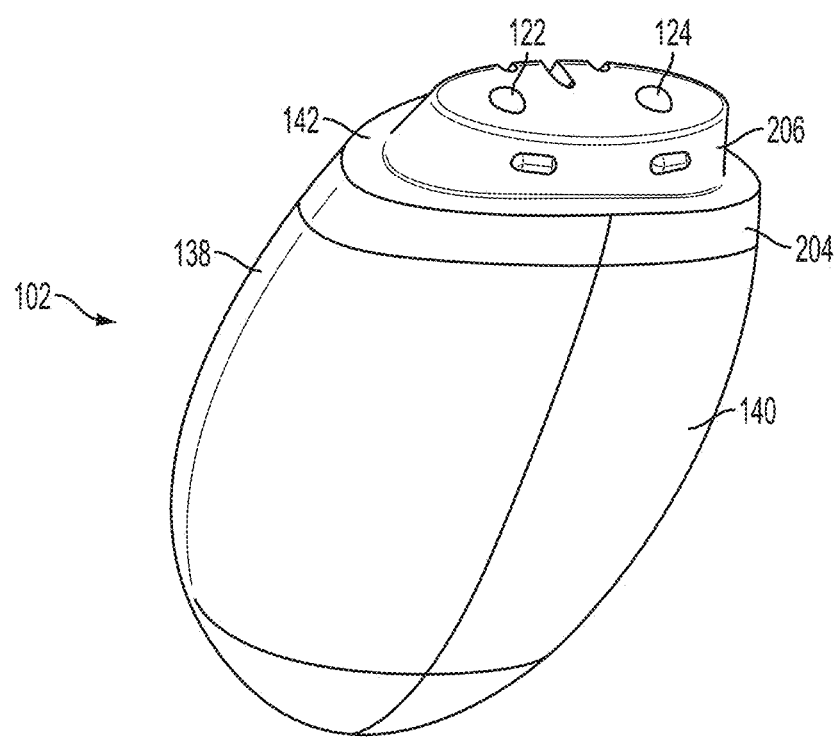
FIG. 3A and FIGS. 3B-3C show perspective and exploded views, respectively, of a stimulator body suitable for the handheld stimulators described here.
Figure 3B:
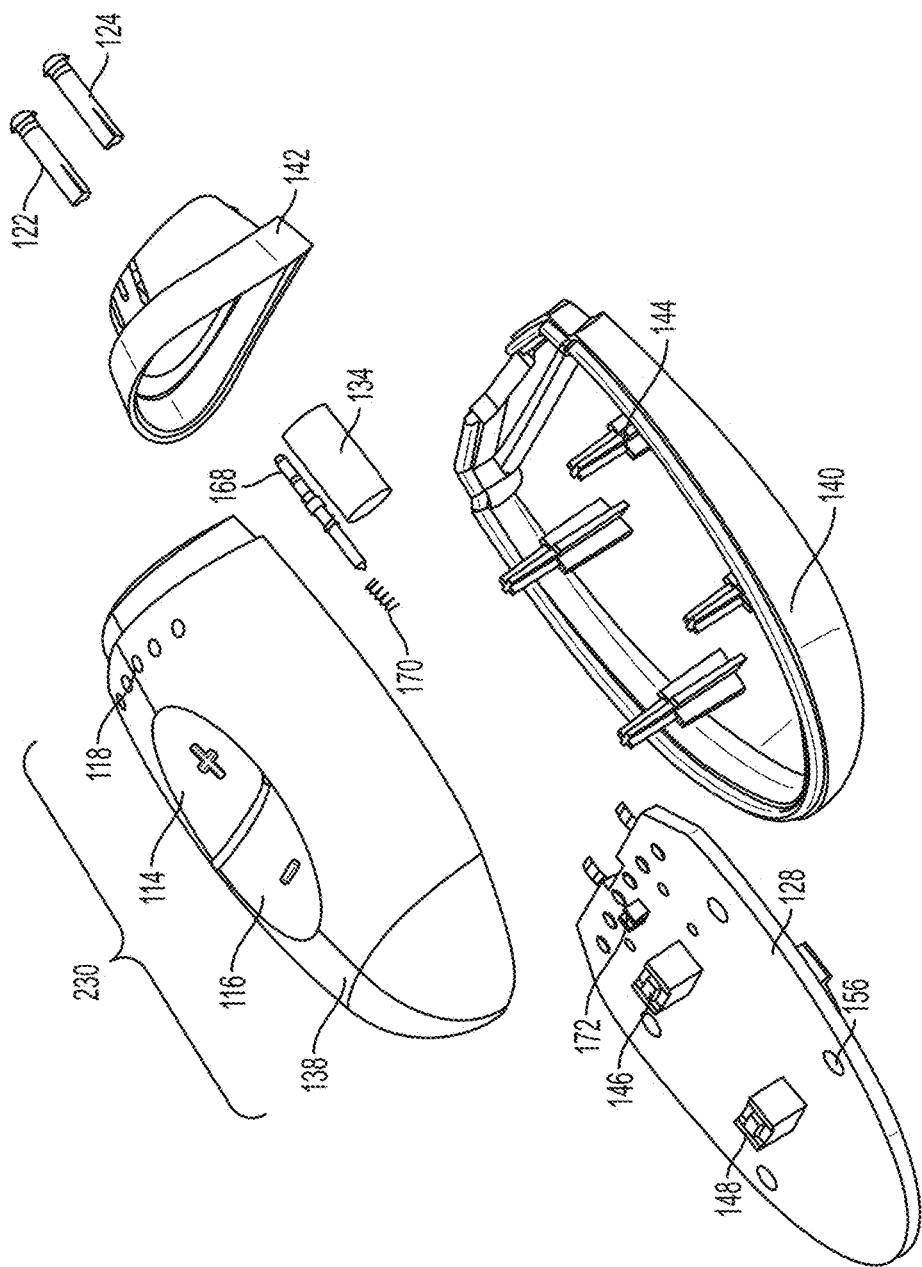
Figure 3C:
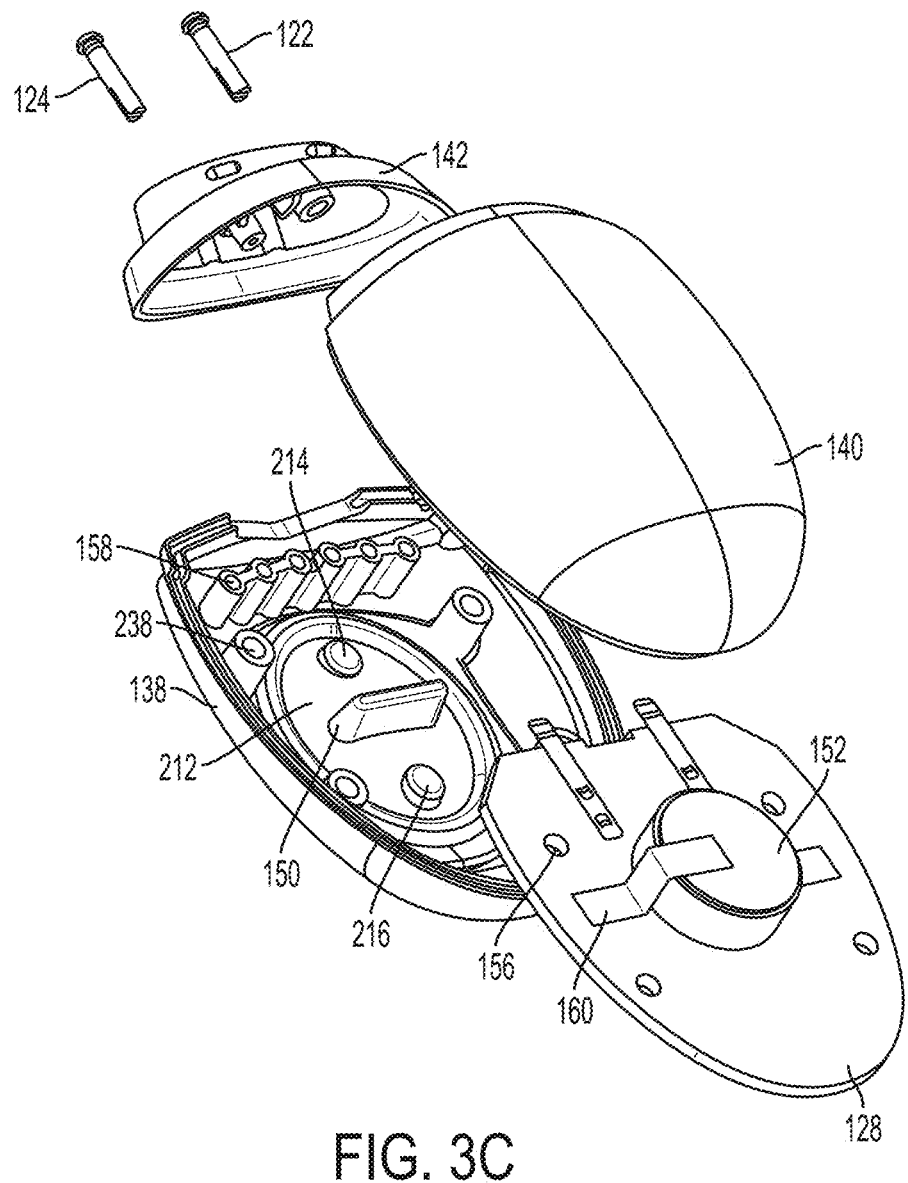

Turning to the stimulator body, FIG. 3A and FIGS. 3B-3C show a perspective view and exploded views, respectively, of the stimulator body 102. The stimulator body 102 may have any suitable shape. In some variations, it may be desirable for the stimulator body 102 to be shaped such that it can be easily gripped by a user, such that it can be held with one hand, such that it can be placed upright on a surface, and/or such that it can be easily and/or discretely carried in a pocket or purse. As shown in FIG. 3A, the stimulator body 102 may have a truncated ovoid shape. However, it should be appreciated that the stimulator body may have other shapes. The proximal end of the stimulator body 102 (formed by proximal housing 142) may have a shape that is complementary to the bottom of the stimulator probe 104, as described in more detail herein.

As mentioned above, the stimulator body may comprise a housing formed by a front housing 138, a back housing 140, and a proximal housing 142. These may fit together to form the exterior of the stimulator body. The front housing 138 and back housing 140 may fit together with any suitable attachment mechanism. For example, the front 138 and back 140 housings may fit together with a tongue-and-groove joint. The proximal housing 142 may comprise a proximal portion 204, which may fit over the proximal ends of the front and back housings 138 and 140, and a distal portion 206, which may fit within a portion of the stimulator probe 104, as described in more detail herein. The housing formed by the front 138, back 140, and proximal 142 housings may comprise any number of suitable openings for elements of the stimulator body. For example, the proximal housing 142 may comprise two lumens 208 and 210 that may be configured to receive connectors 122 and 124, as described in more detail herein. The front housing 138 may comprise an opening configured to receive a portion of the user interface 230, as described in more detail herein. It should be appreciated that while the housing is described here as comprising front, back, and proximal housings, the housing may be constructed from any number of separate housing components (e.g., two, three, four, five, or more).

In some instances, it may be desirable for the stimulator body to be sealed, such that it may be waterproof or the like. In some of these instances, when the housing comprises a front housing 138, back housing 140, and proximal housing 142, the three housing portions may attach so as to be watertight. For example, the tongue-and-groove joint described above may be watertight. In some variations, the stimulator body 102 may further comprise one or more seals located at the interface between the front housing 138 and the back housing 140, and/or between the front 138 and back 140 housings and the proximal housing 142. In variations in which the housing comprises openings for other elements of the stimulator body (e.g., connectors 122 and 124, a release mechanism, or the like), the interface between those elements and the stimulator housing may be watertight, and/or may comprise seals.

In some variations, it may be desirable for each of the front housing 138, back housing 140, and proximal housing 142 to be formed from the same material in order to improve the ability of the front housing 138, back housing 140, and proximal housing 142 to maintain a tight seal and to exhibit similar expansion/contraction properties with changes in temperature. In some variations, the front housing 138, back housing 140, and top housing 142 may each comprise a rigid material, such as a rigid plastic. For example, the front 138, back 140, and top 142 housings may comprise a thermoplastic such as acrylonitrile butadiene styrene (ABS), polycarbonate, polyetherimide (e.g., ULTEM™ polyetherimide). However, the housing may comprise any suitable material or materials. Furthermore, it should be appreciated that in some variations the front housing 138, back housing 140, and/or proximal housing 142 may comprise different materials.

Figure 3D:
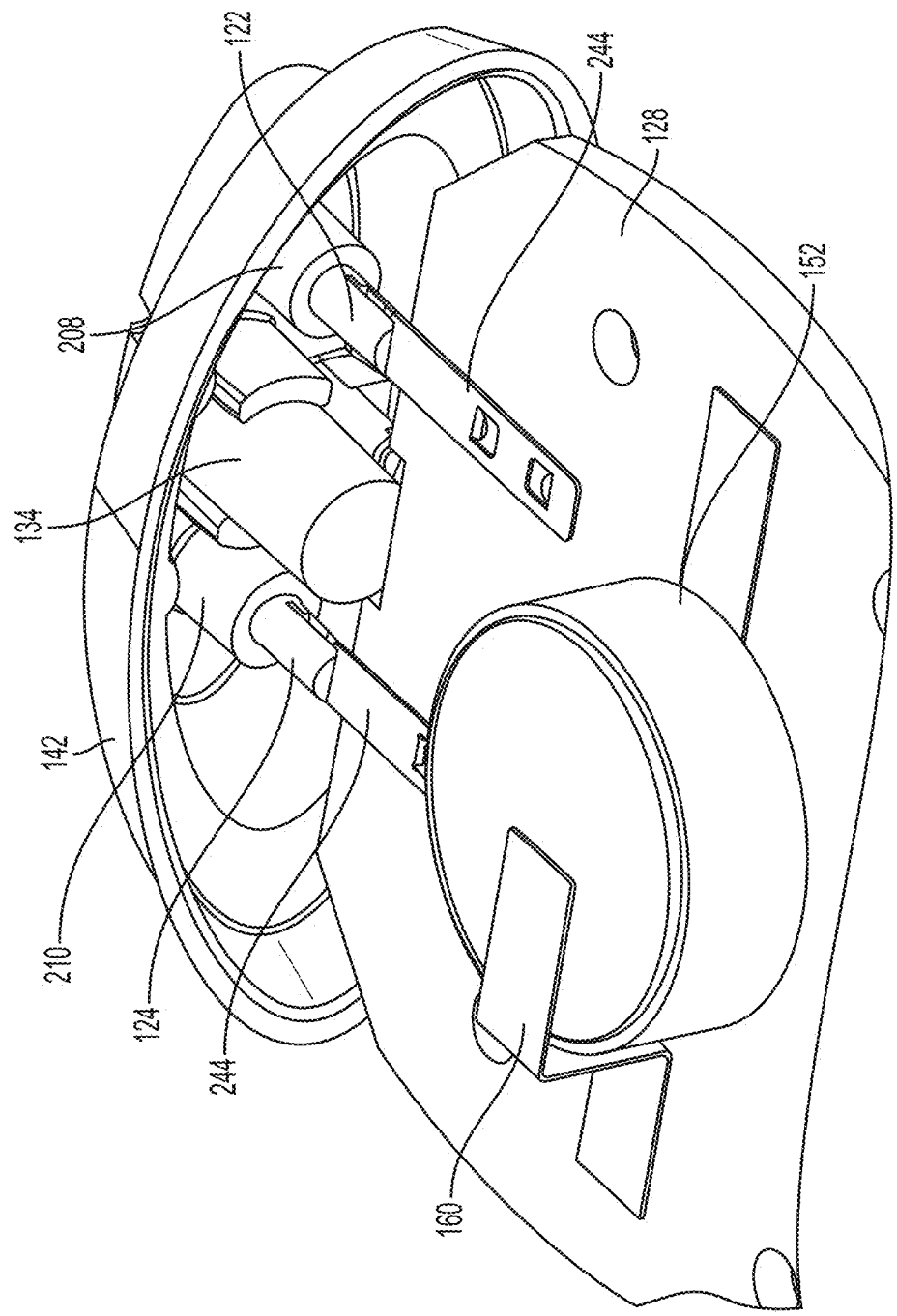
FIG. 3D shows a perspective view of a portion of the stimulator body of FIGS. 3A-3C.

In some variations the housing may comprise an alignment mechanism. The alignment mechanism may assist in aligning the stimulator body with the stimulator probe in variations in which the stimulator body and stimulator probe are detachable, and/or it may assist in keeping the stimulator body and stimulator probe connected. Additionally or alternatively, in which the stimulator system comprises a base station (as described in more detail herein), it may assist in aligning the stimulator body with the base station in variations and/or it may assist in keeping the stimulator body and the base station connected. In variations in which the stimulator is configured to be attached to a charging cable, the alignment mechanism may assist in aligning the stimulator or a portion of the stimulator with a charging cable and/or keeping the stimulator and charging cable attached. In some variations, the alignment mechanism may comprise a magnet. FIG. 3D shows a perspective view of a portion of the stimulator body 102. A magnet 134 may be connected to the interior surface of the proximal housing 142 as shown. In other variations, a magnet may be connected to the interior of another portion of the housing, or to the exterior of any portion of the housing. In variations in which the magnet 134 may assist in aligning the stimulator body 102 with the stimulator probe 104, the stimulator probe 104 may comprise a magnet or ferromagnetic material in a corresponding location. In variations in which the magnet 134 may assist in aligning the stimulator body 102 to a base station, the base station may comprise a magnet or ferromagnetic material in a corresponding location.

In some variations the housing may comprise a weight. It may in some instances be desirable for the stimulator to have a sufficient weight such that it has a substantial feel when held by a user. In some variations, the alignment mechanism (e.g., a magnet) may further serve as a weight. Additionally or alternatively, the weight may comprise a dense material or materials (e.g., iron or steel). The weight may be located in any suitable location within the housing. In some instances, the weight may be attached to the interior of the housing, to a printed circuit board comprising the control subsystem (described in more detail below), or threaded within pins holding a printed circuit board in place (e.g., pins 144 in stimulator body 102).

In some variations, the stimulator bodies described here may comprise features to assist the user in holding the device. For example, one or more portions of the stimulator may comprise ridges on both sides of the stimulator body. These ridges may act as grips for the user to hold onto. It should be appreciated that any of the stimulator bodies described here may comprise any suitable features to assist the user in holding the device, such as any texturized surface, a high-friction material (e.g., rubber), indentations, or the like.

In instances where the stimulators described here comprise a user interface, the user interface may comprise one or more operating mechanisms, which may allow the user to control one or more functions of the stimulator. For example, the operating mechanisms may allow the user to power the device on or off, start or stop the stimulus, change the intensity of the stimulus, change the duration of the stimulus, change the stimulus pattern, or the like. In some variations, the operating mechanisms may be able to activate or deactivate different functions, and/or may be able to change different parameters, based on their manner of operation (e.g., pressing a button briefly, pressing a button for a prolonged period, pressing a button with a particular pattern of pressing actions, rotating a dial by different angles or different speeds). Each of the one or more operating mechanisms may be any suitable structure, such as but not limited to a button, slider, lever, touch pad, knob, or deformable/squeezable portion of the housing, and a stimulator may comprise any combination of different operating mechanisms.

In one variation, the one or more operating mechanisms may comprise one or more buttons. The stimulator body 102, for example, may comprise two buttons 114 and 116. In the variation shown, the two buttons 114 and 116 may be located on a single a flexible membrane 212. The flexible membrane 212 may comprise any suitable material or materials, such as but not limited to a flexible polymer, such as a thermoplastic elastomer (e.g., a thermoplastic elastomer alloy (e.g., VERSAFLEX™ thermoplastic elastomer), thermoplastic polyurethane, or the like), silicone, or the like. In some variations in which the flexible membrane is located within the front housing 138, the flexible membrane 212 may be attached to the front housing 138 such that they are chemically bound. In some variations, they may be connected via overmolding, transfer molding, or two-shot molding. However, it should be appreciated that the flexible membrane 212 may be attached to the housing in any other suitable manner, such as via bonding.

The flexible membrane 212 may be separated into two buttons 114 and 116 by a divider 150. As shown in FIGS. 1E and 3C, the divider 150 may extend interiorly into the body cavity 154 from the interior surface of the flexible membrane 212. The end of the divider 150 may press against a fixed surface within the body cavity 154 of the stimulator body 154. For example, the end of the divider 150 may press against a portion of the printed circuit board (PCB) (128) that forms the control subsystem 136. The divider 150 may thus serve as an inflection point on the flexible membrane 212, such that each of the two buttons 114 and 116 may be pressed separately by the user. The divider 150 may also serve to resist separation between the flexible membrane 212 and the housing (e.g., by breaking the adhesion between the housing and the flexible membrane) by limiting the movement of the flexible membrane 212 into the body cavity 154.

If the user presses one of buttons 114 or 116, the movement of the button may be transferred to the control subsystem 136. As shown in FIG. 3C, the interior surface of the flexible membrane 212 may comprise two raised surfaces 214 and 216 on the interior surface of buttons 114 and 116, respectively. When button 114 or 116 is depressed, the corresponding raised surface 214 or 216 may press against PCB button 146 or 148 (shown in FIG. 3B), respectively, located in the printed circuit board 128, in order to transmit information to the control subsystem 136. While the stimulator body 102 is shown as having two buttons formed on a single flexible membrane, it should be appreciated that in other variations, two or more buttons may be separately formed.

In stimulator body 102, pressing the top button 114 may power on the stimulator 100 when the stimulator 100 is off. In some variations in which the stimulator is capable of differing stimulus intensities, the stimulator may be powered on to the last stimulus intensity from before the stimulator was powered off. When the stimulator 100 is on, pressing the top button 114 may increase the intensity of the stimulus (for example, when the stimulus is electrical, pressing the top button 114 may increase the amplitude of the stimulus waveform). Conversely, pressing the bottom button 116 may decrease the intensity of the stimulus (for example, when the stimulus is electrical, pressing the bottom button 116 may decrease the amplitude of the stimulus waveform). Pressing the bottom button 116 also may in some instances power off the stimulator 100. For example, pressing and holding the bottom button 116 may power off the stimulator 100; or additionally or alternatively, pressing the bottom button 116 when the stimulus intensity is at its lowest level may power off the stimulator 100. However, it should be appreciated that additionally or alternatively, the stimulator 100 may power off without user input (e.g., after a period of idle time). In some variations, the stimulator 100 may provide feedback to the user to indicate that the buttons are being pressed (or that other operating mechanisms are being operated). For example, pressing the buttons or operating any of a stimulator's operating mechanisms may be accompanied by a sound, vibration, tactile click, light, or the like, but need not be. It should be appreciated that the operating mechanisms of the stimulators described here may have any number of other suitable configurations.

Furthermore, the stimulators may be configured to provide feedback or otherwise convey information to a user. For example, in stimulator 100, the user interface 230 may comprise one or more light-based status indicators 118. The light-based status indicators 118 may comprise one or more light sources (e.g., LEDs) located on the printed circuit board 128, which may be connected to or located near light-transmitting elements 158 on the front housing 138. The light-transmitting elements 158 may transmit light from a light source on the printed circuit board 128 to the exterior of the housing, where it may be perceived by a user. In some variations, the light-transmitting elements 158 may comprise fiber optics (e.g., light pipes). In other variations, the light-transmitting elements 158 may comprise translucent or transparent epoxy) in the front housing 138.

Generally, the control subsystem of the stimulators described herein may be configured to control a stimulus to be delivered to a subject via the stimulator probe. The control subsystem may be contained within the housing the stimulator. The control subsystem may be connected to the operating mechanisms of the stimulator (e.g., the buttons), which may allow the control subsystem to receive input from a user. The control subsystem may also be connected to mechanisms configured to provide feedback or otherwise convey information to a user. In some variations, such as stimulator 100, the control subsystem 136 may be located on a printed circuit board 128. When the control subsystem 136 is located on a printed circuit board 128, the printed circuit board 128 may be fixed within the body cavity 154 of the stimulator body 102 in any suitable manner. In some variations, the printed circuit board 128 may be held in place relative to the housing by pins 144. As shown in FIG. 3B, the interior surface of back housing 140 may comprise four pins 144. The pins 144 may be configured to fit through corresponding openings 156 in the printed circuit board 128, and may be further configured to fit into receiving recesses 238 in the front housing 138. It should be appreciated that in other variations in which the printed circuit board is secured by pins, the housing may comprise any number of pins 144, which may be located on any portion of the housing.

The control subsystem 136 may include any circuitry or other components configured to operate the stimulators as described here. In some variations the control subsystem may comprise a processor 232, memory 234, and/or a stimulation subsystem 236. Generally, the processor may be configured to control operation of the various subsystems of the control subsystem. For example, the processor 232 may be configured to control the stimulation subsystem 236 to control parameters of the stimulation provided by the stimulation subsystem 236. The memory 234 may be configured to store programming instructions for the stimulator, and the processor 232 may use these programming instructions in controlling operation of the stimulator. The stimulation subsystem 236 may be configured to generate a stimulation signal and deliver the stimulation signal to a patient via the stimulator probe. In other variations, the control subsystem 136 may comprise a finite state machine.

In some variations, the control subsystem 136 may comprise a detection/recording subsystem. In these variations, the detection/recording subsystem may be configured to monitor one or more parameters of a subject (e.g., subject impedance), the stimulation delivered to the subject (e.g., date and time of stimulation, duration of the stimulation, amplitude of the stimulation signal, pulse width, frequency), and/or the stimulator itself (e.g., diagnostic data). The detection/recording subsystem may record some or all of this data to the memory. Additionally or alternatively, the control subsystem 136 may be configured to accept and record user input regarding subject symptomology, subject activity, or the like. Additionally or alternatively, the control subsystem may comprise a communications subsystem. The communication subsystem may be configured to facilitate communication of data and/or energy between the stimulator and an external source.

The control subsystem may in some variations comprise safety mechanisms, such as limits on the voltage, current, frequency, and duration of the stimulus when the stimulus is electrical. In some variations, some of these safety mechanisms may be part of the stimulation subsystem. For example, the stimulation subsystem 236 of the control subsystem 136 of stimulator 100 may limit the voltage and current that may be delivered to the patient. In some variations, the voltage may be limited by a voltage regulator. In some of these variations, the voltage limit may be between about 1 V and about 100 V. In some of these variations, the voltage limit may be between about 5 V and 50 V, between about 10 V and 25 V, or between about 15 V and 20 V. In some variations, the voltage may be regulated via a boost regulator connected to the power source 152, but it should be appreciated that any suitable voltage regulator may be used. In some variations, the current may be limited by a resistor in series with the load or a current-limiting transistor, or any other suitable combinations of elements. In some variations, the current limit may be about between about 1 mA to about 30 mA, between about 5 mA to about 20 mA, or about 10 mA. In some variations, the stimulation subsystem 236 may be capacitively coupled by one or more series capacitors on the output. This capacitive coupling may prevent DC currents from being applied to the patient, and may limit the total charge injection and pulse duration.

Additionally or alternatively, some or all of the safety mechanisms of the control subsystem 136 may be part of the processor 232. For example, the processor 232 may comprise software that limits the frequency to within an allowed range. In some variations, the frequency may be limited to between about between about 0.1 Hz and about 200 Hz, between about 10 Hz and about 60 Hz, between about 25 Hz and about 35 Hz, between about 50 Hz and about 90 Hz, between about 65 Hz and about 75 Hz, between about 130 Hz and about 170 Hz, between about 145 Hz and about 155 Hz, or between about 145 Hz and about 155 Hz. Additionally or alternatively, the processor 232 may comprise software that limits the stimulus intensity (e.g., the current or voltage). In some of these variations, the voltage limit may be between about 5 V and 50 V, between about 10 V and 25 V, or between about 15 V and 20 V. In some variations, the current limit may be about between about 1 mA to about 30 mA, between about 5 mA to about 20 mA, or about 10 mA. The processor 232 may additionally or alternatively comprise software that limits the stimulus duration. In some variations, the duration may be limited to about 1 minute, about 2 minutes, about 3 minutes, about 5 minutes, about 10 minutes, or the like. In some variations in which the stimulator probe 104 is removably connected to the stimulator body 102, the control subsystem 136 may prevent the delivery of current by the stimulation subsystem 236 when the stimulator probe 104 is disconnected from the stimulator body 102. Additionally or alternatively, the control subsystem 136 may prevent delivery of current by the stimulation subsystem 236 when the stimulator probe 104 is not in contact with a patient's tissue.

The stimulator may comprise a power source. The power source may be any suitable power supply capable of powering one or more functions of the stimulator, such as one or more batteries, capacitors, or the like. As shown in FIGS. 3C-3D, in some variations the power source may comprise a lithium coin cell battery 152. The battery 152 may be secured in place via any suitable method, such as a clip 160 attached to the printed circuit board 128 comprising the control subsystem 136. In some variations, the power source may be rechargeable.

While the stimulator body 102 comprises a power source, in other variations the stimulator body need not comprise a power source. In some variations, the stimulator body may comprise a port, cord, or other mechanism for connecting the stimulator to an external power source (such as a wall outlet or separate battery pack), which in turn may be used to power one or more portions of the stimulator. In some other variations, such a port, cord, or other mechanism may be used to recharge a rechargeable power source. The stimulator body 102 may comprise such a port (e.g., a USB port) at any suitable location, such as between the connectors 122 and 124 on the proximal housing 142, on the back housing 140, on the front housing 138, or at the proximal end of the stimulator body 102 between the front 138 and back housings 140.

Other variations and features of stimulator bodies and components thereof are described in U.S. application Ser. No. 14/256,915, filed Apr. 18, 2014, and titled "NASAL STIMULATION DEVICES AND METHODS," which is hereby incorporated by reference in its entirety.

Stimulator Probe

The stimulator probe of the stimulator may comprise one or more nasal insertion prongs, which may be configured to extend at least partially into a nasal cavity of a subject. FIGS. 5A, 5B, 5C, 5D, and FIGS. 5E-5F depict back, side, cut-away back, cut-away top, and perspective views, respectively, of the stimulator probe 104 of stimulator 100. As shown there, the stimulator probe 104 may comprise a first nasal insertion prong 106 and a second nasal insertion prong 108. The first and second prongs 106 and 108 may be connected via a base member 126. The base member 126 may be configured to hold at least a portion of the first and second prongs in fixed relation to each other.

The nasal insertion prongs 106 and 108 may generally be configured to be inserted a subject's nostrils. As shown in FIGS. 5A-5F, each nasal insertion prong 106 and 108 may comprise an elongate portion 162 and 164, respectively. Each elongate portion 162 and 164 may have at its distal end a distal portion 176 and 178. In some variations, the distal portions 176 and 178 may have a diameter (or greatest cross-sectional dimension) that is larger than the diameter (or greatest cross-sectional dimension) of the elongate portion 162 and 164 of the prongs proximal to the distal portions. This may allow a portion of the distal portions 176 and/or 178 (e.g., the electrodes, described below) to be brought into contact with a subject's tissue, while the elongate portions 162 and 164 are not in contact with the subject's tissue. For example, the diameter of the nasal insertion prongs 106 and 108 at the distal portions 176 and 178 may in some instances be between about 3 mm and about 7 mm, while the diameter of the elongate portions 162 and 164 may be between about 1 mm and about 6 mm proximal to the distal portions. More specifically, in some variations the diameter of the nasal insertion prongs at the distal portions 176 and 178 may be about 5 mm, and the diameter of the elongate portions 162 and 164 may be about 3 mm. The proximal portion of the elongate portions 162 and 164 may flare outward (i.e., have an increasing diameter or greatest cross-sectional dimension) toward the base member, which may in some variations act as a stop to limit the distance that the nasal insertion prongs 106 and 108 may be advanced into the nose of a user.

Figure 5C:
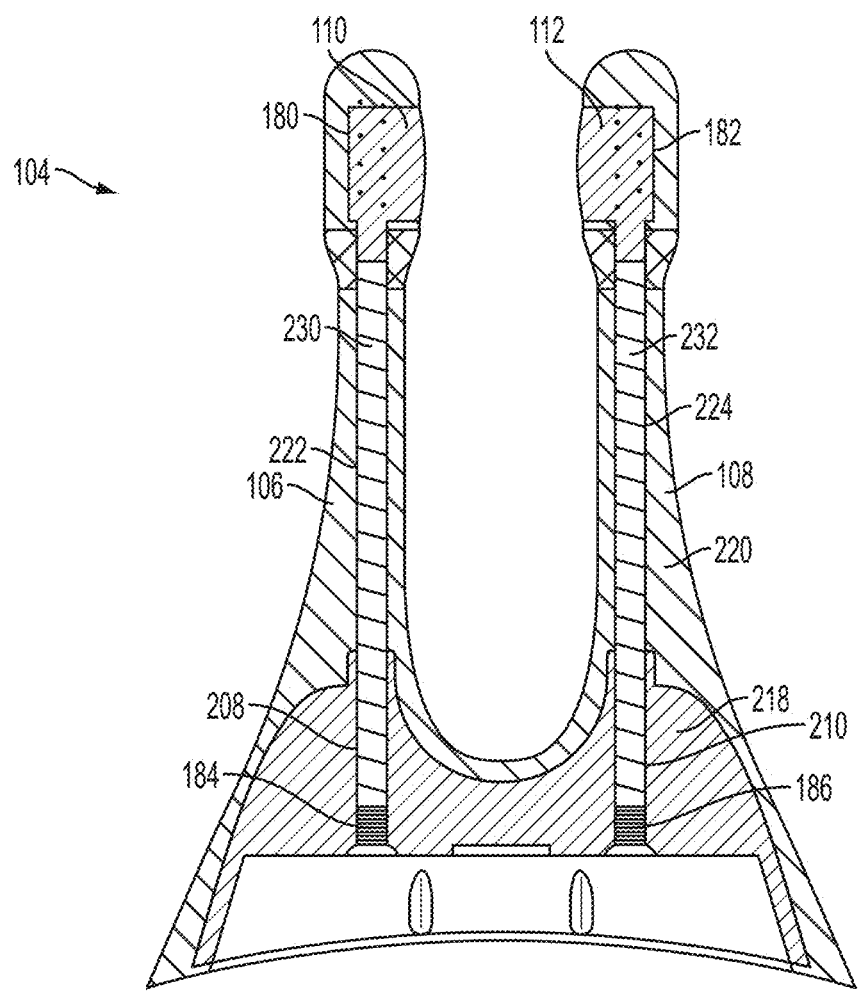
Figure 5D:
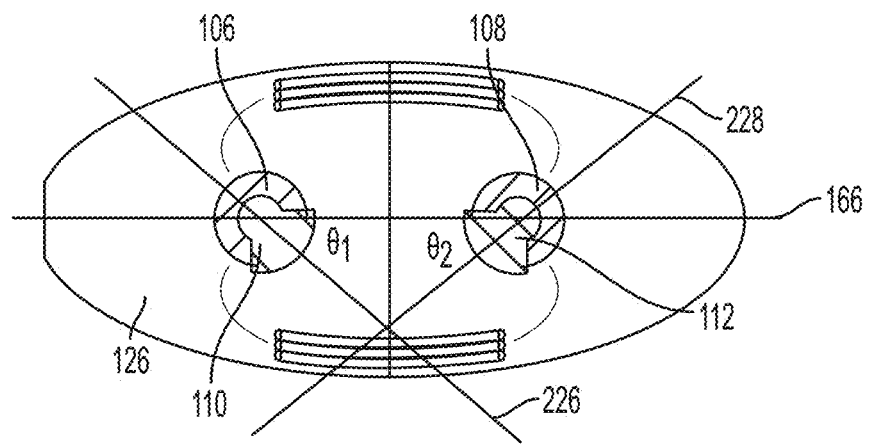
Figure 5E:
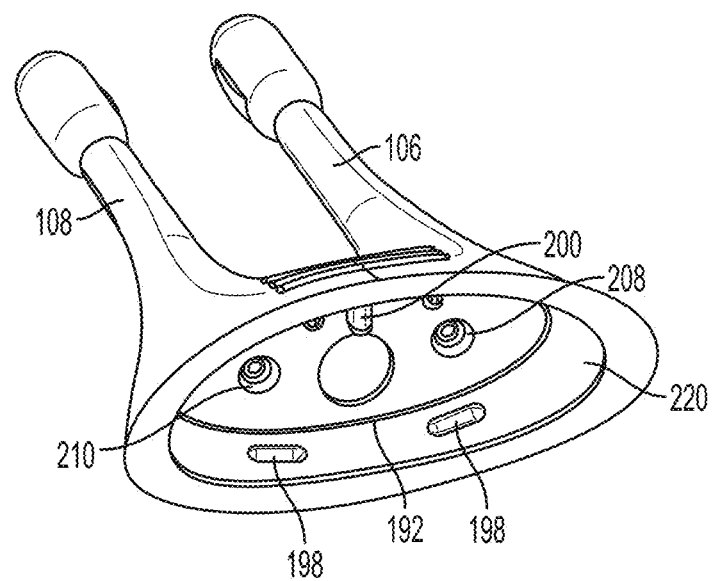
Figure 5F:
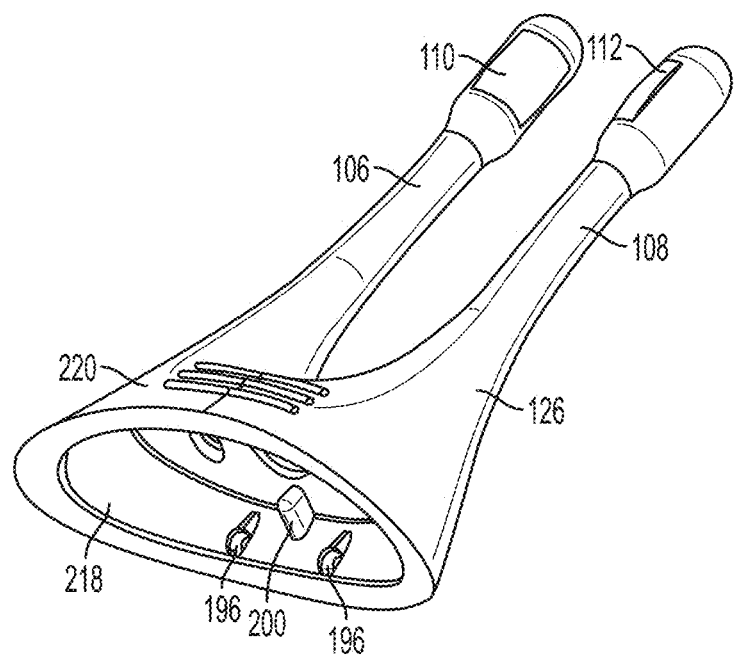
Figure 5G:
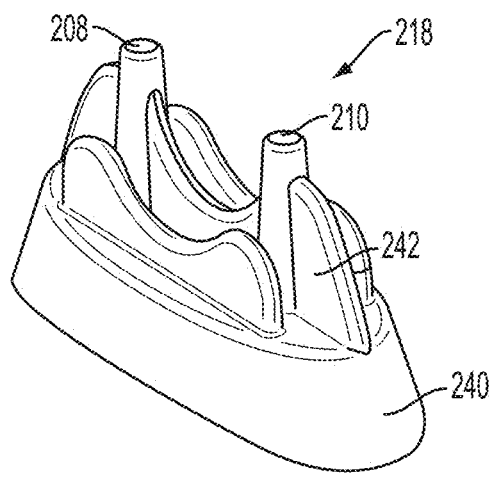
FIG. 5G depicts a perspective view of a rigid support of the stimulator probe of FIGS. 5A-5F.

The first and second nasal insertion prongs 106 and 108 may be connected to each other via a base member 126. In the variation shown in FIGS. 5A-5F, the prongs 106 and 108 may be integrally formed with the base member 126 by a rigid support 218 and a flexible overlay 220, as shown in FIG. 5C. The rigid support 218 may provide support to the base of the nasal insertion prongs 106 and 108 and may interface with the top of the stimulator body 102, as described in more detail below. The rigid support 218 may comprise any suitable material or materials, such as a rigid plastic. For example, in some variations, the rigid support 218 may comprise a thermoplastic such as acrylonitrile butadiene styrene (ABS), polycarbonate, polyetherimide (e.g., ULTEM™ polyetherimide). It may in some instances be desirable for the rigid support 218 to comprise the same material as a portion of the stimulator body 102 (e.g., the proximal housing 142 (described above)), in order to improve the ability to attach the stimulator probe 104 to the stimulator body 102, as described in more detail below. In some variations, the rigid support 218 may comprise a bottom portion 240 configured to interface with the stimulator body 102, and a top portion comprising one or more supports 242 (e.g., as shown in FIG. 5G, three supports 242). The top portion may further comprise two lumens 208 and 210, configured to receive leads as described below. In some variations, the supports 242 may be saddle-shaped.

The flexible overlay 220 may form the nasal insertion prongs 106 and 108 and may wrap around the rigid support 218 to form the base member 126. The flexible overlay 220 may comprise any suitable material or materials. The flexible overlay 220 may comprise a more flexible material than the rigid support 218. For example, in some variations the flexible overlay 220 may comprise a flexible polymer, such as a thermoplastic elastomer (e.g., thermoplastic elastomer alloys (e.g., VERSAFLEX™ thermoplastic elastomer), thermoplastic polyurethanes, or the like), silicone, or the like. Although the nasal insertion prongs 106 and 108 may be integrally formed with the base member 126 in stimulator probe 104, in other variations, the nasal insertion prongs may separately formed from the base member.

The base member 126 may allow the nasal insertion prongs 106 and 108 to be manipulated as a single unit (and disposed as a single unit, in instances where the stimulator probe is disposable). In some variations, the base member 126 may act as a stop to limit the distance that the nasal insertion prongs 106 and 108 may be advanced into the nose of a user. Additionally or alternatively, one or more of the nasal insertion prongs may include a flange or other mechanical stop to limit the distance that the prongs may be inserted into a user's nose. The base member 126 may further help to control the relative orientation of the prongs. For example, as shown in FIGS. 5A-5F, the two nasal insertion prongs 106 and 108 may be connected to the base member 126 such that the two prongs are oriented substantially parallel to each other. In some variations, having the nasal insertion prongs oriented substantially parallel to each other may provide advantages in manufacturing and may aid in nasal insertion. However, in other variations, the nasal insertion prongs may not be oriented parallel to each other. For example, in some variations, the nasal insertion prongs may be angled toward each other.

The two nasal insertion prongs may be positioned with any suitable distance between them (e.g., between about 3 mm and about 15 mm). In some variations, it may be desirable for the distance between the two nasal insertion prongs to be such that they fit simultaneously into each of the user's nostrils on either side of the septum. Additionally or alternatively, it may be desirable for the distance to be such that the nasal insertion prongs are configured to self-align to the desired stimulation location (described in more detail below) when inserted into the user's nasal cavities. In some of these variations, the distance between the central longitudinal axes of the two nasal insertion prongs 106 and 108 (labeled as distance "A" in FIG. 5A) may be between about 12 mm and about 16 mm. The diameter of the nasal insertion prongs at the distal portions 176 and 178 may in some instances be about 3 mm to about 7 mm as described above, and thus the distance between the distal portions (labeled as distance "B" in FIG. 5A) may be about 5 mm to about 11 mm. More specifically, in some variations the distance between the central axes of the two nasal insertion prongs 106 and 108 may be about 14 mm, and the diameter of the nasal insertion prongs at the distal portions 176 and 178 may be about 5 mm, and thus the distance between the distal portions may be about 11 mm.

The one or more nasal insertion prongs may have any suitable length. In some variations, the length of the one or more nasal insertion prongs may be such that when inserted into the nasal cavity, at least a portion (e.g., distal portions 176 and 178) is capable of reaching the area of the nasal cavity that is desired to be stimulated. For example, the length of the one or more nasal insertion prongs may be such that when inserted into the nasal cavity, at least a portion is capable of reaching the nasal mucosa or other area desired to be stimulated, as described in more detail below. In some variations, the length of the one or more nasal insertion prongs extending from the base member (i.e., the farthest the nasal insertion prongs could be inserted into the nasal cavity) may be between about 25 mm and about 45 mm. In other variations, the length of the one or more nasal insertion prongs extending from the base member may be between about 30 mm and about 40 mm. For example, in some variations, such as variations in which the stimulation target includes the anterior ethmoidal nerve, the nasal insertion prongs 106 and 108 may have a length extending from the base member 126 of about 37.5 mm (labeled as distance "C" in FIG. 5A). As another example, when the stimulation target includes an internal branch of the infraorbital nerve, the length of the one or more nasal insertion prongs extending from the base member may be between about 8 mm and about 20 mm. As yet another example, when the stimulation target includes a superior branch of the greater palatine nerve, the length of the one or more nasal insertion prongs extending from the base member may be between about 20 mm and about 40 mm. As yet another example, when the stimulation target includes a posterior superior lateral nasal branch of the maxillary nerve (when the tissue to be stimulation includes the middle and/or superior turbinates), the length of the one or more nasal insertion prongs extending from the base member may be between about 20 mm and 60 mm (e.g., between about 25 mm and about 35 mm, between about 30 mm and about 40 mm, between about 25 mm and about 40 mm). In other variations the nasal insertion prongs may be different lengths and/or adjustable lengths, and additionally or alternative may comprise one or more bends or curves.

The nasal insertion prong dimensions and configuration described with respect to stimulator probe 104 may allow the nasal insertion prongs 106 and 108 to self-align to the desired stimulation location when inserted into a user's nasal cavities. The length of the nasal insertion prongs is desirably long enough such that the prongs can reach the desired stimulation location (e.g., the nasal mucosa superior to the columella, such as near the interface between the nasal bone and the upper lateral cartilage; tissue innervated by a nerve target, such as but not limited to the anterior ethmoidal nerve, internal branches of the infraorbital nerve, superior branches of the greater palatine nerve, septal nerve, or posterior superior lateral nasal branch of the maxillary nerve) in a range of patients. However, it should be appreciated that in some instances it may be desirable to stimulate the columella. For those patients having a larger distance between the columella and the desired stimulation location, a longer portion of the nasal insertion prongs may be inserted into the nasal cavities. For those patients having a shorter distance between the columella and the desired stimulation location, a shorter portion of the nasal insertion prongs may be inserted into the nasal cavities. Because the patient's nasal cavities may narrow from inferior to superior, as the nasal stimulation prongs are advanced superiorly into the nasal cavities toward the desired stimulation location, the nasal tissue may generate a force pressing the nasal insertion prongs medially. When the nasal insertion prongs comprise a flexible material (e.g., a flexible polymer, such as a thermoplastic elastomer (e.g., a thermoplastic elastomer alloy (e.g., VERSAFLEX™ thermoplastic elastomer), thermoplastic polyurethane, or the like), silicone, or the like) as described herein, the nasal insertion prongs may flex medially, bringing them into contact with the desired stimulation location.

In some variations, it may be desirable to have a particular flexibility or range of flexibilities in order to allow the nasal insertion prongs to self-align to the desired stimulation location when inserted into a user's nasal cavities. In these variations, properties of the nasal insertion prongs (e.g., the Young's modulus, thickness of the flexible material or materials, the properties of the leads located within the prongs (described in more detail herein)) may be chosen to allow self-alignment. Generally, it may be desirable for the prongs to be stiff enough such that they can be pushed into the nasal cavities without buckling, while being flexible enough to self-align and/or to be atraumatic to the nasal tissue during regular use and insertion, and/or during a sudden movement (e.g., a sneeze). This may also improve comfort for the user. In some variations, the desired hardness of the material may be between about 40 D and about 90 D, between about 50 D and about 80 D, between about 60 D and about 70 D, or about 65 D. In addition to having material properties that may be atraumatic to nasal tissue, it may be desirable for the distal tips of the nasal insertion prongs to have rounded edges to help minimize the risk of tissue damage during advancement of the prongs into the nose.

When the stimulators described here are configured to deliver an electrical stimulus, at least one of the nasal insertion prongs may comprise one or more electrodes configured to deliver a stimulus to tissue. In variations where a stimulator comprises two nasal insertion prongs, each of the two nasal insertion prongs may comprise at least one electrode. Having multiple electrode-bearing prongs may allow the stimulator to provide bipolar stimulation (and/or bilateral stimulation of two nostrils), as discussed in more detail herein.

When a nasal insertion prong or prongs of the stimulators describe here comprise one or more electrodes, the electrodes may have any suitable design. In variations in which the electrodes comprise an arc of a cylindrical surface, such as in the variation shown in FIGS. 5A-5F, the electrodes 110 and 112 may comprise about a 100 degree arc of a cylindrical surface. That is, openings 180 and 182 in the distal portions 176 and 178 of the nasal insertion prongs may comprise about a 100 degree arc of a cylinder, and the electrodes 110 and 112 may be located within the openings 180 and 182. In other variations, the electrodes may be any suitable arc length of a cylinder and further may have any suitable shape. For example, in some variations the electrodes may comprise a complete cylinder (e.g., may extend 360 degrees around the distal portions of the nasal insertion prongs), or in other variations, the electrodes may have a domed shape that includes the distal tips of the nasal insertion prongs. Such a complete cylinder or domed shape may be desirable, for example, when the targeted tissue area comprises two or more areas of tissue (e.g., stimulation is configured to stimulate two or more target nerves simultaneously). For example, such electrodes may be desirable when the targeted tissue areas comprise the area innervated by the superior branches of the greater palatine nerve and the area innervated by the nasopalatine nerve. As another example, such electrodes may be desirable when the targeted tissue areas comprise the area innervated by the posterior superior lateral nasal branches of the maxillary nerve and the area innervated by the nasopalatine nerve.

When the nasal insertion prongs comprise one or more electrodes, the center of the electrodes may be angled relative to the axis intersecting the first and second prongs. In some variations, the electrodes may be angled such that when the first nasal insertion prong is positioned in a first nostril and the second nasal insertion prong is positioned in the second nostril, the electrodes may be directed toward the front of the nose. When an electrical stimulus is delivered through the electrodes of the first and second nasal insertion prongs, the stimulation energy may be directed toward the front of the nose. This may allow for selective activation of nerves in the front of the septum and nasal mucosa, while minimizing activation of nerves toward the rear of the nasal septum. This may reduce negative side effects that may occur from stimulation of nerves that innervate the teeth. Specifically, in the variation of the stimulator probe 104, as shown in FIG. 5D, the center of the electrode 110 of the first nasal insertion prong 106 (shown by line 226) may be rotated at an angle $\theta_1$ relative to the axis 166 intersecting the first 106 and second 108 nasal insertion prongs, while the center of the electrode 112 of the second nasal insertion prong 108 (shown by line 228) may be rotated at an angle $\theta_2$ relative to the axis 166.

Figure 6:
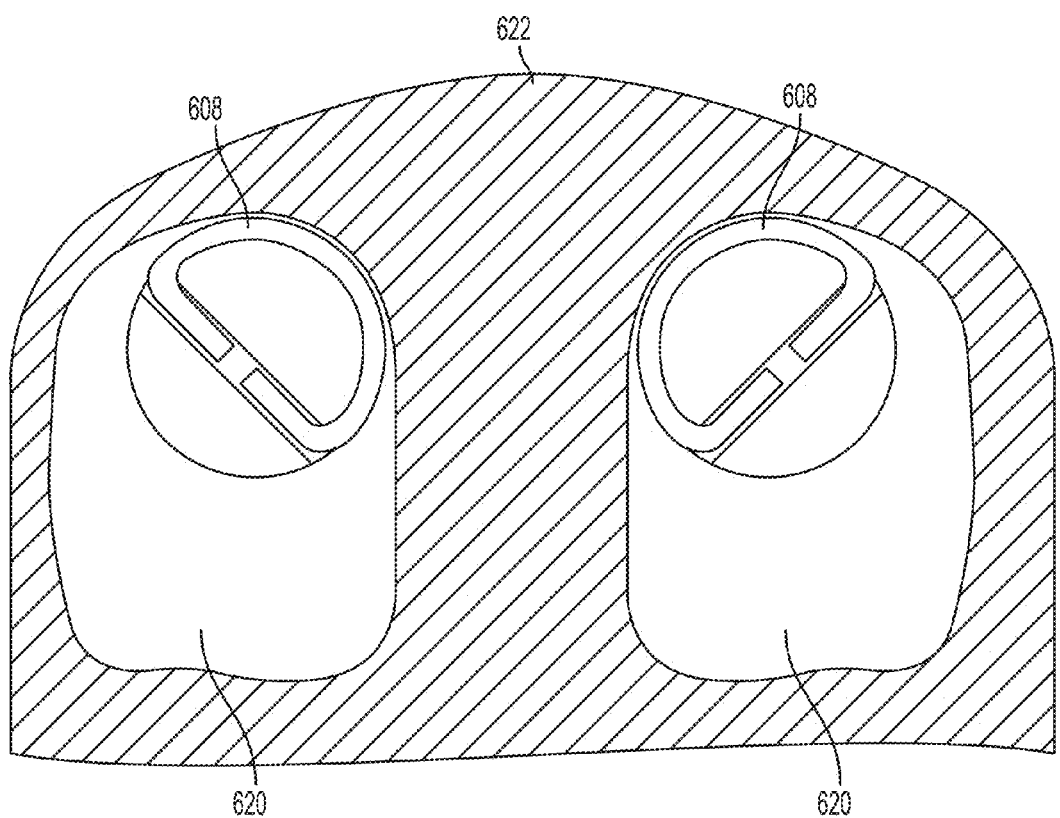
FIG. 6 shows a cross-sectional view of a stimulator probe positioned in the nose of a user.

The angles $\theta_1$ and $\theta_2$ of the stimulator probe 104 may be the same or different, and may be any suitable value (e.g., about 45 degrees, about 90 degrees, about 180 degrees, between about 0 degrees and about 90 degrees, between about 15 and about 75 degrees, or the like). In some variations, it may be desirable for angles $\theta_1$ and $\theta_2$ to be greater than about 10 degrees. In other variations, the center of the electrodes may face each other (e.g., angles $\theta_1$ and $\theta_2$ may be zero). This may cause the electrodes to face toward septal tissue when each nasal insertion prong is positioned in a nostril. In some variations, this may enhance activation of rhinorrhea and/or may enhance constriction of the lamina propia. In other variations, the centers of the electrodes may face in the same direction or nearly in the same direction (e.g., angles $\theta_1$ and $\theta_2$ may be between about 70 degrees and about 90 degrees, which may cause the electrodes to face toward the front of the nose when each nasal insertion prong is positioned in a nostril). In other variations, the centers of the electrodes may be oriented such that angles $\theta_1$ and $\theta_2$ may be between about 10 degrees and about 50 degrees. In yet other variations, the centers of the electrodes may be oriented such that the electrodes face away from each other. In some instances, this may allow for stimulation of tissue in the nasal turbinates and/or tissue innervated by the superior branches of the greater palatine nerve. In the variation shown in FIGS. 5D, the angles $\theta_1$ and $\theta_2$ may each be 45 degrees. As such, when the stimulator probe 104 or 1200 is positioned such that the first nasal insertion prong is positioned in a first nostril and the second nasal insertion prong is positioned in the second nostril, the electrodes may be directed partially toward the front of the nose. For example, FIG. 6 shows electrodes 608 positioned in nostrils 620 against septum 622 and directed partially toward the front of the nose.

The electrodes may be positioned on any suitable longitudinal portion or portions of the nasal insertion prongs. The position of the electrode along the prong may at least partially determine the placement of the electrode relative to tissue when the stimulator probe is advanced into the nose. In some variations, an electrode may be located at an intermediate position along a prong of stimulator. For example, in the variation of the stimulator probes depicted in FIGS. 5A-5F, the electrodes 110 and 112 may be located at an intermediate position along the nasal insertion prongs, within the distal portions 176 and 178 the prongs but not at the distal tip of the prongs. The electrodes 110 and 112 may be located any suitable distance from the distal tip of the prongs, such as between about 0.1 mm and about 4 mm, about 4 mm and about 8 mm, or more than 8 mm from the distal dip of the prongs (e.g., 1 cm from the distal tip). In some variations, the electrodes 110 and 112 may be located about 2.5 mm from the distal tip of the prongs. In some variations, the electrodes may be locate such that when inserted into the nasal cavity, the electrodes are capable of reaching the nasal mucosa or other area desired to be stimulated. In some variations, distance from the base member of the stimulator probe to the longitudinal center of the electrode (i.e., the farthest the center of the electrode could be inserted into the nasal cavity) may be between about 25 mm and about 45 mm. In other variations, the distance from the base member of the stimulator probe to the longitudinal center of the electrode may be between about 30 mm and about 40 mm. For example, in some variations the distance from the base member of the stimulator probe to the longitudinal center of the electrode may be about 32.5 mm (labeled as distance "D" in FIG. 5A). In other variations, the distance from the base member of the stimulator probe to the longitudinal center of the electrode may be between about 20 mm and about 60 mm (e.g., between about 25 mm and about 35 mm, between about 30 mm and about 40 mm, between about 25 mm and about 45 mm, between about 20 mm and about 40 mm). In other variations, the distance from the base member of the stimulator probe to the longitudinal center of the electrode may be between about 8 mm and about 20 mm. The electrode may have any suitable length, such as between about 1 mm and about 10 mm, between about 3 mm and about 7 mm, about 5 mm, or more than about 10 mm.

The electrode(s) described here may be made from one or more conductive materials. In some variations, the electrodes may comprise metals (e.g., stainless steel, titanium, tantalum, platinum or platinum-iridium, other alloys thereof, or the like), conductive ceramics (e.g., titanium nitride), liquids, gels, or the like. In some variations, the electrode may comprise one or more materials configured to promote electrical contact between electrodes of the stimulator probe and tissue (i.e., all of an electrodes or a portion of the electrode, such as a covering). In some instances, the impedance provided by tissue may be at least partially dependent on the presence or absence of fluid-like materials (e.g., mucous) in the nasal cavity. The material(s) may help to minimize the impact of subject tissue impedance by providing a wet interface between the electrode and tissue, which may act to normalize the impedance experienced by the electrodes. This may in turn normalize the output and sensation experienced by the user.

In the variation shown in FIGS. 5A-5F, the electrode may comprise a hydrogel. The hydrogel may be any suitable hydrogel, including the hydrogels described in U.S. patent application Ser. No. 14/630,471, filed on Feb. 24, 2015, and titled "POLYMER FORMULATIONS FOR NASOLACRIMAL STIMULATION," which is hereby incorporated by reference in its entirety. The hydrogel may be located within the openings 180 and 182 of the distal portions 176 and 178 of the nasal insertion prongs 106 and 108. The hydrogel electrode may form about a 100 degree arc of a cylinder, although it should be appreciated that the hydrogel electrode may in other variations have other shapes (e.g., a smaller or larger arc, as described in detail herein). The hydrogel may fill the openings 180 and 182 and the adjacent portions of the central lumens 222 and 224 of the nasal insertion prongs. As such, the hydrogel may surround the axial portion of the leads located adjacent to the openings 180 and 182. In some variations, the distal portions 176 and 178 of the nasal insertion prongs may further be covered by a thin hydrogel skin. The hydrogel skin may help to retain the hydrogel electrodes within the distal portions 176 and 178 of the nasal insertion prongs 106 and 108. Additionally or alternatively, in variations having a hydrogel skin, the hydrogel skin may improve manufacturability (e.g., by allowing the electrodes to be formed by dip coating). In some variations, the distal portions 176 and 178 of the nasal insertion prongs 106 and 108 may comprise retention columns located between the surface of the electrode and the central lumens 222 and 224. The retention columns may help to retain the leads within the central lumens, and when the electrodes comprise a hydrogel, may help to retain the hydrogel within the opening 180 and 182.

When a nasal insertion prong or prongs of the stimulators described here comprise one or more electrodes, the electrodes may comprise leads. When the stimulator probe is connected to a stimulator body, the leads may contact the circuitry of the stimulator body to electrically connect the electrodes to the stimulator body circuitry, as described in more detail herein. As such, the leads may extend at least partially through each of the nasal insertion prongs. The leads may be formed from one or more conductive materials (e.g., stainless steel, titanium, platinum or platinum-iridium, other alloys thereof, or the like), conductive ceramics (e.g., titanium nitride), and may be positioned such that at least a portion of each lead contacts a respective electrode to provide a conduction pathway between the lead and the electrode.

The leads of stimulator probe 104 can be seen in the cut-away view in FIG. 5C. As shown there, the leads 130 and 132 may each comprise a spring. The springs comprising leads 130 and 132 may comprise any suitable biocompatible conductive material or materials. For example, in some variations, the springs may comprise stainless steel. In other variations, the springs may comprise gold or platinum. In some variations, the springs may comprise two or more materials (e.g., stainless steel with gold plating). The leads 130 and 132 may extend through the central lumens 222 and 224 of the nasal insertion prongs 106 and 108, respectively. A portion of the leads (e.g., the distal ends) may contact the electrodes. For example, distal ends of the leads 130 and 132 may extend through the hydrogel forming electrodes 110 and 112, as described in more detail herein. In variations in which the leads comprise springs, the wound coil of the springs may allow for a greater conductive surface between the leads and the hydrogel electrode as compared to a single straight wire. Additionally or alternatively, the wound coil of the springs 130 and 132 may grip the hydrogel electrode, thus better retaining it within the distal portions 176 and 178 of the nasal insertion prongs 106 and 108. The proximal ends of the leads 130 and 132 may extend through the lumens 208 and 210 through the rigid support 218, such that the proximal ends of the leads are able to contact the circuitry of the stimulator body, as described in more detail herein. In variations in which the leads comprise springs, the proximal ends 184 and 186 of the springs may have a tighter pitch than the rest of the springs. This may create a more even surface to contact the circuitry of the stimulator body. The spring force may also promote contact between the leads and the circuitry of the stimulator body, as described in more detail herein. Additionally or alternatively, the proximal ends 184 and 186 may have a different (e.g., greater) coil diameter than the rest of the springs, which may also improve the contact between the leads and a portion of the stimulator body. It should be appreciated the leads need not comprise springs. In other variations, for example, stimulator probes may comprise leads comprising a conductive loop.

Generally, when the stimulator probes described here are configured to deliver an electrical stimulus, the external surfaces of any of the stimulator probes described herein may be insulated, with the exception of the electrodes. This may help to prevent inadvertent stimulation of other tissue (e.g., by direct tissue contact with a lead instead of with an electrode). Accordingly, in some variations, the prongs may be formed from or otherwise coated with one or more insulating materials (e.g., PTFE, silicone, combinations thereof, or the like). For example, in the variation of the stimulator probe shown in FIGS. 5A-5F, the first and second prongs may be formed from an insulating material such as a flexible polymer (e.g., a thermoplastic elastomer (e.g., thermoplastic elastomer alloys (e.g., VERSAFLEX™ thermoplastic elastomer), thermoplastic polyurethanes, or the like), silicone, or the like), and the leads may be positioned inside the prongs such that they are electrically insulated from the exterior surfaces of the first and second prongs during use of the stimulator probe, as described herein. Accordingly, in these instances, electrical stimulation energy provided to the leads may be delivered via the electrodes.

Other variations and features of stimulator probes and components thereof are described in U.S. application Ser. No. 14/256,915, filed Apr. 18, 2014, and titled "NASAL STIMULATION DEVICES AND METHODS," which was previously incorporated by reference in its entirety. For example, while the stimulator probes in the figures described herein are shown as having two nasal stimulation prongs, it should be appreciated that in other variations the stimulator probe may have any suitable number of prongs (e.g., one, two, or three or more prongs). Similarly, the stimulators may comprise any suitable number of electrodes (e.g., one, two, three, or four or more electrodes), and the electrodes may be positioned on any suitable portion of the stimulator (e.g., the stimulator body and/or a stimulator probe).

Connection Between Stimulator Body & Probe

The stimulator probes described here (and any prongs thereof) may be connected to a stimulator body in any suitable manner. In some variations, a stimulator probe may be configured to directly connect to a stimulator body. In these variations, at least a portion of the stimulator probe may have a fixed location and orientation with respect to the stimulator body when the two are connected. In some of these variations, the stimulator probe may be permanently connected to the stimulator body. For example, the stimulator probe and stimulator body may be formed together such that they are permanently connected. In other variations, the stimulator probe may clip, latch, snap onto, or otherwise mechanically connect to the stimulator body. In some of these variations, the stimulator probe may be releasably connected to the stimulator body, such that the stimulator probe may be disconnected from the stimulator body after being connected.

Figure 7:
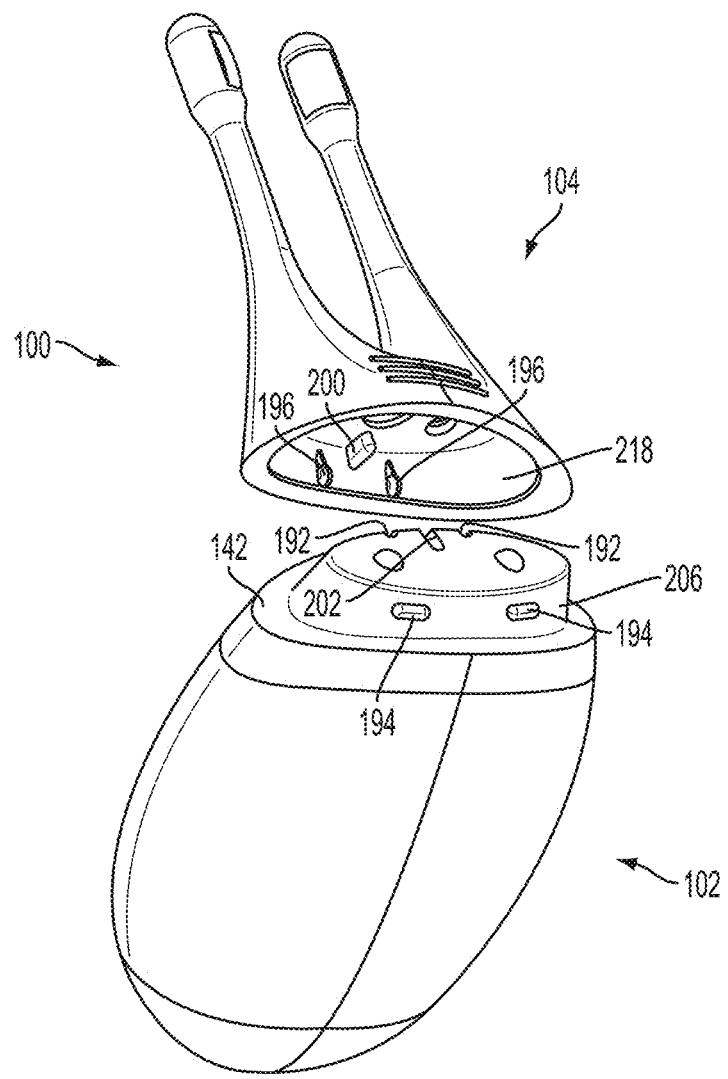
FIG. 7 depicts a perspective view of the stimulator of FIGS. 1A-1E with the stimulator probe disconnected from the stimulator body.

For example, stimulator body 102 and stimulator probe 104 of stimulator 100 may be removably connected such that a portion of the stimulator probe 104 directly contacts and connects to the stimulator body 104. FIG. 7 depicts a perspective view of the stimulator 100 showing the connection mechanism. As shown there, the distal portion 206 of the top housing 142 of the stimulator body 102 and the proximal portion of the stimulator probe 104 may comprise corresponding and complementary shapes, which may allow the stimulator body 102 and stimulator probe 104 to be attached. For example, the distal portion 206 of the top housing 142 of the stimulator body and the proximal surface of the rigid support 218 of the stimulator probe 104 may comprise features that allow them to be reversibly attached. For example, in the variation shown the distal portion 206 of the top housing 142 of the stimulator body 102 may comprise two notches 192 on a first side and two notches 194 on a second side. The proximal surface of the rigid support 218 of stimulator probe 104 may comprise four corresponding tabs: two tabs 196 on a first side and two tabs 198 on a second side (shown in FIG. 5E). The stimulator body 102 and stimulator probe 104 may be snapped together by first placing tabs 198 of the stimulator probe 104 into the notches 194 of stimulator body 102, and then manipulating the probe 104 and body 102 such that the first side of the simulator body 102 is rotated toward the first side of the stimulator probe 104. In doing so, the tabs 196 of the stimulator probe 104 may be rotatably inserted into the notches 192 of the stimulator body 102. The tabs 196 and 198 and notches 192 and 194 may have increased height and depth, respectively, at their proximal ends, such that the probe 104 and body 102 are held together by the tabs and notches when connected.

Conversely, the stimulator probe 104 may be removed from the stimulator body 102 by rotating the first side of the probe 104 and first side of the body 102 away from each other. It may be desirable for the stimulator to be configured such that when a user inserts the stimulator probe 104 into his/her nasal cavities, if the user presses a portion of the stimulator prongs (e.g., the electrodes) against tissue (e.g., tissue near the front of the nose), the force on the stimulator probe reinforces the connection between the stimulator probe 104 and the stimulator body 102. That is, the force from the user's tissue may desirably tend to push the first side of the stimulator body 102 toward the first side of the stimulator probe 104. If, instead, the force tended to push the first side of the probe 104 and the first side of the body 102 away from each other, there could be an increased risk of the probe being inadvertently disconnected from the stimulator body during stimulation. In some variations, as described in more detail below, the stimulator probe 104 may further comprise tab 200 configured to fit into notch 202 of stimulator body 102, which may help the control subsystem 136 to register the connection of the stimulator probe 104 to the stimulator body 102.

It should be appreciated that in other variations, the stimulator body and stimulator probe may have any suitable features for being attached, such as other snapping mechanisms (e.g., having different shapes or different numbers of features), magnets, friction fits, a latching mechanism, or the like. For example, in some variations the stimulator body may comprise a magnet (e.g., magnet 134 of stimulator body 102) connected to the interior surface of the proximal housing of the stimulator body. The stimulator probe may comprise a magnet or ferromagnetic material in a corresponding location (e.g., in the base member of the stimulator probe), which may retain the stimulator probe on the stimulator body.

Generally, when the stimulators described here are configured to deliver an electrical stimulus, the electrodes of the stimulator may be electrically connected to the stimulator circuitry, such that the stimulator may generate a stimulus and deliver it to tissue via one or more of the electrodes. Accordingly, the stimulators described here may comprise one or more electrical connections configured to electrically connect the electrode via a lead to a portion of the stimulator body (e.g., a stimulation subsystem housed in the stimulator body). In variations in which the stimulator probe and stimulator body are indirectly connected, the indirect connection (e.g., a cable, cord, or the like) may serve as the electrical connection between the stimulator circuitry and the electrodes. In variations in which the stimulator probe and the stimulator body are directly connected, the stimulator body and stimulator probe may comprise conductive elements configured to electrically connect the electrodes of the stimulator probe to the stimulator circuitry when the body and probe are connected.

Figure 1D:
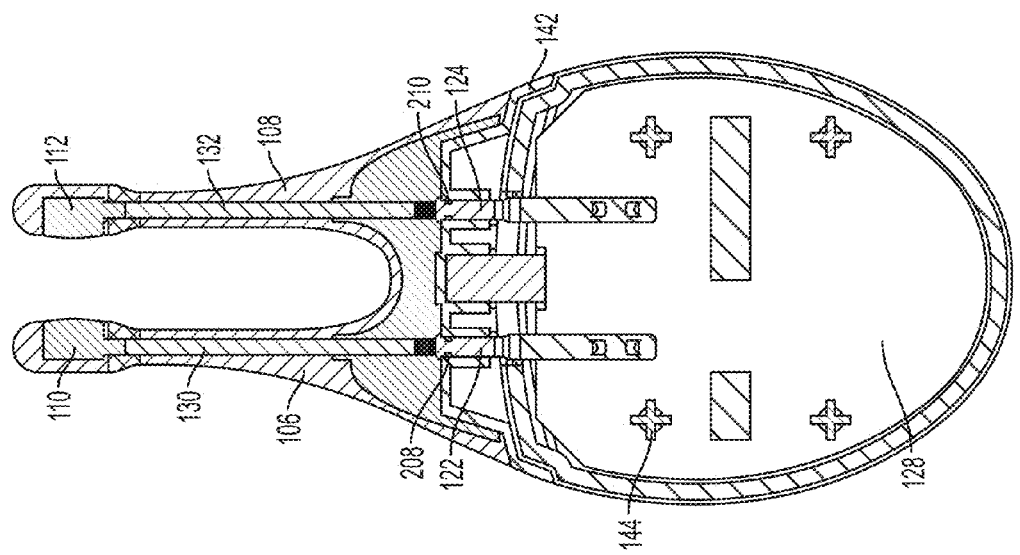
Figure 2:
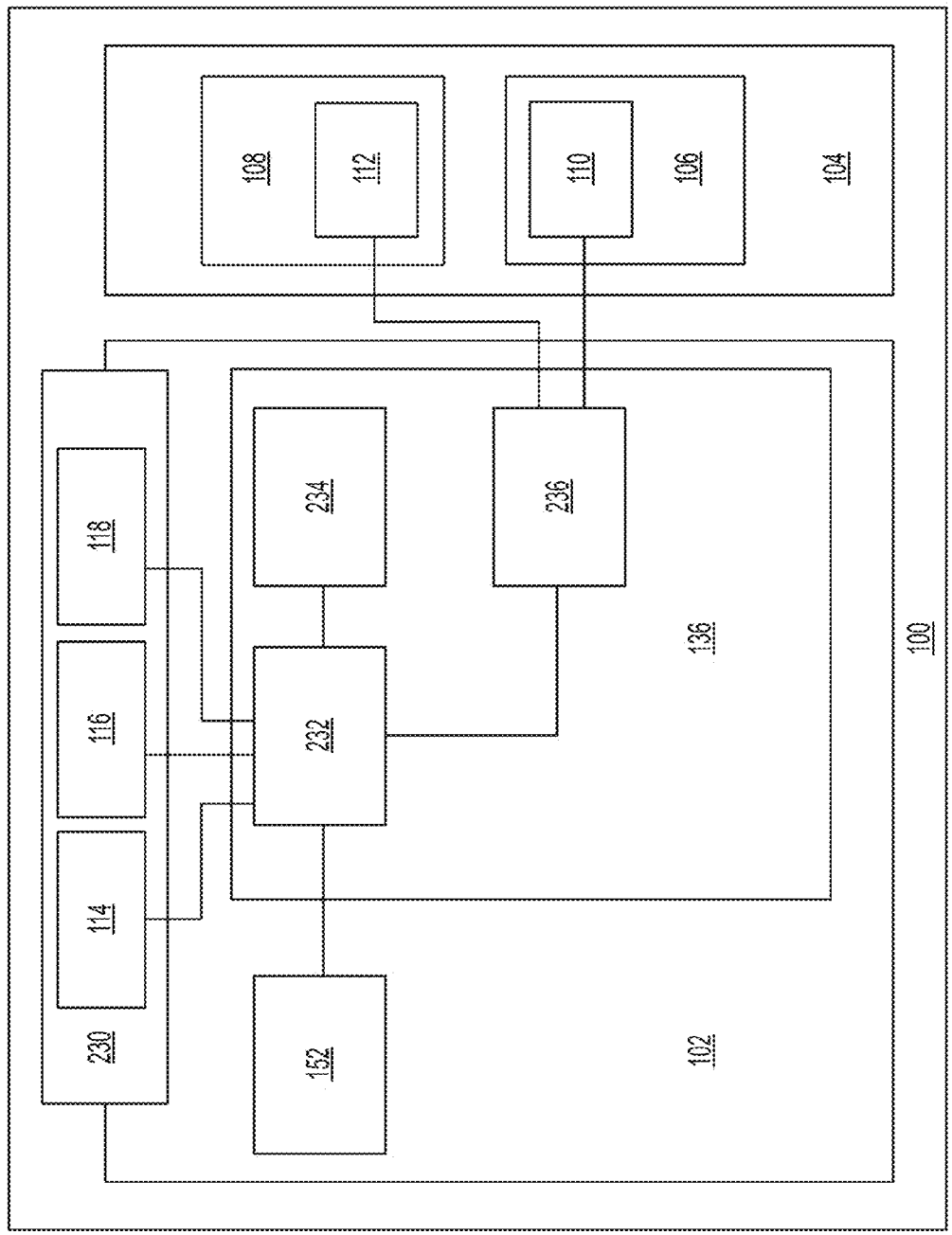
FIG. 2 shows a block diagram schematically representing a variation of a stimulator.

For example, as shown in FIG. 1D, the electrodes 110 and 112 of stimulator probe 104 may be connected to leads 130 and 132 located within nasal insertion prongs 106 and 108, respectively. The corresponding stimulator body 102 may comprise connectors 122 and 124 directly or indirectly connected to the control subsystem 136 and power source 152. The distal ends of the connectors 122 and 124 may be configured to connect with the proximal ends of the leads 130 and 132 of the stimulator probe 104. As shown in FIG. 3A, in some variations the distal ends of the connectors may comprise a rounded surface. In variations in which the leads comprise springs, the proximal ends of the springs may have a tighter pitch than the rest of the springs. This may create a more even surface to contact proximal ends of the connectors, and thus may allow for a better electrical connection between the leads of the stimulator probe 104 and the connectors of the stimulator body 102.

When the proximal ends of the springs of stimulator probe 104 are in contact with the connectors 122 and 124 of the stimulator body 102, the springs may be compressed. This compression may cause the springs to generating a restoring force. The restoring force may promote contact between the springs and the connectors 122 and 124. However, in variations in which the stimulator probe 104 is removably connectable to the stimulator body 102, the restoring force may also act against the force of the connection mechanism holding together the stimulator probe and the stimulator body (e.g., notches 192 and 194 and tabs 196 and 198). Thus, it may be desirable for the spring stiffness to be low enough that the restoring force of the springs does not cause the stimulator probe to disconnect from the stimulator body.

The connectors 122 and 124 may extend through lumens 208 and 210 in the proximal housing 142, and the proximal ends may be directly or indirectly attached to the control subsystem. As shown in FIG. 3D, the proximal ends of the connectors 122 and 124 may comprise slots configured to receive the distal ends of contact strips 244. The proximal ends of contact strips 244 may be attached to the control subsystem 136 (i.e., may be attached to the printed circuit board 128). The connectors and contact strips may comprise any suitable conductive material or materials, such as but not limited to stainless steel, titanium, copper, nickel, brass, zinc, or the like, which may in some instances be gold-plated.

It should be appreciated that the stimulator body and stimulator probe may additionally or alternatively be inductively coupled, such that power may be transferred from the stimulator body to the stimulator probe via induction. In these variations, the stimulator body and stimulator probe may each comprise a coil. In some variations, each of the coils may be wrapped around a ferromagnetic (e.g., iron) core, but need not be. In some variations, the coil of the stimulator body and/or stimulator probe may be a printed coil.

Other variations and mechanisms for physical and electrical connection between the stimulator body and stimulator probe are described in U.S. application Ser. No. 14/256,915, filed Apr. 18, 2014, and titled "NASAL STIMULATION DEVICES AND METHODS," which was previously incorporated by reference in its entirety.

In some variations, some or all of the stimulator may be disposable. In variations where the stimulator body is permanently attached to the stimulator probe, the entire stimulator may be disposable. In other variations, one or more portions of the stimulator may be reusable. For example, in variations where the stimulator probe is releasably connected to the stimulator body, the stimulator body may be reusable, and the stimulator probe may be disposable. As such, the stimulator probe may be periodically replaced. In yet other variations, a portion of the stimulator probe may be disposable (e.g., the stimulator probe may comprise disposable sleeves or disposable prongs) and may be periodically replaced. In some variations, the stimulators described here may comprise features that encourage or require a user to replace a stimulator or stimulator components after a certain period or on a regular basis in order to main proper hygiene.

In variations in which the entire stimulator is disposable (e.g., when the stimulator probe is integrally formed with or permanently attached to the stimulator body), the stimulator may be configured to become non-operational after a certain period of time and/or use. In some of these variations, the stimulator may be configured to limit the duration of stimulation that may be provided by the stimulator; after the duration limit, the stimulator may be configured to become non-operational. For example, the stimulator may have a power source that is only sufficient to power stimulus delivery for a predetermined duration (e.g., one hour of stimulation). Once the power source has been depleted, a user may need to replace the spent stimulator with a new stimulator. In some of these variations, the stimulator may be configured such that the power source cannot be accessed without rendering the device inoperable, which may help prevent users from replacing the power source.

As another example, the stimulator additionally or alternatively may be programmed to limit the duration or amount of stimulus delivery with a given stimulator. In some of these variations, the stimulator may be configured to measure and store the duration of stimulation provided by the stimulator over time (which may be cumulatively added over a plurality of different treatment sessions). When the duration reaches a threshold limit (e.g., about 10 minutes, about 30 minutes, about one hour, about 2 hours, or longer than 2 hours), the stimulator may be programmed to switch to an inoperable state, whereby the stimulator may not be activated to provide additional stimulation. As another example, the stimulator additionally or alternatively may be configured to limit the number of treatment sessions provided by the stimulator. In some of these variations, the stimulator may be configured to measure and store the number of treatment sessions provided by the stimulator. When the number of treatment sessions reaches a threshold limit (e.g., five uses, ten uses, fifteen uses, or more than fifteen uses), the stimulator may be programmed to switch to an inoperable state, whereby the stimulator may not be activated to provide additional stimulation.

In these or other variations in which the entire stimulator is disposable, the stimulator may additionally or alternatively be configured to become non-operational after a certain period of time after its first use. The stimulator may be configured to limit the duration since the first use of the stimulator; after the duration limit, the stimulator may be configured to become non-operational. In some of these variations, the stimulator may be configured to store date and time information regarding the first use of the stimulator. The stimulator may be further configured to switch to an inoperable state when a predetermined amount of time (e.g., one day, two days, five days, one week, two weeks, or longer than two weeks) has passed from the first use of the stimulator.

In any of these variations, the stimulator may be configured to limit the duration of stimulus delivery, the number of treatment sessions, or the duration since first use via a control subsystem, which may in some instances comprise intelligence such as a microcontroller, programmable logic (e.g., a field-programmable gate array), or an application-specific integrated circuit (ASIC) configured to measure, store, and limit the duration and/or number of treatment sessions and/or the time since first use of the stimulator. In any of these variations, when the device moves to an inoperable state, the user may need to replace the inoperable stimulator with a new stimulator.

In variations in which the stimulator body is reusable and all or a portion of the stimulator probe is disposable, the stimulator may be configured to encourage and/or require the user to replace all or a portion of the stimulator probe. In some of these variations, the disposable portion probe or portion of the probe may comprise a recyclable material. In some of these variations, the stimulator may be configured such that the stimulator probe or a portion thereof becomes inoperable after being attached to the stimulator body for a predetermined amount of time (e.g., between about 1 hour and about 24 hours, between about 1 day and about 7 days, between about 1 week and about 4 weeks, between about 1 month and about 3 months, or longer than about 3 months), after a predetermined number of treatment sessions, and/or after a predetermined duration of stimulation (e.g., between about 2 minutes and about 30 minutes, between about 30 minutes and about 1 hour, between about 1 hour and about 3 hours, between about 3 hours and 12 hours, or longer than about 12 hours).

For example, in some variations of stimulators comprising one or more electrodes, the electrodes of the stimulator probe may become inoperable after being attached to the stimulator body for a predetermined amount of time, after a predetermined number of treatment sessions, and/or after a predetermined duration of stimulation. For example, in some variations it may be desirable to promote oxidation of one or more of the electrodes during stimulation. In these variations, the electrode may be configured to form a non-conductive (or reduced conductivity) layer on the surface of the electrode. In some variations, this may interfere with the ability of the electrode to stimulate tissue, and eventually the oxide layer may substantially prevent any electrical energy from being supplied to the user. In some instances, to form such a layer, the stimulator may be configured to deliver biphasic pulses using the electrodes, wherein the biphasic pulses are not charge-balanced. By not charge-balancing the stimulation pulses, charge may accumulate on one or more of the electrodes and/or leads, which may facilitate oxidation of the metal of the electrode and/or lead. The rate of the oxidation may be controlled at least partially by the materials of the electrode and/or lead and the parameters of the pulses delivered by stimulator, and the rate of oxidation may be tailored to achieve a predetermined treatment duration or number of treatment sessions before formation of an oxide layer may render the stimulator inoperable. As another example, in some variations, an electrode of a stimulator probe additionally or alternatively may be configured to change color over time (e.g., as a result of delivering stimulation, as a result of carbon dioxide exposure, as a result of oxidation), such that a user may be prompted to change the stimulator probe when the electrode reaches a certain color. In these variations, the stimulator probe or a portion of the stimulator probe (e.g., nasal insertion prongs or sleeves comprising the electrodes) may be replaced when the electrodes of the stimulator probe are unable to provide stimulation or when the stimulator encourages replacement via the color change.

As yet another example, in some variations the stimulator may be programmed to render the stimulator probe inoperable and/or to encourage replacement of the stimulator probe or a portion thereof (e.g., disposable prongs or sleeves) after being attached to the stimulator body for a predetermined amount of time, after a predetermined number of treatment sessions, and/or after a predetermined duration of stimulation. In some of these variations, the stimulator may be programmed to measure the duration of stimulation provided using a specific stimulator probe or portion thereof, the number of treatment sessions provided using a specific stimulator probe or portion thereof, and/or the duration of attachment of a specific stimulator probe or portion thereof to the stimulator, via mechanisms described in more detail herein. In variations where the stimulator is programmed to measure multiple of the above-listed parameters, if the measurement reaches a threshold value, the stimulator may be configured to alert the user and/or to enter an inoperable state until the current stimulator probe or portion thereof is replaced. In variations where the stimulator is programmed to measure multiple of the above-listed parameters, the stimulator may be configured to alert the user and/or enter the inoperable state when any of the measured parameters reaches its threshold value, or the stimulator may require multiple of the measured parameters to reach their corresponding threshold values in order to alert the user and/or enter an inoperable state. The stimulator may alert the user in any suitable manner, including visual feedback (e.g., generating a prompt on a display, activating a LED, notifying the user on another device, such as a computer or mobile device, or the like), audio feedback (e.g., generating one or more beeps or audio prompts), and/or tactile feedback (e.g., vibrating the stimulator). Similarly, in variations in which the stimulator has entered its inoperable state, the stimulator may additionally or alternatively be configured to instruct the user to replace the stimulator probe. This may also be done in any suitable manner, including visual, audio, or tactile feedback.

Additionally or alternatively, in some variations the stimulator may be configured to alert the user and/or enter an inoperable state when a used stimulator probe is attached to the stimulator body. The stimulator may alert the user in any suitable manner, and may additionally or alternatively be configured to instruct the user to replace the stimulator probe, as described herein. In these variations, the stimulators may comprise a mechanism for determining whether the attached stimulator probe is new (i.e., whether the stimulator probe has been previously attached to a stimulator body or not). In some variations, the mechanism for determining whether the stimulator probe is new may comprise a fuse. In some variations, the fuse may temporarily short circuit the stimulator circuitry while the probe is being connected to the stimulator body.

One or more mechanisms for determining when a stimulator probe is attached may also be used in some variations to render the stimulator probe inoperable and/or to encourage replacement of the stimulator probe or a portion thereof (e.g., disposable prongs or sleeves) after a predetermined number of treatment sessions, and/or after a predetermined duration of stimulation. In some of these variations, attachment of the stimulator probe may be registered using one or more of these mechanisms, and the stimulator may be programmed to measure the duration of stimulation or number of treatment sessions provided using that stimulator probe. The stimulator may be configured to do so via intelligence in a control subsystem, such as a microcontroller, programmable logic (e.g., a field-programmable gate array), or an application-specific integrated circuit (ASIC).

In some variations, the stimulators described here may be configured such that it may be necessary to replace a disposable stimulator probe in order to recharge the stimulator or to replace a power supply of the stimulator. For example, in some variations where the stimulator comprises one or more electrical contacts or ports configured to connect to an external power source, the stimulator probe may be configured to cover or otherwise block access to the electrical contacts/ports when the stimulator probe is connected to the stimulator body. In these variations, it may be necessary to remove the stimulator probe to provide access to the electrical contacts/ports (which may in some variations disable the stimulator probe, as described in more detail below). Similarly, in variations where the stimulator body includes a replaceable power source (e.g., one or more batteries), the stimulator probe may block access to the replaceable power source such that the stimulator probe may need to be disconnected from the stimulator body prior to replacing the power source.

In variations where a stimulation system comprises a base station (as described in more detail herein), a stimulator may be configured such that the stimulator cannot be connected to the base station while a stimulator probe is attached to the stimulator body. For example, in the variations of the stimulation systems shown in FIGS. 10A-10D described in more detail herein, the base station may comprise a recess sized and configured to receive the stimulator body to operationally connect the stimulator body to the base station. Specifically, the recess may be sized such that the stimulator body can fit within the recess when the stimulator probe is disconnected from the stimulator body (as illustrated in FIG. 10A), but is prevented from fitting in the recess when the stimulator probe is attached to the stimulator body. In these variations, it may be necessary to first disengage the stimulator probe. Accordingly, to utilize one or more functions of the base station, a user may need to first decouple a stimulation probe from the stimulator body before connecting the stimulator body to the base station. In some variations, the stimulator probe may comprise a lockout mechanism that prevents the stimulator probe from being reconnected to the stimulator body after being disconnected from the stimulator body. For example, the stimulator may be configured such that the stimulator probe is disabled when disengaged from the stimulator body (e.g., when the probe is disengaged from the stimulator body in order to connect the stimulator body to the base station). This may prevent the stimulator probe from being reused.

It should be appreciated that any suitable method may be used to determine whether and for how long a stimulator probe is attached, to alert the user and/or enter an inoperable state when a used stimulator probe is attached to the stimulator body, and/or to render the stimulator probe inoperable and/or to encourage replacement of the stimulator probe or a portion thereof, including the methods and mechanisms described in U.S. application Ser. No. 14/256,915, filed Apr. 18, 2014, and titled "NASAL STIMULATION DEVICES AND METHODS," which was previously incorporated by reference in its entirety.

Cap & Case

Figure 9B:
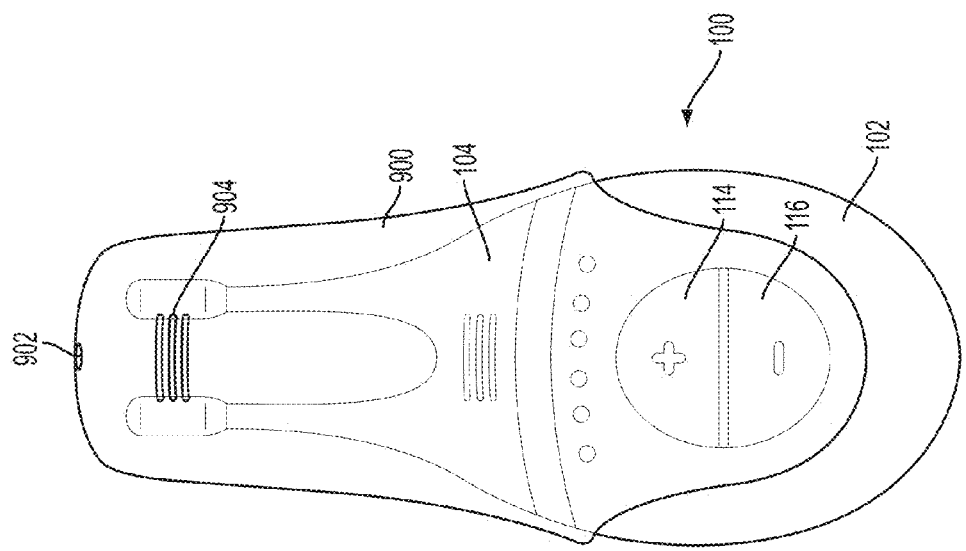
FIGS. 9A and 9B show perspective and front views, respectively, of the handheld stimulator of FIGS. 1A-1E with an attached cap.
Figure 9A:
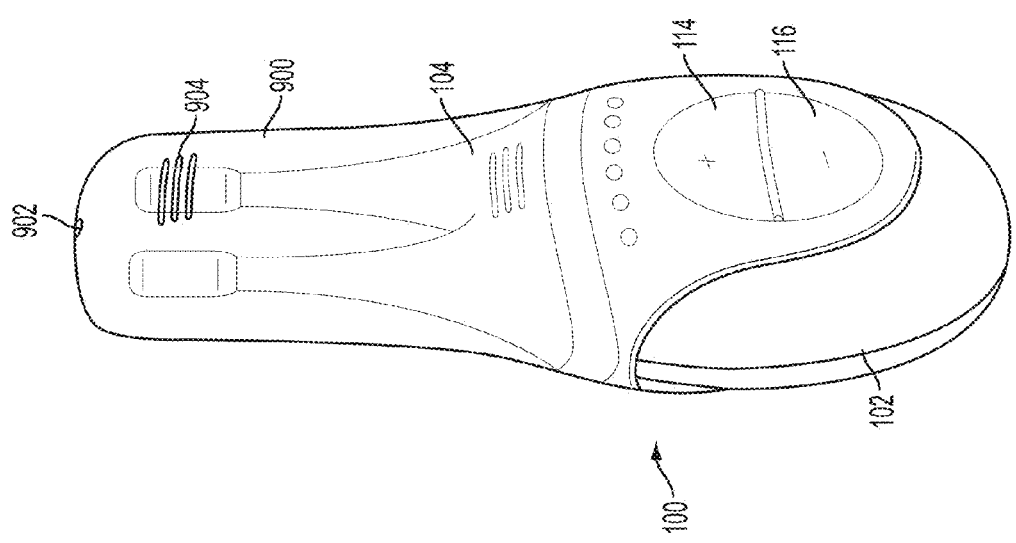

In some variations, the stimulators described here may comprise a cap to protect the stimulator probe. For example, FIGS. 9A and 9B show perspective and front views, respectively, of stimulator 100 with an attached cap 900. As shown there, the cap 900 may fit over the stimulator probe 104, which may protect the probe from contamination. More particularly, it may be desirable for the cap to protect the nasal insertion prongs, and especially the electrodes, from contamination. The cap 900 may have any suitable shape. In some variations, the cap 900 may cover the operating mechanisms when attached to the stimulator. This may prevent the operating mechanisms from being inadvertently or accidentally manipulated. As shown in FIGS. 9A-9B, the cap 900 may cover the buttons 114 and 116 of the stimulator body 102, while leaving the sides of stimulator body 102 exposed. This may allow a user to more easily grip the stimulator body 102 in order to remove the cap 900. In some variations the cap may comprise a texturized surface or other gripping features to assist with removal, such as ridges 904 shown on cap 900. The cap or other enclosure may comprise any suitable material or materials, such as a plastic or synthetic resin. In some variations the cap or other enclosure may be translucent or transparent, while in other variations it may be opaque.

The cap or other enclosure may in some variations comprise one or more features to control the exposure of the stimulator probes to the air. When the probes comprise a hydrogel or other liquid or wet material, the amount of exposure of air may affect the rate at which the hydrogel or other liquid or wet material dries out. For example, in some variations the caps may comprise one or more openings to allow for air flow underneath the cap or other enclosure. Cap 900, for example, may comprise an opening 902 at the distal end of the cap. In some variations the cap may be generally conformed to the shape of the stimulator probe (e.g., by comprising recesses having shapes corresponding to the stimulator prongs' shape and configured to receive the prongs), such that the air within the cap is minimal; in other variations, the cap may not be conformed to the shape of the stimulator probe, such that there is more air circulating within the cap around the stimulator probe.

Figure 9C:
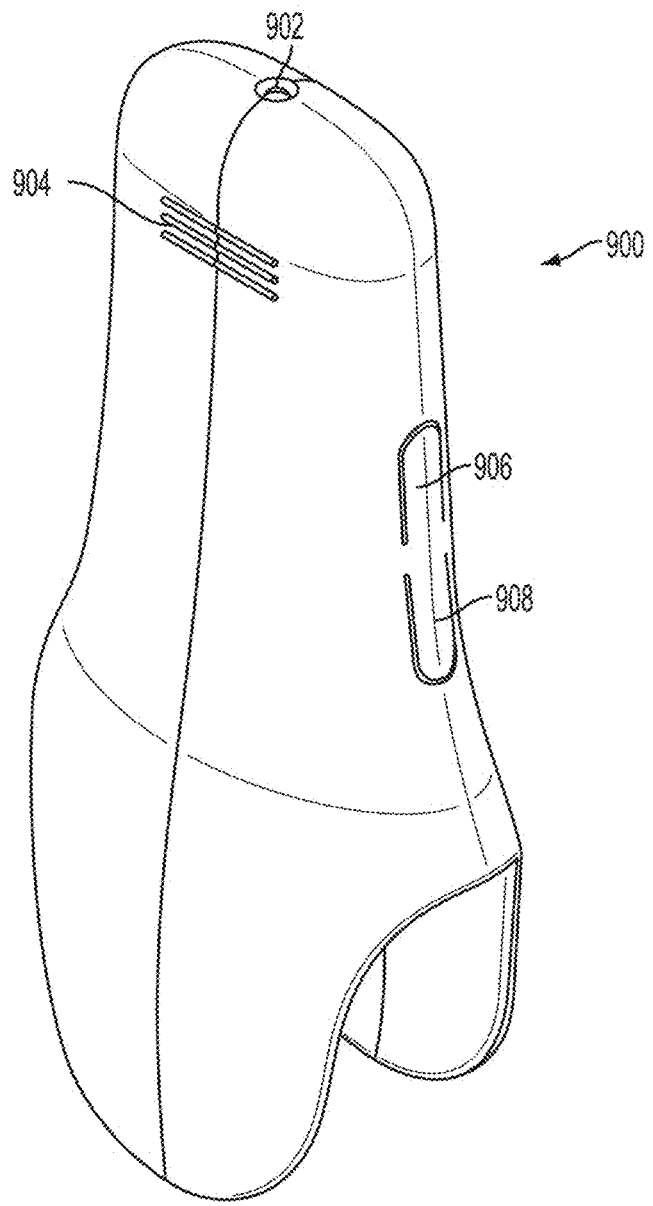
FIG. 9C shows a perspective view of a cap.

In some variations, the cap may comprise one or more features to promote attachment of the cap to the stimulator body. For example, in some variations the cap may comprise tabs or bosses, which may be configured to mate with indentations or cavities on the stimulator. Additionally or alternatively, the stimulator may comprise tabs or bosses, which may be configured to mate with indentations or cavities on the cap. In some of these variations, the flexibility of the cap material may allow cap to be placed on the stimulator. Additionally or alternatively, the cap may comprise one or more living hinges or cutaways 906 and 908, such as shown in FIG. 9C. The living hinges or cutaways may allow the cap to flex in order to slide past a raised feature on the stimulator (e.g., a tab or boss); for example, squeezing the top cutaway 906 may cause the bottom portion 908 to rotate away from the stimulator, allowing the bottom portion 908 to slide past a raised feature when attaching or removing the cap 900. Additionally or alternatively, the cap material and/or shape may promote attachment of the cap to the stimulator body. For example, the cap may be flexible in order to flex to slide over a thicker portion of the stimulator while being attached, and then the cap may relax into a conformal position upon reaching a thinner portion of the stimulation.

Other variations and features of caps or enclosures, as well as cases configured to hold stimulators, are described in U.S. application Ser. No. 14/256,915, filed Apr. 18, 2014, and titled "NASAL STIMULATION DEVICES AND METHODS," which was previously incorporated by reference in its entirety.

Base Station

In some variations, the stimulation systems described here may comprise a base station configured to connect to a portion of the stimulator, the stimulator having a stimulator body and a stimulator probe. The base station may be configured to releasably connect to one or more portions of the stimulator, and may be configured to perform one or more functions when connected to the stimulator. FIGS. 10A-10D depict a portion of a stimulator system comprising a base station 1000 as described here. FIG. 10A shows a front view the stimulator body 1002 docked in the base station 1000, while FIGS. 10B, 10C, and 10D depict side, back, and top views of the base station 1000, respectively. The stimulator body 1002 and stimulator probe (not shown) may include any of the elements of the stimulators described herein. In variations where the stimulator body 1002 comprises a rechargeable power source (such as a rechargeable battery, capacitor, or the like), the base station 1000 may be configured to recharge the rechargeable power source. For example, the base station 1000 may comprise one or more electrical contacts 1004, which may be configured to electrically connect to corresponding electrical contacts on the stimulator body 1002. In some variations, these electrical contacts may be the same electrical contacts that connect the stimulator probe and the stimulator body (e.g., electrical contacts similar to connectors 122 and 124 of stimulator 100). This electrical connection may allow the base station 1000 to charge the power source of the stimulator body 1002.

In some variations, the base station may comprise a safety mechanism that prevents power delivery to the electrical contacts unless the stimulator is connected. For example, the base station may comprise a sensor configured to detect the stimulator. After the stimulator is detected, power may be delivered to the contacts. In one variation, the sensor may comprise a magnetic field sensor (e.g., a Hall effect sensor), and the stimulator may comprise a magnet. When the stimulator is placed in the base station, the magnetic field sensor may detect the presence of the magnet in the stimulator and may in turn cause power to be delivered to the contacts.

It should be appreciated that in other variations, the base station may additionally or alternatively be configured to inductively charge the stimulator. For example, the base station may comprise a primary coil, which may or may not be wrapped around a ferromagnetic (e.g., iron) core, and the stimulator body may comprise a secondary coil, which may or may not be wrapped around a ferromagnetic core. When the stimulator body is placed in the base station, the coils and iron cores may form a complete transformer, allowing power to be inductively transferred from the base station to the stimulator body. Additionally or alternatively, it should be recognized that inductive power transfer may also be used to transfer power from the stimulator body to the stimulator probe.

The base station may be powered in any suitable manner. In some variations, the base station may be connectable to an external power source (e.g., a wall outlet or separate battery back), which may provide power to the stimulator and/or the base station. In some variations, the base station may comprise a power cable, which may be permanently attached via a strain relief. In other variations, such as the variation of the base station 1000 shown in FIGS. 10A-10D, the base station may comprise a port 1006 (e.g., a USB port or micro-USB port), which may connect the base station 1000 to an external power source. It should be appreciated that the base station 1000 may include any suitable port or connector for connecting the base station to an external power source. Additionally or alternatively, the base station may comprise a power source (e.g., one or more batteries) operable to power the base station 1000 (and to recharge the stimulator in variations where the stimulator is rechargeable). The power source may or may not be rechargeable.

The base station 1000 may be configured to rest on a surface (e.g., a counter or table), and may comprise a weight and/or a bottom surface with increased friction (e.g., a rubber pad 1008) to help keep the base station 1000 in place. In variations in which the stimulator comprises a magnet or material attracted to a magnetic field (e.g., iron, nickel, cobalt, alloys thereof and the like), the base station may comprise a magnet in a corresponding location in order to hold the stimulator in place within the base station. For example, the base station may comprise a magnet located between the electrical contacts, which may be configured to attract a magnet in the stimulator body (e.g., in a base station configured to receive stimulator body 102, the base station may comprise a magnet configured to attract the magnet 134 attached to the interior of proximal housing 142.).

Figure 8:
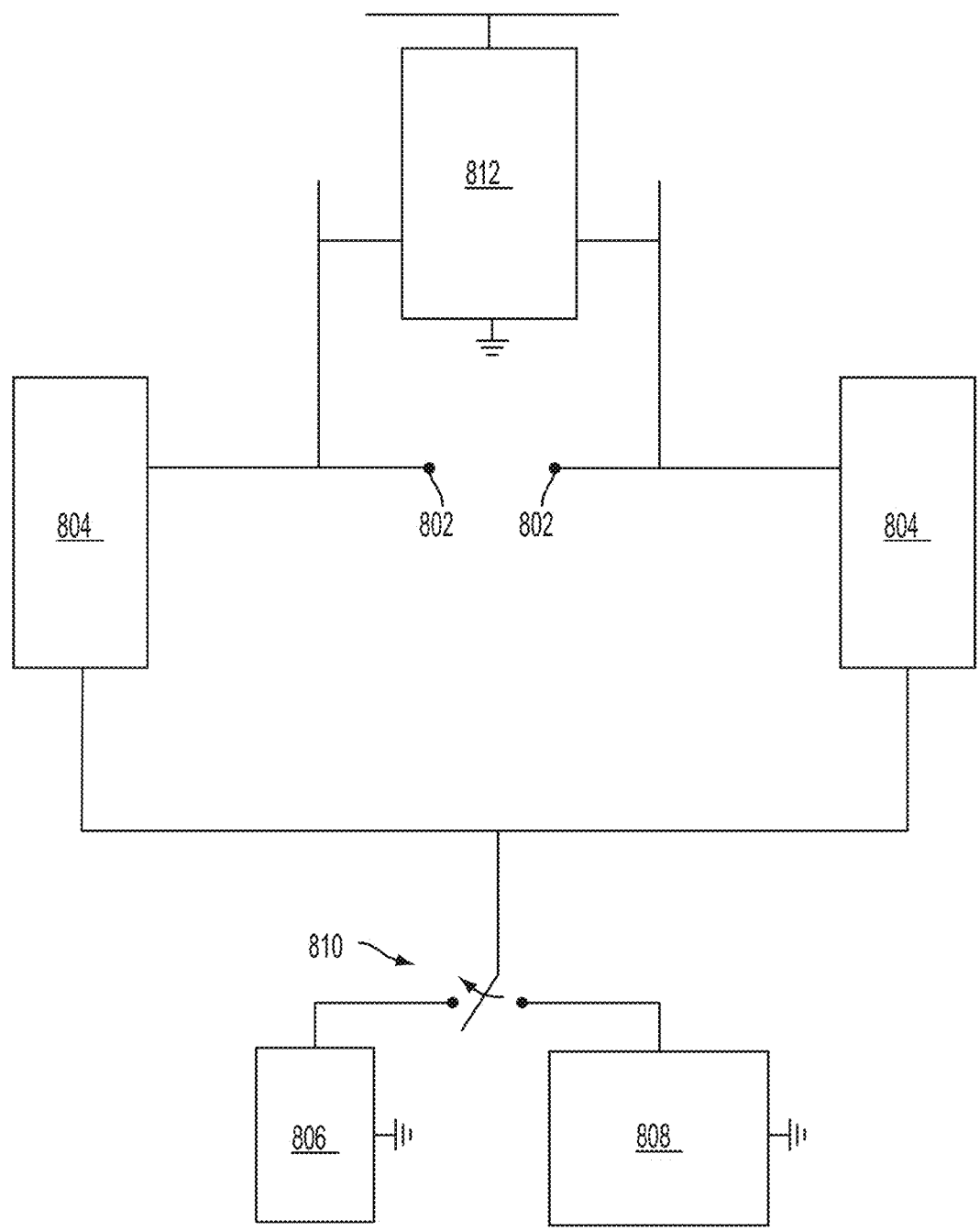
FIG. 8 illustrates a schematic diagram of stimulator circuitry.

In instances where the stimulator is configured to record or otherwise store data (e.g., the frequency or duration of stimulation), the base station may be configured to retrieve data from the stimulator. For example, in variations where the stimulator and base station are configured to be electrically connected, data may be transmitted via this electrical connection (e.g., the connection between connectors 122 and 124 of stimulator body 102 and electrical contacts 1004 of base station 1000). FIG. 8 illustrates a schematic diagram of stimulator circuitry allowing for the same pins 802 to be used to transfer data from the stimulator body to the base station, to transmit a stimulus from the stimulator body to the stimulator probe, and to charge a rechargeable power source in the stimulator body using the base station. As shown, the pin drivers 804 may take input signals either from a data communication subsystem 806 or a stimulation subsystem 808. The input to the drivers 804 may be determined by a switch 810. In some variations, the switch 810 may comprise a gate, state machine, or a micro-controller. The pins 802 may also be used to charge the stimulator. A rectification circuit 812 may be configured to rectify a charging input signal without interfering with any output stimulation or data waveform. In some variations, the rectification circuit may comprise a full wave rectifier comprising rectification diodes, but it should be appreciated that any suitable circuit may be used. Time blocks for each function may be synchronized in order for the system to perform each function.

Other variations and features of base stations are described in U.S. application Ser. No. 14/256,915, filed Apr. 18, 2014, and titled "NASAL STIMULATION DEVICES AND METHODS," which was previously incorporated by reference in its entirety.

In some variations the stimulators described here may be configured to connect to an external device, such as a mobile device (e.g., a cellular telephone, a tablet, a wearable computer (e.g., optical head-mounted displays such as Google GLASS™ wearable computing device), or the like), a computer, or the like. The stimulators may be configured to connect to an external device through any suitable connection method. In some variations the connection method may be wireless (e.g., via Wi-Fi, BLUETOOTH™ wireless technology, or the like), and the stimulator may comprise an antenna or the like. Additionally or alternatively, the connection method may be via a wired transmission line. In these variations, the stimulator may comprise one or more ports (e.g., a USB port), connectors and/or cables configured to physically connect the stimulator to an external device. In some variations, the stimulators may use a wireless or wired connection to connect to the internet, via which they may be connected to an external device. In these variations, the device may be at a distant location (e.g., at the manufacturer, at a physician's office, or the like).

In instances in which the stimulators are configured to connect to an external device, the device may be configured to perform one or more operations associated with the stimulator. For example, in variations where the stimulator is configured to collect data (e.g., one or more subject parameters, stimulation timing or parameters, stimulator diagnostic information, such as described in more detail herein) and store that data in a memory unit of the stimulator, connection of the stimulator to the device may allow for transfer of data stored in the stimulator's memory unit to the device. Specifically, the device and stimulator may be programmed such that upon connection of the device and the stimulator, the device may download the recorded data stored in the stimulator's memory. In some variations, once data has been transferred from the stimulator to the device, the stimulator may be configured to delete this data from the stimulator memory. Because the amount of memory available in the device may be greater than that in the stimulator, this transfer may increase the data that may be accumulated for a subject.

In addition to or instead of transferring data stored in the stimulator memory, a device may be configured to collect and store real-time data from the stimulator when the two are connected. In some of these variations, the stimulator may also be configured to store this data in the stimulator memory. In some instances, the device may be configured to transmit data (e.g., via internet connection, cellular data network, or the like) from the device to an external location (e.g., to a database where the data may be analyzed, to a physician's office to allow the physician to monitor the data and, in some instances, provide feedback).

In some variations, the device may be configured to solicit input from a user. For example, if the stimulator is used to provide stimulation while attached to a device, the device may be configured to solicit the user to input data regarding the subject's experience (e.g., a subject's level of comfort/discomfort, status of subject's symptoms). In some variations, the device may be configured to present data (and/or analysis of the data) to a user. For example, the device may be configured to display information regarding the frequency of stimulation, the average duration of stimulation, a graph of subject comfort levels over time, or the like. In some variations, the device may be configured to share the data or analysis of the data with the manufacturer, clinicians, friends, or others.

It should be appreciated that while certain handheld stimulators have been described herein, handheld stimulators for use in the methods described herein may have any suitable configuration. In addition to those described herein and in U.S. application Ser. No. 14/256,915, filed Apr. 18, 2014, and titled "NASAL STIMULATION DEVICES AND METHODS," which was previously incorporated by reference in its entirety, additional handheld stimulators suitable for use in the methods described herein are described in U.S. patent application Ser. No. 14/920,860, filed Oct. 22, 2015, and titled "STIMULATION DEVICES AND METHODS FOR TREATING DRY EYE," which is hereby incorporated by reference in its entirety. Furthermore, while handheld stimulators have been described above, it should be appreciated that in other variations of the stimulation systems described here, the stimulation system may comprise a stimulator configured to be implanted, either permanently or temporarily, in a subject. It should be appreciated that the implantable stimulators need not be surgically implanted. In some of these instances, the implantable stimulator may be configured such that the stimulator may be inserted and/or removed by a user. In others of these instances, the implantable stimulator may be configured to be inserted and/or removed by a medical professional. In other instances, the stimulator may be configured to be implanted in or otherwise attached to tissue within a nasal or sinus cavity. Variations and features of implantable stimulators are described in U.S. application Ser. No. 14/256,915, filed Apr. 18, 2014, and titled "NASAL STIMULATION DEVICES AND METHODS," which was previously incorporated by reference in its entirety, and in U.S. patent application Ser. No. 14/920,852, filed Oct. 22, 2015, and titled "IMPLANTABLE NASAL STIMULATOR SYSTEMS AND METHODS," which is hereby incorporated by reference in its entirety.

Stimulation Methods

Generally, the stimulators and stimulation systems described herein may be configured to stimulate nasal or sinus tissue. In some variations, the stimulation may be used to treat allergic rhinitis, non-allergic rhinitis, nasal congestion, ocular allergy, and/or symptoms associated with these conditions. Generally, a stimulator (such as described above) may be configured to stimulate trigeminal afferent nerve fibers to activate the nasolacrimal reflex, which may in turn reduce the symptoms associated with these conditions. In some of these instances, the methods described herein may comprise stimulating the anterior ethmoidal nerve. In other instances, the methods may comprise stimulating the internal branches of the infraorbital nerve, the superior branches of the greater palatine nerve, the septal nerve, and/or the posterior superior lateral nasal branches of the maxillary nerve.

Location

Figure 4B:
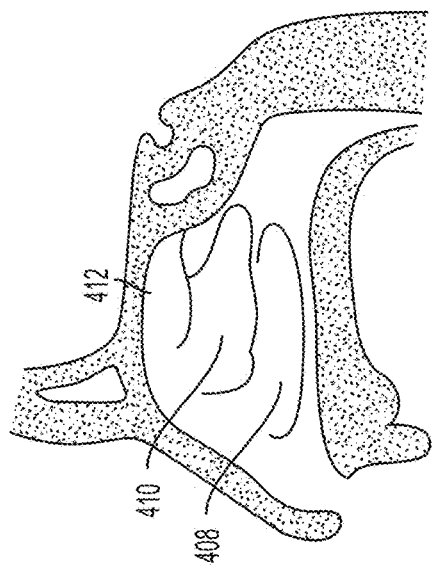
FIGS. 4A-4C illustrate relevant anatomical locations.
Figure 4C:
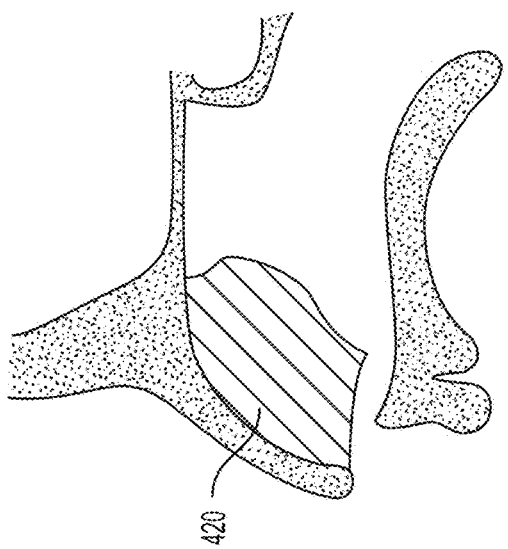
Figure 4A:
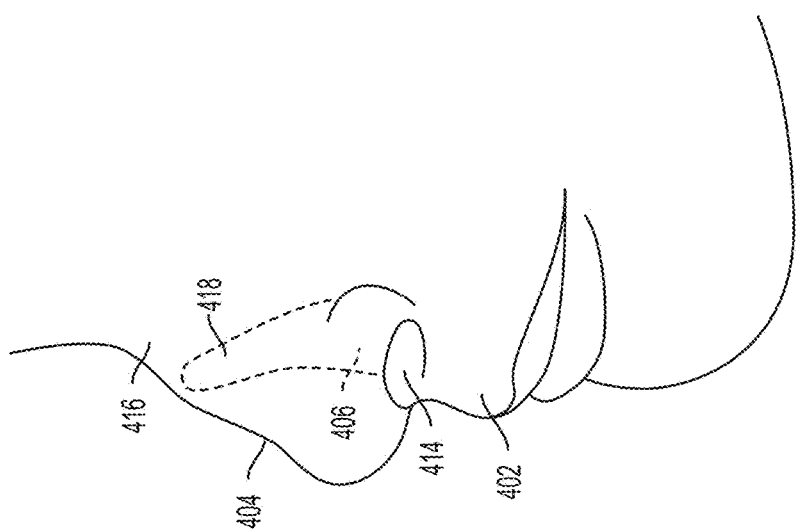

When an implantable stimulator is used to provide stimulation, the implantable stimulator may be positioned in a nasal or sinus cavity (or multiple nasal or sinus cavities). When a handheld stimulator is used to provide stimulation, one or more prongs of the stimulator may be inserted at least partially into the nose of a user, and a stimulation signal (such as described herein) may be delivered to the mucosal tissue. A portion of the nasal insertion prong(s) may be positioned and/or manipulated to be placed in contact with any suitable tissue. In variations in which the stimulators are configured to deliver an electrical stimulus, the stimulators may be positioned and/or manipulated to position electrodes into contact with any suitable tissue. FIGS. 4A-4C illustrate certain anatomical locations. For example, the nasal insertion prong(s) may be placed in contact with the upper lip 402, external nasal skin 404, nasal ala 406, mucosa of a nasal turbinate (e.g., one or more of the inferior 408, medial 410, or superior turbinates 412), or the like. When the stimulators are used to treat nasal congestion, allergic rhinitis, non-allergic rhinitis, ocular allergy, and/or symptoms associated with these conditions, it may in some instances be desirable to position a portion of the nasal insertion prongs (e.g., an electrode) in contact with the nasal mucosa of a nasal turbinate (e.g., a middle and/or superior nasal turbinate). In some instances, the targeted area may comprise tissue innervated by the anterior ethmoidal branch of the nasociliary nerve, as shown by shaded area 420 in FIG. 11C. In other instances when the stimulators are used to treat nasal congestion, allergic rhinitis, non-allergic rhinitis, ocular allergy, and/or symptom associated with these conditions, the targeted area may comprise tissue innervated by the internal branches of the infraorbital nerve; tissue innervated by superior branches of the greater palatine nerve; tissue innervated by the septal nerve; tissue innervated by the posterior superior lateral branches of the maxillary nerve; and/or two or more of these areas. In some instances, the targeted area of the nasal mucosa may be superior to the columella 414. In some of these instances, the targeted area may be near the inferior end of the nasal bone 416 (i.e., near the interface between the nasal bone 416 and the upper lateral cartilage 418). In other variations, the targeted area may be the columella. In some variations, it may be desirable to place a portion of the nasal insertion prong(s) (e.g., an electrode) between about 20 mm and about 60 mm into the nasal cavity of the subject. In some of these variations, it may be desirable to place an electrode between about 20 mm and about 35 mm into the nasal cavity of the subject. In some of these variations, it may be desirable to place an electrode between about 25 mm and about 35 mm into the nasal cavity of the subject. In some variations, it may be desirable to place an electrode between about 30 mm and 40 mm into the nasal cavity of the subject. In some variations, it may be desirable to place an electrode between about 25 mm and about 40 mm into the nasal cavity of the subject. In some variations, it may be desirable to place an electrode between about 20 mm and about 40 mm into the nasal cavity of the subject. In some variations, it may be desirable to place and electrode between about 8 mm and about 20 mm into the nasal cavity of the subject. In some variations, it may be desirable to place an electrode less than about 30 mm into the nasal cavity of the subject, less than about 35 mm into the nasal cavity of the subject, or less than about 40 mm into the nasal cavity of the subject.

As described herein, it may in some instances be desirable to direct the nasal insertion prongs such that a portion (e.g., the electrodes) is directed toward the front of the nose. This may allow for selective activation of nerves in the front of the septum (e.g., the ophthalmic branch of the trigeminal nerve) while minimizing activation of nerves toward the rear of the nasal septum, which may reduce negative side effects that may occur from stimulation of nerves that innervate the teeth. It may also in some instances be desirable to direct the nasal insertion prongs so as to reduce negative side effects that may occur from stimulation of the olfactory area. In other variations when the stimulators are used to treat nasal congestion, allergic rhinitis, non-allergic rhinitis, ocular allergy, and/or symptoms associated with these conditions, it may be desirable to direct the nasal insertion prongs such that a portion (e.g., the electrodes) is directed toward the septum. In yet other variations when the stimulators are used to treat nasal congestion, allergic rhinitis, non-allergic rhinitis, ocular allergy, and/or symptoms associated with these conditions, it may be desirable to direct the nasal insertion prongs such that a portion (e.g., the electrodes) is directed outward and away from the septum.

Electrical Stimulus

In some variations, the stimulation may be delivered unilaterally (e.g., in a single nostril). For example, in variations where a stimulator comprises a single prong, the prong may be placed in a first nostril, and stimulation may be delivered to the first nostril via the prong. It should be appreciated that in some of these variations in which the stimulus is electrical, a pad electrode or other return electrode may be temporarily affixed to or otherwise be placed in contact with an external portion of the nose to act as a return electrode. In some variations where a stimulator comprises two or more prongs, each of the prongs may be placed in a first nostril, and some or all of the prongs may be used to deliver stimulation to mucosal tissue. In other variations where a stimulator comprises two or more prongs, at least one prong may be positioned in a first nostril, and at least one prong may be positioned in a second nostril. In variations in which the stimulus is electrical, some or all of the prongs in the first nostril may be used to deliver unilateral electrical stimulation to the first nostril (e.g., the prongs in the second nostril may remain inactive), or some or all of the prongs in the second nostril may be used to deliver unilateral electrical stimulation to the second nostril.

In some variations, the stimulator may be used to provide bilateral stimulation of the mucosal tissue. In these variations, at least one prong of the stimulator may be positioned in a first nostril and at least one prong of the stimulator may be positioned in a second nostril. In these variations, when the stimulus is electrical, electrical stimulation may be delivered between the prongs in the first nostril and the prongs of the second nostril, which may cause current to flow through the septum.

When the stimulus is electrical, the electrical stimulus delivered by the stimulators described here may include a waveform or waveforms, which may be tailored for specific treatment regimens and/or specific subjects. The waveforms may be pulse-based or continuous. It should be appreciated that the waveforms described here may be delivered via a bipolar configuration or a monopolar configuration. When the stimulator is configured to deliver a continuous waveform, the waveform may be a sinusoidal, quasi-sinusoidal, square-wave, sawtooth/ramped, or triangular waveform, truncated-versions thereof (e.g., where the waveform plateaus when a certain amplitude is reached), or the like. Generally, the frequency and peak-to-peak amplitude of the waveforms may be constant, but in some variations the stimulator may be configured to vary the frequency and/or amplitude of the waveform. This variation may occur according to a pre-determined plan, or may be configured to occur randomly within given parameters. For example, in some variations the continuous waveform may be configured such that the peak-to-peak amplitude of the waveform varies over time (e.g., according to a sinusoidal function having a beat frequency). In some instances varying the amplitude and/or frequency of a stimulation waveform over time, or pulsing the stimulus on and off (e.g., 1 second on/1 second off, 5 seconds on/5 seconds off), may help reduce subject habituation (in which the subject response to the stimulation decreases during stimulation). Additionally or alternatively, ramping the amplitude of the stimulation waveform at the beginning of stimulation may increase comfort.

When the stimulator is configured to create a pulse-based electrical waveform, the pulses may be any suitable pulses (e.g., a square pulse, a haversine pulse, or the like). The pulses delivered by these waveforms may by biphasic, alternating monophasic, or monophasic, or the like. When a pulse is biphasic, the pulse may include a pair of single phase portions having opposite polarities (e.g., a first phase and a charge-balancing phase having an opposite polarity of the first phase). In some variations, it may be desirable to configure the biphasic pulse to be charge-balanced, so that the net charge delivered by the biphasic pulse is approximately zero. In some variations, a biphasic pulse may be symmetric, such that the first phase and the charge-balancing phase have the same pulse width and amplitude. Having a symmetric biphasic pulse may allow the same type of stimulus to be delivered to each nasal cavity. The pulses of a first phase may stimulate a first side of the nose (while providing a charge-balancing phase to a second side of the nose), while the pulses of the opposite phase may stimulate the second side of the nose (while providing a charge-balancing phase to the first side of the nose). In other variations, a biphasic pulse may be asymmetric, where the amplitude and/or pulse width of the first pulse may differ from that of the charge-balancing phase. Additionally, each phase of the biphasic pulse may be either voltage-controlled or current-controlled. In some variations, both the first phase and the charge-balancing phase of the biphasic pulse may be current-controlled. In other variations, both the first phase and the charge-balancing phase of the biphasic pulse may be voltage-controlled. In still other variations, the first phase of the biphasic pulse may be current-controlled, and the second phase of the biphasic pulse may be voltage-controlled, or vice-versa.

In variations where the waveform comprises a biphasic pulse, the biphasic pulse may have any suitable frequency, pulse widths, and amplitudes. For example, in instances where the stimulators described here are used to treat allergic rhinitis, non-allergic rhinitis, nasal congestion, ocular allergy, and/or symptoms associated with these conditions by stimulating nasal or sinus tissue, the stimulator may be configured to generate a biphasic pulse waveform at a frequency between about 0.1 Hz and about 200 Hz. In some of these variations, the frequency is preferably between about 10 Hz and about 60 Hz. In some of these variations, the frequency is preferably between about 25 Hz and about 35 Hz. In others of these variations, the frequency is preferably between about 50 Hz and about 90 Hz. In some of these variations, the frequency is preferably between about 65 Hz and about 75 Hz. In other variations, the frequency is preferably between about 130 Hz and about 170 Hz. In some of these variations, the frequency is preferably between about 145 Hz and about 155 Hz. In some variations, high frequencies, such as those between about 145 Hz and about 155 Hz may be too high for each pulse to stimulate/activate the target nerves. As a result, the stimulation may be interpreted by the patient to have an element of randomness, which in turn may help to reduce subject habituation.

Similarly, for the treatment of nasal congestion, allergic rhinitis, non-allergic rhinitis, ocular allergy, and/or symptoms associated with these conditions when the stimulus is electrical and the first phase of the biphasic pulse is current-controlled, the first phase may preferably have an amplitude between about 10 µA and 100 mA. In some of these variations, the amplitude may be preferably between about 0.1 mA and about 10 mA. When the first phase of the biphasic pulse is voltage-controlled, the first phase may preferably have an amplitude between about 10 mV and about 100 V. Additionally, the first phase may preferably have a pulse width between about 1 µs and about 10 ms. In some of these variations, the pulse width may preferably be between about 10 µs and about 100 µs. In other variations, the pulse width may preferably be between about 100 µs and about 1 ms.

When an electrical pulse waveform is an alternating monophasic pulsed waveform, each pulse delivered by the stimulator may have a single phase, and successive pulses may have alternating polarities. Generally, the alternating monophasic pulses are delivered in pairs at a given frequency (such as one or more of the frequencies listed above, such as between 30 Hz and 50 Hz), and may have an inter-pulse interval between the first and second pulse of the pair (e.g., about 100 µs, between 50 µs and 150 µs or the like). Each pulse may be current-controlled or voltage-controlled, and consecutive pulses need not be both current-controlled or both voltage-controlled. In some variations where the pulse waveform is charged-balanced, the waveform may comprise a passive charge-balancing phase after delivery of a pair of monophasic pulses, which may allow the waveform to compensate for charge differences between the pulses.

When a stimulator configured to deliver an electrical stimulus is positioned to place an electrode on either side of the nasal septum, alternating monophasic pulses may promote bilateral stimulation of nasal tissue. The pulses of a first phase may stimulate a first side of the nose (while providing a charge-balancing phase to a second side of the nose), while the pulses of the opposite phase may stimulate the second side of the nose (while providing a charge-balancing phase to the first side of the nose), since nerves may respond differently to anodic and cathodic pulses. The inter-pulse interval may give time for the stimulation provided by a first phase pulse to activate/polarize the target nerves prior to be reversed by an opposite phase pulse.

When a stimulator is configured to deliver a pulse-based waveform, the stimulation amplitude, pulse width, and frequency may be the same from pulse to pulse, or may vary over time. For example, in some variations, the amplitude of the pulses may vary over time. In some variations, the amplitude of pulses may vary according to a sinusoidal profile. In some variations, the stimulation waveform may be a modulated high frequency signal (e.g., sinusoidal), which may be modulated at a beat frequency of the ranges described above. In such variations, the carrier frequency may be between about 100 Hz and about 100 kHz. In other variations, the amplitude of pulses may increase (linearly, exponentially, etc.) from a minimum value to a maximum value, drop to the minimum value, and repeat as necessary. In some variations, the user may be able to control the stimulus during its delivery. After the user has placed a portion of the nasal insertion prong(s) (e.g., the electrode or electrodes) in contact with the nasal tissue, the user may increase the intensity of the stimulus. It may be desirable for the patient to increase the intensity of the stimulus until the stimulus causes paresthesia (e.g., tingling, tickling, prickling). As such, the patient may be able to self-determine the proper stimulation intensity and self-adjust the stimulus to a level effective to achieve the desired result. The desired result or treatment effect may depend on the condition to be treated. For example, the desired result may be relief of symptoms of allergic rhinitis, non-allergic rhinitis, nasal congestion, and/or ocular allergy. In some variations of a method for treatment of allergic rhinitis, for example, the treatment effect may comprise tear and/or mucous production. In some variations of a method for treatment of non-allergic rhinitis, for example, the treatment effect may comprise reduction in thickness and/or volume of lamina propia tissue. It may be desirable for the user to increase the intensity of the stimulus slowly in order to minimize discomfort.

In some instances, it may be desirable to configure the stimulation waveform to minimize side effects. In some instances, it may be desirable to promote stimulation of larger-diameter nerves (e.g., afferent fibers of the trigeminal nerve), which may promote a therapeutic effect, while reducing the stimulation of smaller nerves (e.g., a-delta fibers, c fibers, sympathetic and parasympathetic fibers), which may result in discomfort or mucus production. Generally, for smaller pulse-widths, the activation threshold for larger-diameter nerves may be lower than the activation threshold for the smaller nerve fibers. Conversely, for larger pulse-widths, the activation threshold for larger-diameter nerves may be higher than the activation threshold for the smaller nerve fibers. Accordingly, in some instances, it may be desirable to select a pulse width that preferably actuations the larger-diameter nerves. In some variations, the pulse width may be between 30 μs and about 70 μs, or may be between about 30 μs and about 150 μs. However, it should be appreciated that in some variations, it may be desirable to promote stimulation of nerves of other diameters. In some variations it may be desirable to select a pulse width less than 30 μs, and in other variations it may be desirable to select a pulse width greater than 150 μs.

While certain stimuli have been described herein, it should be appreciated that when used for treating nasal congestion, allergic rhinitis, non-allergic rhinitis, ocular allergy, and/or symptoms associated with these conditions, the stimulation devices described herein may deliver any suitable stimulus, including suitable stimuli described in U.S. application Ser. No. 14/256,915, filed Apr. 18, 2014, and titled "NASAL STIMULATION DEVICES AND METHODS," which was previously incorporated by reference in its entirety, in U.S. application Ser. No. 14/809,109, filed Jul. 24, 2015, and titled "STIMULATION PATTERNS FOR TREATING DRY EYE," which is hereby incorporated by reference in its entirety, and in U.S. application Ser. No. 14/920,860, filed Oct. 22, 2015, and titled "STIMULATION DEVICES AND METHODS FOR TREATING DRY EYE," which was previously incorporated by reference in its entirety. Additionally, although the stimulation systems, devices, and methods described are herein are intended for use with human users, it should be appreciated that they may be modified for veterinary use.

Treatment Regimens

The stimulation methods described herein may be delivered according to one or more treatment regimens to treat a condition.

For example, to treat rhinitis (allergic rhinitis or non-allergic rhinitis), stimulation may in some variations be delivered to a subject as needed and/or according to a pre-determined regimen. In some instances, a user may use one of the stimulation devices described herein to provide a round of stimulation when the user experiences symptoms of allergic rhinitis and/or non-allergic rhinitis, such as but not limited to itching, sneezing, congestion, subject sensation of "fullness," runny nose, post-nasal drip, mouth breathing, coughing, fatigue, headache, anosmia, phlegm, throat irritation, periorbital puffiness, watery eyes, ear pain, or the like. In some variations, a round of stimulation may have a suitable duration, such as but not limited to between about 5 seconds and about 180 seconds, or between about 10 seconds and about 60 seconds. In other variations, a user may deliver a round of stimulation until the user notices an acute reduction in symptoms. When stimulation is delivered on an as-needed basis, a user may deliver any suitable number of rounds of stimulation per day. In some variations, the total number of rounds of stimulation may be limited to 10 per day. In other variations of methods to treat allergic rhinitis or non-allergic rhinitis, the devices described herein may be used to provide stimulation on a scheduled basis. For example, in some variations in which the stimulation devices described herein are used to treat allergic rhinitis or non-allergic rhinitis, a round of stimulation may be delivered between 2 and 10 times per day, for a plurality of days, on a regular pattern. Such a pattern may be, for example, every 12 hours, every 8 hours, every 6 waking hours, every 4 waking hours, every 3 waking hours, every 2 waking hours, every 1.5 waking hours, or the like. In yet other variations of methods to treat allergic rhinitis, stimulation may be delivered both on a scheduled basis and in response to symptoms of allergic rhinitis or non-allergic rhinitis. In some variations of methods to treat allergic rhinitis, the methods may comprise delivery of stimulation in combination with nose blowing. For example, a user may blow his or her nose after a round of stimulation, or a user may pause stimulus delivery one or more times to blow his or her nose during a round of stimulation. Nose blowing may expel any material accumulated in the nasal passageways during stimulation, such as a buildup of tear secretions and/or mucus. In the case of allergic rhinitis, expelling this accumulated material may contribute to flushing of allergens out of the nose.

As another example, to treat nasal congestion, stimulation may in some variations be delivered to a subject as needed and/or according to a pre-determined regimen. In some instances, a user may use one of the stimulation devices described herein to provide a round of stimulation when the user experiences symptoms of nasal congestion, such as but not limited to difficulty with nasal breathing, ear fullness, facial pain, facial and/or intracranial pressure, decreased sense of smell and/or taste, dizziness, post-nasal discharge, and/or thick nasal discharge. In some variations, a round of stimulation may have a suitable duration, such as but not limited to between about 5 seconds and about 180 seconds, or between about 10 seconds and about 60 seconds. In other variations, a user may deliver a round of stimulation until the user notices an acute reduction in symptoms. When stimulation is delivered on an as-needed basis, a user may deliver any suitable number of rounds of stimulation per day. In some variations, the total number of rounds of stimulation may be limited to 10 per day. In other variations of methods to treat nasal congestion, the devices described herein may be used to provide stimulation on a scheduled basis. For example, in some variations in which the stimulation devices described herein are used to treat nasal congestion, a round of stimulation may be delivered between 2 and 10 times per day, for a plurality of days, on a regular pattern. Such a pattern may be, for example, every 12 hours, every 8 hours, every 6 waking hours, every 4 waking hours, every 3 waking hours, every 2 waking hours, every 1.5 waking hours, or the like. In yet other variations of methods to treat nasal congestion, stimulation may be delivered both on a scheduled basis and in response to symptoms of nasal congestion.

As another example, to treat ocular allergy, stimulation may in some variations be delivered to a subject as needed and/or according to a pre-determined regimen. In some instances, a user may use one of the stimulation devices described herein to provide a round of stimulation when the user experiences symptoms of ocular allergy, such as but not limited to swelling or puffiness, itching, tearing, and/or discharge. In some variations, a round of stimulation may have a suitable duration, such as but not limited to between about 5 seconds and about 180 seconds, or between about 10 seconds and about 60 seconds. In other variations, a user may deliver a round of stimulation until a desired effect occurs (e.g., increased tearing). When stimulation is delivered on an as-needed basis, a user may deliver any suitable number of rounds of stimulation per day. In some variations, the total number of rounds of stimulation may be limited to 10 per day. In other variations of methods to treat ocular allergy, the devices described herein may be used to provide stimulation on a scheduled basis. For example, in some variations in which the stimulation devices described herein are used to treat ocular allergy, a round of stimulation may be delivered between 2 and 10 times per day, for a plurality of days, on a regular pattern. Such a pattern may be, for example, every 12 hours, every 8 hours, every 6 waking hours, every 4 waking hours, every 3 waking hours, every 2 waking hours, every 1.5 waking hours, or the like. In yet other variations of methods to treat ocular allergy, stimulation may be delivered both on a scheduled basis and in response to symptoms of ocular allergy.

It should be appreciated that the methods described herein may comprise delivering a stimulus as described herein according to other suitable treatment regimens for treating allergic rhinitis, non-allergic rhinitis, nasal congestion, ocular allergy, and/or symptoms associated with these conditions. For example, stimuli may be delivered at least once daily, at least once weekly, or the like. In some variations, the stimulation devices may be used to deliver multiple rounds of stimulation each day (e.g., at least two treatments daily, at least three treatments daily, at least four treatments daily, at least five treatments daily, at least six treatments daily, at least seven treatments daily, at least eight treatments daily, between two and ten times daily, between four and eight times daily, or the like). In some variations, the stimulation may be delivered at certain times of day. In other variations, the stimulation may be delivered at any time during the day as desired or determined by the user. When the device is used to provide stimulation on a scheduled basis, in some variations each round of stimulation may be the same length (e.g., about 30 seconds, about 1 minute, about 2 minutes, about 3 minutes, about 4 minutes, about 5 minutes, about 10 minutes, or longer than 10 minutes). In other variations, some rounds of stimulation may have different predetermined lengths. In yet other variations, the user may choose the length of the round of stimulation. In some of these variations, the user may be given a minimum stimulation time (e.g., about 5 seconds, about 10 seconds, about 30 seconds, about 1 minute, about 2 minutes, about 3 minutes, about 5 minutes, or the like) and/or a maximum stimulation time (e.g., about 1 minute, about 2 minutes, about 3 minutes, about 5 minutes, about 10 minutes, about 20 minutes, or the like). In some instances, the delivery schedule or stimulation parameters may be changed based on the time of day (e.g., daytime use vs. nighttime use). In some of these variations, the stimulator may comprise (e.g., as part of a control subsystem) one or more counters and intelligence (e.g., a microcontroller, programmable logic (e.g., a field-programmable gate array), or application-specific integrated circuit (ASIC)). Other treatment regimens that may be used for the methods described herein may include suitable treatment regimens described in U.S. application Ser. No. 14/256,915, filed Apr. 18, 2014, and titled "NASAL STIMULATION DEVICES AND METHODS," which was previously incorporated by reference in its entirety.

In some variations, methods may comprise delivering a stimulus as described herein in combination with other forms of therapy for allergic rhinitis, non-allergic rhinitis, nasal congestion, ocular allergy, and/or symptoms associated with these conditions. For example, in some variations the methods may comprise delivering a stimulus in combination with pharmacologic therapy, such as but not limited to intranasal steroids, oral antihistamines, or anti-IgE. This combined approach may be beneficial as compared to pharmacologic therapy alone due to reduced durations and/or reduced dosages of pharmacologic therapy, which may in turn result in improved safety profiles (i.e., reduced unwanted side effects from such pharmacologic therapy).

Treatment Effects

In some variations, the treatment regimens described herein may be used to treat rhinitis, including allergic rhinitis (acute and/or chronic) and/or non-allergic rhinitis (acute and/or chronic), nasal congestion, ocular allergy, and/or symptoms associated with these conditions. In contrast to current treatment options, the treatment regimens using the stimulators described herein may provide rapid and marked improvement in objective measures of health and symptomatic relief, and may have fewer unwanted side effects. In some variations, the treatment regimens of providing the stimuli described herein may cause periodic or regular activation of the nasolacrimal reflex, which may in turn treat allergic rhinitis, non-allergic rhinitis, nasal congestion, ocular allergy, and/or the symptoms associated with these conditions.

In some variations, the treatment methods described herein for treating allergic rhinitis may result in improvements in measurements of one or more of the thickness and/or volume of lamina propia tissue (e.g., as measured by direct visual examination of the sinus cavity (e.g., by endoscopic examination or speculum examination), use of imaging modalities such as CT or MRI, or the like); redness of nasal mucosa; thickness and/or volume of clear airway passages (e.g., as measured by direct visual examination of the sinus cavity (e.g., by endoscopic examination or speculum examination), use of imaging modalities such as CT or MRI, or the like); microbiological assessment of sinus aspirate; degree of inflammation of nasal mucosa; nasal fractional exhaled nitric oxide; peak nasal inspiratory flow; acute and/or chronic change in nasal discharge volume; viscosity of nasal discharge; nasal airway resistance/impedance; rhinorrhea (runny nose); post-nasal drip; sneezing; nasal congestion; mouth breathing; coughing; headache; anosmia; phlegm volume; itchiness; and/or pain.

In some variations, the treatment methods described herein for treating non-allergic rhinitis may result in improvements in measures of one or more of the thickness and/or volume of lamina propia tissue (e.g., as measured by direct visual examination of the sinus cavity (e.g., by endoscopic examination or speculum examination), use of imaging modalities such as CT or MRI, or the like); redness of nasal mucosa; thickness and/or volume of clear airway passages (e.g., as measured by direct visual examination of the sinus cavity (e.g., by endoscopic examination or speculum examination), use of imaging modalities such as CT or MRI, or the like); microbiological assessment of sinus aspirate; degree of inflammation of nasal mucosa; degree of inflammation of nasal mucosa; nasal fractional exhaled nitric oxide; peak nasal inspiratory flow; acute and/or chronic change in nasal discharge volume; viscosity of nasal discharge; nasal airway resistance/impedance; rhinorrhea (runny nose); post-nasal drip; sneezing; nasal congestion; mouth breathing; coughing; headache; anosmia; phlegm volume; itchiness; and/or pain.

In some variations, the treatment methods described herein for treating nasal congestion may result in improvements in measures of one or more of the thickness and/or volume of lamina propia tissue (e.g., as measured by direct visual examination of the sinus cavity (e.g., by endoscopic examination or speculum examination), use of imaging modalities such as CT or MRI, or the like); redness of nasal mucosa; thickness and/or volume of clear airway passages (e.g., as measured by direct visual examination of the sinus cavity (e.g., by endoscopic examination or speculum examination), use of imaging modalities such as CT or MM, or the like); stuffy nose; and/or breathing through the mouth.

In some variations, the treatment methods described herein for treating ocular allergy may result in improvements in measures of one or more of itching; chemosis; eyelid swelling; excessive tearing; foreign body sensation; and/or ocular discomfort.

EXAMPLE

A study will be carried out to explore the effectiveness of electrical stimulation as described herein for the treatment of symptoms of allergic rhinitis.

Figure 11A:
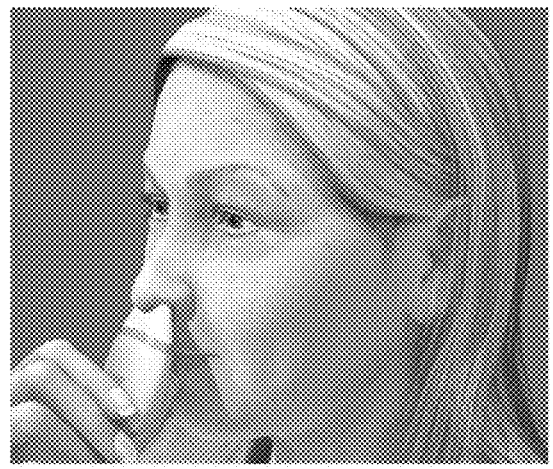
FIGS. 11A-11B illustrate placement of an interventional stimulator and a control stimulator.
Figure 11B:

Participants will be randomized between 1 of 2 treatment sequences. In a first sequence, participants will use an interventional device to apply intranasal electrical stimulation during a first visit, and will use a control device during a second visit. In a second sequence, participants will use a control device during a first visit, and will use an interventional device to apply intranasal electrical stimulation during a second visit. The interventional and control devices will be visually identical, but only the interventional device will generate electrical stimulation. The control device will apply only mechanical stimulation. The interventional device will be applied in the upper part of the nose in order to stimulate the nasolacrimal reflex pathways by gently activating the anterior ethmoidal nerve, a sub-branch of the ophthalmic branch of the trigeminal nerve that provides neural input to the superior salivatory nucleus in the brainstem, as shown in FIG. 11A. The control device will be applied only in the lower part of the nose to avoid activation of the nasolacrimal reflex, as shown in FIG. 11B. Randomization will be stratified by type of allergy (seasonal versus perennial). During the treatment sequences, participants will apply electrical/mechanical stimulation with the interventional device/control device for 3 minutes.

The interventional device will comprise a device having features shown and described with respect to FIGS. 1A-1E. The interventional device will comprise a reusable stimulator body configured to generate an electrical stimulus, and a disposable stimulator probe attachable to the stimulator body. The stimulator probe will comprise two nasal insertion prongs configured to be inserted into a participant's nasal cavity, with each prong comprising a hydrogel electrode. The stimulator body will comprise a user interface comprising two buttons, which will allow the participant to turn on the stimulator and change the stimulus parameters, and light-emitting diodes to indicate the stimulation level being delivered. The interventional device will further include a charger configured to recharge a battery within the stimulator body and a reusable cover configured to be placed over and protect the stimulator probe.

The stimulator body will be configured to deliver five different levels of stimulation. Setting 1 will have a stimulation frequency of 30 Hz; a minimum stimulation current amplitude of 0.7 mA, a maximum stimulation current amplitude of 0.7 mA, and thus no variation in maximum stimulation current amplitude; a minimum pulse width of 0 µs; a maximum pulse width of 300 µs; a pulse width modulation frequency of 1 Hz (rising and falling according to an exponential function); a minimum charge injection per phase (at 0 µs pulse width) of 0 µC; a maximum charge injection per phase (at 0.7 mA and 300 µs) of 0.21 µC; and a pulse shape that is cycled between four periods. The first period will comprise a two-phase current-controlled waveform with symmetrical phases. The second period will comprise a current-controlled first phase, followed by a voltage-controlled second phase. The first phase will have a current sourced by a first electrode and sunk by a second electrode, while the second phase will have a current sourced by the second electrode and sunk by the first electrode. The third period will comprise a two-phase current-controlled waveform with symmetrical phases (i.e., the third period may be the same as the first period). The fourth period will comprise a current-controlled first phase, followed by a voltage-controlled second phase. The first phase will have a current sourced by the second electrode and sunk by the first electrode, while the second phase will have a current sourced by the first electrode and sunk by the second electrode. In each period, the pulses will be charged-balanced. Setting 2 will have a stimulation frequency of 37.5 Hz; a minimum stimulation current amplitude of 1.33 mA, a maximum stimulation current amplitude of 1.5 mA, a variation in maximum stimulation current amplitude of 0.17 mA, and an amplitude modulation frequency of 2.1 Hz; a minimum pulse width of 0 µs; a maximum pulse width of 300 µs; a pulse width modulation frequency of 1 Hz (rising and falling according to an exponential function); a minimum charge injection per phase (at 0 µs pulse width) of 0 µC; a maximum charge injection per phase (at 1.5 mA and 300 µs) of 0.45 µC; and a pulse shape that is modulated as described above with respect to Setting 1. Setting 3 will have a stimulation frequency of 45 Hz; a minimum stimulation current amplitude of 2.17 mA, a maximum stimulation current amplitude of 2.5 mA, a variation in maximum stimulation current amplitude of 0.33 mA, and an amplitude modulation frequency of 2.6 Hz; a minimum pulse width of 0 µs; a maximum pulse width of 300 µs; a pulse width modulation frequency of 1 Hz (rising and falling according to an exponential function); a minimum charge injection per phase (at 0 µs pulse width) of 0 µC; a maximum charge injection per phase (at 2.5 mA and 300 µs) of 0.75 µC; and a pulse shape that is modulated as described above with respect to Setting 1. Setting 4 will have a stimulation frequency of 52.5 Hz; a minimum stimulation current amplitude of 3.2 mA, a maximum stimulation current amplitude of 3.7 mA, a variation in maximum stimulation current amplitude of 0.5 mA, and an amplitude modulation frequency of 2.8 Hz; a minimum pulse width of 0 µs; a maximum pulse width of 300 µs; a pulse width modulation frequency of 1 Hz (rising and falling according to an exponential function); a minimum charge injection per phase (at 0 µs pulse width) of 0 µC; a maximum charge injection per phase (at 3.7 mA and 300 µs) of 1.11 µC; and a pulse shape that is modulated as described above with respect to Setting 1. Setting 5 will have a stimulation frequency of 60 Hz; a minimum stimulation current amplitude of 4.3 mA, a maximum stimulation current amplitude of 5.0 mA, a variation in maximum stimulation current amplitude of 0.67 mA, and an amplitude modulation frequency of 2.5 Hz; a minimum pulse width of 0 µs; a maximum pulse width of 300 µs; a pulse width modulation frequency of 1 Hz (rising and falling according to an exponential function); a minimum charge injection per phase (at 0 µs pulse width) of 0 µC; a maximum charge injection per phase (at 5.0 mA and 300 µs) of 1.5 µC; and a pulse shape that is modulated as described above with respect to Setting 1. The control device will look identical to the interventional device, but will not deliver electrical stimulation.

A number of measures of effectiveness of intranasal stimulation for treatment of the symptoms of allergic rhinitis will be used. Measures will include participant-assessed allergic rhinitis symptom score, nasal inflammation score, peak nasal inspiratory flow, mass of nasal secretions, nasal thermal scan (used as a surrogate marker of inflammatory changes of the nasal cavity), and nasal fractional exhaled nitric oxide (an increase in fractional exhaled nitric oxide may reflect a permanent inflammation of the sinus mucosa).

Allergic rhinitis symptom score: Each participant will evaluate four allergic rhinitis symptoms, including nasal itching, nasal congestion, rhinorrhea, and sneezing on a 0 to 3 scale (0=no sign/symptom is evident; 1=sign/symptom clearly present, but minimal awareness–easily tolerated; 2=definite awareness of sign/symptom that is bothersome, but tolerable; 3=sign/symptom that is hard to tolerate; causes interference with activities). Symptoms will be evaluated at 5±1 minutes before nasal stimulation, and at 5±1, 10±1, 15±1, 20±1, 30±1, 45±1, 60±5, 75±5, 90±5, 105±5, 120±5, 135±5, 150±5, 165±5, and 180±5 minutes after nasal stimulation. It is hypothesized that a composite score (sum) of the four symptoms (nasal itching, nasal congestion, rhinorrhea, and sneezing) will be lower after intranasal electrical stimulation than prior to stimulation. It is hypothesized that activation of the nasolacrimal reflex, via stimulus delivery to the anterior ethmoidal nerve, will induce increased rhinorrhea and a local sympathetic rebound leading to vasoconstriction in the nasal cavity. Together, increased rhinorrhea and local vasoconstriction will lead to a relief of symptoms usually associated with allergic rhinitis.

Nasal inflammation score: Nasal inflammation score will be evaluated by an investigator on a 0 to 4 scale using nasal digital videos of each nostril, where characteristics of redness, swelling, and abnormal nasal secretions will be evaluated. Nasal inflammation will be evaluated prior to stimulation (within 30 minutes prior to the first evaluation of symptoms at −5±1 minutes before stimulation) and at 180±5 minutes after nasal stimulation. It is hypothesized that nasal inflammation will decrease after intranasal electrical stimulation.

Peak nasal inspiratory flow: Nasal peak inspiratory flow readings will be made using an inspiratory flow meter with nasal adaptor. Measurements will be made in a standing position. Subjects will be instructed to exhale residual volume, place a face mask over the mouth and nose to create a good seal around the face mask, and then inhale forcefully to total lung capacity, through the nose, with mouth closed. This maneuver should be a short, sharp inspiratory action of about 1 second in duration. Peak nasal inspiratory flow will be evaluated prior to stimulation (within 30 minutes prior to the first evaluation of symptoms at −5±1 minutes before stimulation) and at 60±5, 120±5, and 180±5 minutes after stimulation. Three measurements will be made at each time point. It is hypothesized that peak nasal inspiratory flow over the time points will initially transiently decrease, and then increase.

Mass of nasal secretions: Each subject will be given a bag of pre-weighed disposable tissues to use during the course of each measurement period. Used tissues will be placed in a closed disposable plastic container, as to minimize evaporation. The container of both used and unused tissues will be weighed after the measurement period is complete and the mass increase, if any, due to nasal secretions will be recorded. The mass of nasal secretions will be measured prior to stimulation (within 30 minutes prior to the first evaluation of symptoms at −5±1 minutes before stimulation), and at 10±1, 60±5, 120±5, and 180±5 minutes after stimulation. It is hypothesized that the mass of nasal secretions over the time points will initially transiently increase, and then decrease.

Nasal thermal scan: For nasal thermal scanning, the temperature of the tissue surrounding the nasal area will be measured as a surrogate for inflammation. A thermal camera will be used to capture thermal images of the nasal area. The temperature of the tissue will be recorded to identify when an allergic response causing vasodilatation is occurring, as identified by an acute increase in temperature. Nasal thermal scans will be conducted prior to stimulation (within 30 minutes prior to the first evaluation of symptoms at −5±1 minutes before stimulation), and at 15±1, 30±1, 45±1, 60±5, 90±5, 120±5, 150±5, and 180±5 minutes after stimulation. When thermal scans are conducted at the same time point as collection of nasal secretions, the thermal image will be taken before the collection of nasal secretions. It is hypothesized that stimulation will result in more rapid temperature normalization.

Nasal fractional exhaled nitric oxide: A fractional exhaled nitric oxide-sensing machine will be used to measure nitric oxide levels from exhalation. Fractional exhaled nitric oxide will be evaluated prior to stimulation (within 30 minutes prior to the first evaluation of symptoms at −5±1 minutes before stimulation), and at 30±1, 60±5, 90±5, 120±5, 150±5, and 180±5 minutes after stimulation. It is expected that levels of nitric oxide will increase as the tissue undergoes an eosinophilic response to the allergen, and that stimulation will result in decreased nasal fractional exhaled nitric oxide.

The invention claimed is:

1. A method for treating rhinitis, the method comprising:
    advancing of a handheld nasal stimulator including a stimulator body towards a first nostril and a second nostril of a patient;
    positioning, via the first nostril of the patient and as a result of the advancing, a first electrode extending from the stimulator body in contact with a nasal mucosa of a first nasal turbinate of the patient;
    positioning, via the second nostril of the patient and as a result of the advancing, a second electrode extending from the stimulator body in contact with a nasal mucosa of a second nasal turbinate of the patient; and
    delivering an electrical stimulus via the first electrode and the second electrode to thereby treat rhinitis in the patient.

2. The method of claim 1, wherein the electrical stimulus is delivered in response to one or more symptoms of rhinitis.

3. The method of claim 2, wherein the symptoms of rhinitis comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

4. The method of claim 1, wherein the electrical stimulus is delivered more than once per day on a scheduled basis.

5. The method of claim 1, wherein the first electrode and the second electrode are positioned adjacent to opposing sides of a nasal septum of the patient.

6. A method of treating rhinitis, the method comprising:
advancing a handheld nasal stimulator including a stimulator body towards a nose of a subject;
positioning, as a result of the advancing, an electrode extending from the stimulator body in contact with a nasal mucosa of a nasal turbinate of the subject; and
delivering an electrical stimulus via the electrode to the nasal mucosa of the subject to thereby improve rhinitis of the subject, wherein the stimulator body of the handheld stimulator comprises a control subsystem to control the electrical stimulus.

7. The method of claim 6, wherein the electrical stimulus is delivered in response to one or more symptoms of rhinitis.

8. The method of claim 7, wherein the one or more symptoms of rhinitis comprise one or more of itching, sneezing, congestion, runny nose, post-nasal drip, mouth breathing, coughing, fatigue, headache, anosmia, phlegm, throat irritation, periorbital puffiness, watery eyes, ear pain, and fullness sensation.

9. The method of claim 6, wherein the electrical stimulus is delivered at least once daily during a treatment period.

10. The method of claim 9, wherein the electrical stimulus is delivered on a scheduled basis during the treatment period.

11. A method for treating ocular allergy, the method comprising:
advancing a stimulator body of a handheld nasal stimulator towards a first nostril and a second nostril of a patient;
positioning, via the first nostril of the patient and as a result of the advancing, a first electrode extending from the stimulator body in contact with a nasal mucosa of a first nasal turbinate of the patient;
positioning, via the second nostril of the patient and as a result of the advancing, a second electrode extending from the stimulator body in contact with a nasal mucosa of a second nasal turbinate of the patient; and
delivering an electrical stimulus the first electrode and the second electrode to thereby treat ocular allergy in the patient.

12. The method of claim 11, wherein the electrical stimulus is delivered in response to one or more symptoms of ocular allergy.

13. The method of claim 12, wherein the one or more symptoms of ocular allergy comprise one or more of swelling, puffiness, itching, tearing, and discharge.

14. The method of claim 11, wherein the electrical stimulus is delivered more than once per day on a scheduled basis.

15. The method of claim 11, wherein the first electrode and the second electrode are positioned adjacent to opposing sides of a nasal septum of the patient.

16. A method of treating ocular allergy, the method comprising:
advancing a handheld nasal stimulator including a stimulator body towards a nose of a subject;
positioning, as a result of the advancing, an electrode extending from the stimulator body in contact with a nasal mucosa of a nasal turbinate of the subject;
delivering an electrical stimulus via the electrode to the nasal mucosa of the subject to thereby improve ocular allergy of the subject, wherein the stimulator body of the handheld stimulator comprises a control subsystem to control the electrical stimulus.

17. The method of claim 16, wherein the electrical stimulus is delivered in response to one or more symptoms of ocular allergy.

18. The method of claim 17, wherein the one or more symptoms of ocular allergy comprise one or more of swelling, puffiness, itching, tearing, and discharge.

\* \* \* \* \*